(12) United States Patent
Wang et al.

(10) Patent No.: US 12,092,536 B1
(45) Date of Patent: Sep. 17, 2024

(54) MULTI-MODAL PRESSURE SENSOR

(71) Applicants: Chunlei Wang, Miami, FL (US); Borzooye Jafarizadeh, Miami, FL (US); Azmal Chowdhury, Miami, FL (US); Iman Khakpour, Miami, FL (US); Nezih Pala, Miami, FL (US)

(72) Inventors: Chunlei Wang, Miami, FL (US); Borzooye Jafarizadeh, Miami, FL (US); Azmal Chowdhury, Miami, FL (US); Iman Khakpour, Miami, FL (US); Nezih Pala, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/300,745

(22) Filed: Apr. 14, 2023

(51) Int. Cl.
*G01L 1/18* (2006.01)
*A61B 5/00* (2006.01)

(52) U.S. Cl.
CPC ............ *G01L 1/18* (2013.01); *A61B 5/00* (2013.01); *A61B 2562/0247* (2013.01); *A61B 2562/0261* (2013.01); *A61B 2562/12* (2013.01)

(58) Field of Classification Search
CPC ..... G01L 1/18; A61B 5/00; A61B 2562/0247; A61B 2562/0261; A61B 2562/12
See application file for complete search history.

(56) References Cited

U.S. PATENT DOCUMENTS

2023/0340225 A1* 10/2023 Wang .................. C08J 3/07

OTHER PUBLICATIONS

Zhang, Haixia. All-in-one piezoresistive-sensing patch integrated with micro-supercapacitor, Nano Energy vol. 53, Nov. 2018, pp. 189-197, https://doi.org/10.1016/j.nanoen.2018.08.041 (Year: 2018).*
Aw, Kean. A Dielectric Elastomer-Based Multimodal Capacitive Sensor, Sensors MDPI, Sensors 2022, 22(2), 622, https://www.mdpi.com/1424-8220/22/2/622 (Year: 2022).*

(Continued)

*Primary Examiner* — Michael W Kahelin
*Assistant Examiner* — Moussa Haddad
(74) *Attorney, Agent, or Firm* — SALIWANCHIK, LLOYD & EISENSCHENK

(57) ABSTRACT

The subject invention is concerned with systems and methods advantageously applying finite element analysis to establish design rules for a highly sensitive piezo-resistive pressure sensor with an output that is high enough to be detectable by simple and inexpensive circuits and therefore ensure wearability. Four frequently reported micro-feature shapes in micro-patterned piezo-resistive sensors are provided, where the micro-dome and micro-pyramid yield the highest sensitivity. Investigations of different conductivity values of micro-patterned elastomers show that coating the elastomer with a conductive material (e.g., a metallic coating) leads to higher current response when compared to composited conductive elastomers. Advantageous geometric parameters and spatial configurations of micro-pyramid design of piezo-resistive sensors are provided. Results show that an enhanced sensitivity and higher current output can be achieved by a lower spatial density configuration of three micro-features per millimeter length, a smaller feature size of around 100 μm, and a 60-50 degrees pyramid angle.

10 Claims, 48 Drawing Sheets

(56) References Cited

OTHER PUBLICATIONS

Chen, Xuyuan. Highly Sensitive and Flexible Capacitive Pressure Sensors Based on Vertical Graphene and Micro-Pyramidal Dielectric Layer, Nanomaterials (Basel). Feb. 2023; 13(4): 701. doi: 10.3390/nano13040701 (Year: 2023).*

Liu, Yingtao. PDMS Sponges with Embedded Carbon Nanotubes as Piezoresistive Sensors for Human Motion Detection, Nanomaterials, Jul. 1, 2021, https://shareok.org/bitstream/handle/11244/335052/Herren_2022_PDMSSPonges.pdf?sequence=1 (Year: 2021).*

Zhao, Haoyu. Tactile Sensing Based on Capacitive Sensing and Electrical Resistance Tomography, The University of Manchester Ph. D. thesis Department of Electrical and Electronic Engineering, 2022. https://pure.manchester.ac.uk/ws/portalfiles/portal/261207776/FULL_TEXT.PDF (Year: 2022).*

Cohen, Daniel. A Highly Elastic, Capacitive Strain Gauge Based on Percolating Nanotube Networks, American Chemical Society, Nano Lett. Mar. 12, 2012, pp. 1821-1825, https://doi.org/10.1021/nl204052z (Year: 2012).*

Zhang, Haixia "Hybrid porous micro structured finger skin inspired self-powered electronic skin system for pressure sensing and sliding detection" Nano Energy vol. 51, Sep. 2018, pp. 496-503 (Year: 2018).*

Wang, Zongrong "High Sensitivity, Wearable, Piezoresistive Pressure Sensors Based on Irregular Microhump Structures and Its Applications in Body Motion Sensing", Nano Micro Small, vol. 12 Iss. Jul. 28, 27, 2016, pp. 3827-3836 (Year: 2016).*

Wang, Luxian. "PDMS/MWCNT-based tactile sensor array with coplanar electrodes for crosstalk suppression" Microsystems & Nanoengineering vol. 2, Article No. 16065 (2016) pp. 1-8 (Year: 2016).*

Yu et al. ("A soft tactile sensing array with high sensitivity based on MWCNTs-PDMS composite of hierarchically porous structure", Sep. 7, 2023, Smart Materials and Structures, vol. 32, No. 10 (Year: 2023).*

Panda et al. ("PDMS/MWCNT nanocomposites as capacitive pressure sensor and electromagnetic interference shielding materials" Journal of Materials Science: Materials in Electronics, Published: May 21, 2021 vol. 32, pp. 16215-16229, (2021) (Year: 2021).*

Herren et al. ("Rapid Microwave Polymerization of Porous Nanocomposites with Piezoresistive Sensing Function" Nanomaterials 2020, 10(2), 233 pp. 1-17) (Year: 2020).*

Chowdhury et al. "Wearable Capacitive Pressure Sensor for Contact and Non-Contact Sensing and Pulse Waveform Monitoring" Molecules. Oct. 2022; 27(20): 6872. Published online Oct. 13, 2022. doi: 10.3390/molecules27206872 (Year: 2022).*

Li et al. "A porous and air gap elastomeric dielectric layer for wearable capacitive pressure sensor with high sensitivity and a wide detection range" Doi: 10.1039/DOTC00443J (Paper) J. Mater. Chem. C, 2020, 8, 11468-11476, Jul. 1, 2020 (Year: 2020).*

* cited by examiner

MULTI-MODAL PRESSURE SENSOR

GOVERNMENT SUPPORT

This invention was made with government support under 1648451 awarded by the National Science Foundation. The government has certain rights in the invention.

BACKGROUND

Wearable flexible piezo-resistive pressure sensors hold a wide-ranging potential in human health monitoring, electronic skin, robotic limbs, and other human-machine interfaces. Out of the most successful recent efforts for arterial pulse monitoring are sensors with micro-patterned conductive elastomers. However, a low-current output signal (typically in the range of nano-amperes) and bulky and expensive measurement equipment for useful signal acquisition inhibits their wearability.

Sensitive and flexible pressure sensors have invoked a considerable interest for applications ranging from tactile sensing, physiological sensing, and flexible electronics. The barrier between high sensitivity and low fabrication cost needs to be addressed to commercialize such flexible pressure sensors.

Flexible wearable pressure sensors have garnered tremendous attention in recent years due to their benefits in many applications, including healthcare monitoring, electronic skin, tactile sensing, touch screens, electronic textiles, and soft robotics. Numerous flexible pressure sensors have been developed, capable of low-pressure and high-pressure detection applications such as monitoring wrist arterial pulse waveform (low-pressure regime) and monitoring tactile pressure sensing (high-pressure regime). These pressure sensors are categorized into capacitive, piezoresistive, piezoelectric, and triboelectric sensors. Among these different sensors, capacitive sensors have a simple architecture that requires a dielectric layer sandwiched between two parallel plate electrodes. Capacitive sensors require low operating voltage, immunity against temperature, and a simple data readout system.

The sensitivity of pressure sensors is an essential parameter since the sensor's performance can be characterized by sensitivity. The sensor materials and fabrication must be carefully selected and optimized to realize pressure sensors with high sensitivity while keeping the cost acceptable. Therefore, developing a simple and low-cost fabrication carries immense importance for commercial applicability. Capacitive pressure sensors (CPS) based on a parallel plate mechanism with a solid polymer-based dielectric layer demonstrated low-pressure sensitivity in both low- and high-pressure applications. There have been many efforts towards improving the pressure sensitivity, especially in the low-pressure regime, to detect minute pressure such as the pulse waveform from the wrist artery. These efforts are concentrated on improving the dielectric/electrode layer's structural properties and the polymer layer's dielectric properties. It has been shown that the presence of microstructures on the sensing layer improves the pressure sensitivity on both capacitive and piezoresistive pressure sensors. To reduce the stiffness of the dielectric layer/electrodes, different micro-structuring approaches were adapted, such as micro pyramid structure, micro dome structure, and micropillar structure. However, creating such microstructures on the dielectric layer/electrode requires complicated and expensive fabrication processes An alternative approach to reduce the stiffness of the dielectric layer is to use polymer foam as the dielectric layer for improved pressure response than a solid dielectric layer-based sensor. Several methods have been implemented to realize polymer layers with porous/foamy structures, including foaming, emulsion method, dip coating, and sacrificial template. Sacrificial template-assisted porous dielectric layer fabrication is a suitable and low-cost approach to reducing the stiffness of the dielectric layer without any complicated micropatterning techniques. The stiffness reduction technique is achieved by introducing pores inside the polymer dielectric layer by adding different sacrificial templates such as sugar, salt, PS beads, etc. For instance, a bio-inspired porous dielectric layer-based CPS can use polystyrene bead as the sacrificial template. The sensor achieved a highest-pressure sensitivity of 0.63 $kPa^{-1}$ and a LoD of 2.42 Pa.

However, the porous dielectric layer-based CPS's pressure sensitivity is lower than other micropatterned-based sensing mechanisms. The sensing performances can be improved by functionalizing the porous/foamy dielectric layer with high dielectric constant dopants such as $CaCu_3Ti_4O_{12}$ (CCTO) or by adding high conductive nanofiller materials such as carbon nanotubes, carbon black, graphene nano platelets, etc. According to previous reports, adding high conductivity nanofiller materials results in a better response in improving the pressure sensitivity than adding high dielectric permittivity dopants. The dielectric constant of the polymer material can be significantly (CCTO) or by adding high conductive nanofiller materials such as carbon nanotubes, carbon black, graphene nano platelets, etc. According to previous reports, adding high conductivity nanofiller materials results in a better response in improving the pressure sensitivity than adding high dielectric permittivity dopants. The dielectric constant of the polymer material can be significantly improved by adding a conductive nanofiller below the percolation threshold that improves the pressure sensitivity of the capacitive sensor.

BRIEF SUMMARY

Embodiments of the subject invention provide novel and advantageous wearable multi-modal pressure sensors for detection and intelligent monitoring of weak human physiological signals. Embodiments can be applied to detection of heart activity (e.g., heartbeat or pulse), muscle movement, lung activity, skin conductance level (SCL), and numerous other application areas. In one embodiment of a sensor, three pressure sensors are stacked on each other to form a multi-modal sensor. As shown in FIGS. 10A-13G, the incorporated sensors can be (but are not exclusively limited to) a supercapacitive sensor (e.g., mode I) piezoresistive sensor (e.g., mode II), and a capacitive sensor (e.g., mode III). The arrangement in the sensor allows for simultaneous detection of a single stimuli by the sensor using parallel modes of operation. For example, when the multi-modal sensor is place on the wrist, the piezoresistive sensor, capacitive, and supercapacitive sensors each, respectively, detect the pressure disturbance on the wrist cause by the heartbeat. Because a single excitation signal can be picked up by 3 sensors with different mechanisms of operation, advantages of the different mechanisms can compounded and the respective shortcomings of each can be diminished.

Embodiments provide strain gauge sensors (e.g., as shown in FIGS. 11A-11B) for detection of planar deformations that can be incorporated into the provided sensing and analysis capabilities (e.g., to provide planar mapping of deformations caused by heartbeat pressure waves.)

Embodiments provide a multi-modal sensor that when compared to each individual respective mono-modal sensor shows a higher signal-to-noise ratio, better reliability, and the capability to detect new or additional data (e.g., blood pressure in addition to heartbeat or pulse data). Embodiments can provide additional needed information for achieving reliable pulse-wave-form monitoring for disease diagnostics and cuffless blood pressure measurement. Realizing these benefits in a wearable manner compared to the costly and inconvenient related art clinical equipment that does not allow seamless monitoring of the human subjects in their daily lives is clinically and commercially advantageous in improving patient outcomes, including prevention or reduction of premature cardiovascular deaths.

Embodiments provide a low-cost sacrificial template-assisted method for creating a capacitive sensor as provided herein, including but not limited to systems and methods for providing a porous polydimethylsiloxane (PDMS) polymer and multiwalled carbon nanotube (MWCNT) composite-based dielectric layer. The provided sensors exhibit high sensitivity of 2.41 kPa$^{-1}$ along with a limit of detection (LoD) of 1.46 Pa, as shown in FIG. 3F and Table 1. While not being bound by theory, the inventors hypothesize that the high sensitivity originates from adding MWCNT to PDMS, increasing the composite polymer's dielectric constant. Embodiments of the provided pressure sensor show excellent stability with cyclic loading of 10,000 cycles, proving the sensor's reliability for robust application. The practicality of the sensor has been shown in applications such as tactile sensing, morse code generator, proximity sensing, and physiological sensing applications.

TABLE 1

Material sensitivity references.

| Material | Sensitivity Region-1 | Sensitivity Region-2 | Year | References |
|---|---|---|---|---|
| Porous PDMS | 0.18 kPa$^{-1}$ | | 2021 | [11] |
| Porous PDMS | 0.3 kPa$^{-1}$ (<50 Pa) | 0.0032 kPa$^{-1}$ (0.2-1 MPa) | 2021 | [31] |
| Polyurethane Sponge, Graphene Nano platelets | .062 kPa$^{-1}$ (<1 kPa) | 0.033 kPa$^{-1}$ (>1 kPa) | 2019 | [22] |
| Porous PDMS, MWCNTs | 2.41 kPa$^{-1}$ (<50 Pa) | 0.11 kPa$^{-1}$ (>1 kPa) | 2022 | The subject invention |

In an embodiment, a wearable multi-modal pressure sensor (WMMPS) for detection and intelligent monitoring of weak human physiological signals can comprise (at least) three pressure sensors vertically stacked within a common sensor footprint, and the three pressure sensors can comprise a supercapacitive and/or strain gauge sensor, a piezoresistive sensor, and a capacitive sensor. The piezoresistive sensor can comprise one or more patterned microfeatures selected from the list consisting of a plurality of patterned micro-domes, a plurality of patterned micro-pyramids, a plurality of patterned micro-cones, and a plurality of patterned micro-pillars. The piezoresistive sensor can comprise the plurality of patterned micro-pyramids, and the plurality of patterned micro-pyramids can be arranged on one side of a porous polymer (e.g., polydimethylsiloxane (PDMS) polymer) and multiwalled carbon nanotube (MWCNT) composite-based dielectric layer. The plurality of patterned micro-pyramids can be coated to provide a conductivity value greater than the conductivity of the uncoated porous PDMS polymer and MWCNT composite-based dielectric layer. The plurality of patterned micro-pyramids can have a conductivity value of, for example, greater than 2 Siemens per meter (S/m) (e.g., equal to or greater than 10 S/m). The plurality of patterned micro-pyramids can have an average pyramid angle (as depicted by "α" in FIG. 6A) of, for example, between 50 and 60 degrees (inclusive or exclusive of the endpoints). The plurality of patterned micro-pyramids can have an average size of micro-pyramids (as depicted by "1" in FIG. 6A) of, for example, 150 micrometers (μm) or less. The plurality of patterned micro-pyramids can be patterned with an average number density of, for example, 3 per millimeter (mm−1) or less. The plurality of patterned micro-pyramids can form a functional part of each of the piezoresistive sensor and the capacitive sensor, respectively. The porous polymer (e.g., PDMS polymer) and MWCNT composite-based dielectric layer can comprise a MWCNT concentration of from 0.1 weight percentage (wt. %) to 10 wt. % (e.g., from 0.5 wt. % to 5 wt. %, such as 1.6 wt. % or about 1.6 wt. %). The WMMPS can have a sensitivity in a range of, for example, from 1 kiloPascal−1 (kPa−1) to 3 kPa−1 (e.g., 2.41 kPa−1 or about 2.41 kPa−1 and a limit of detection (LoD) in a range of, for example, 1 Pascal (Pa) to 10 Pa (e.g., 1.46 Pa or about 1.46 Pa).

In another embodiment, a method of fabricating a WMMPS for detection and intelligent monitoring of weak human physiological signals can comprise: fabricating a supercapacitive and/or strain gauge sensor; fabricating a piezoresistive sensor; fabricating a capacitive sensor; defining a sensor footprint and placing the capacitive sensor within the sensor footprint; assembling the piezoresistive sensor on top of the capacitive sensor and within the sensor footprint; assembling the supercapacitive or strain gauge sensor on top of the piezoresistive sensor and within the sensor footprint; and connecting each of the supercapacitive and/or strain gauge sensor, the piezoresistive sensor, and the capacitive sensor, respectively, to a respective pair of sensor leads, each respective pair of sensor leads configured and adapted to transmit signals generated by the respective sensor. The respective steps of fabricating the piezoresistive sensor, fabricating the capacitive sensor, and assembling the piezoresistive sensor can each respectively comprise the same sub-step of assembling a porous polymer (e.g., PDMS polymer) and MWCNT composite-based dielectric layer comprising patterned micro-features on top of a conductive layer, with the patterned micro-features in contact with the conductive layer. The step of fabricating the piezoresistive sensor can comprise the sub-steps of: fabricating, via photolithography, a mold comprising patterned cavities for forming the patterned micro-features; adding uncured polymer (e.g., PDMS) and MWCNT to the mold; and curing the polymer (e.g., PDMS) with the MWCNT in the mold to produce the porous polymer (e.g., PDMS polymer) and MWCNT composite-based dielectric layer comprising patterned micro-features. The step of adding uncured polymer (e.g., PDMS and MWCNT to the mold comprising adding sucrose in polymer (e.g., PDMS), MWCNT, and a solvent (e.g., acetone).

BRIEF DESCRIPTION OF DRAWINGS

FIG. 3A shows dependence of the initial capacitance based on the concentration of the MWCNTs (base capacitance ($C_0$) as a function of the MWCNTs concentration.) FIG. 3B shows relative capacitance change ($\Delta C/C_0$) vs. pressure for the PCNT based sensor with varying concentration of MWCNT in wt. %. FIG. 3C shows relative capacitance change ($\Delta C/C_0$) vs. pressure for the PCNT sensor with 1.6 wt. % MWCNTs. The inset shows the pressure sensitivity at the low-pressure range. FIG. 3D shows loading-unloading profiles for the PCNT based sensor with varying concentration of MWCNTs under 1 kPa pressure. FIG. 3E shows loading-unloading profiles for PCNT based sensor with 1.6 wt. % MWCNT concentration under different pressures. FIG. 3F shows sequential loading of ~1.4 Pa pressure on the pressure sensor showing a minimum detection limit of 1.46 Pa.

FIG. 4A shows a stability test of the PCNT based pressure sensor showing stable performance for 10,000 cycles. FIG. 4B shows sensor performance with triangular loading profiles with slow frequencies. FIG. 4C shows sensor performance with triangular loading profiles with high frequencies. FIG. 4D shows an enlarged profile image to show how much the CPS lags, corresponding to the piezoresistive pressure sensor.

FIG. 5A shows detection of finger tapping with irregular intervals. FIG. 5B shows generation of Morse code for signal generation with long and short pressing on the sensor. FIG. 5C shows capability of proximity sensing for hands-free applications. FIG. 5D shows real time monitoring of arterial pulse waveforms from the wrist artery.

FIG. 6A shows a schematic of a micro-pyramid piezo-resistive sensor showing parameters such as pyramid angle "$\alpha$" and pyramid base size "$\ell$". FIG. 6B shows different proposed microfeature shapes for a three dimensional 1.8 mm×1.8 mm piezo-resistive sensor.

FIG. 7A shows change in relative current as a function of normal pressure. FIG. 7B shows passing current as a function of normal applied pressure. FIG. 7C shows a plot of area of contact between the two layers of the sensor as a function of decrease in layer spacing distance. FIG. 7D shows a schematic of a pyramid and cone that undergoes compression and dependence of contact area on decrease in inter-layer spacing distance.

FIG. 8A shows change in relative current as a function of applied normal pressure. FIG. 8B shows current response of the sensor with different conductivity values.

FIG. 9A shows a micro-pyramid geometric design schematic. FIG. 9B shows simulated relative current as a function of applied pressure for different spatial densities. FIG. 9C shows simulated relative current as a function of applied pressure for different pyramid angles "$\alpha$". FIG. 9D shows simulated relative current as a function of applied pressure for different pyramid base sizes, "$\ell$".

FIG. 10A shows a schematic representation of the sensor comprising three parallel modes of operation for reading a heartbeat packaged in a wrist bracelet and wirelessly transmitting the acquired signal. FIG. 10B shows a supercapacitive sensor (marked I), microfabricated piezoresistive sensor (marked II) and capacitive sensor (marked III).

FIG. 11A shows a schematic representation of strain gauge sensor (marked I), a microfabricated piezoresistive sensor (marked II), and a capacitive sensor (marked III). FIG. 11B shows the components that the piezoresistive and capacitive sensor share and where they are connected to the outside circuit.

FIG. 12A schematically illustrates a process by which a mold having pits in the shape of micro-pyramids is fabricated using photolithography; uncured PDMS (polydimethylsiloxane) is poured on the mold; and cured PDMS is detached from the mold having the desired micro-shapes. FIG. 12B shows a photograph of an actual prototype sensor fabricated according to the process shown in FIG. 12A. FIG. 12C shows an SEM of the sensor footprint area used to verify if the shapes of the micro-features conform to the designs. FIG. 12D illustrates the test and characterization process and results comparing three sensors via heartbeat measurements-: (1) a micro-pyramid gold-coated sensor according to a first embodiment of the subject invention; (2) a MWCNT on nylon filter sensor; and (3) a commercially available piezoresistive sensor. FIG. 12E shows an SEM of the sensor gold-plated micro-pyramids used to verify if the shapes and surface finish of the micro-features conform to the designs. FIG. 12F shows an SEM of the sensor used to verify if the sensor conforms to the designs. FIG. 12G shows a photograph of a commercial sensor.

FIG. 13A schematically illustrates a process comprising: preparing a PVA/H3PO4 solution, blade coating tissue paper, drying in an oven for 15 minutes at 70° F., and cutting the dielectric layer to the desired size; the sensor produced; and selected test and characterization results. FIG. 13B shows a photograph of an actual prototype sensor fabricated according to the process shown in FIG. 13A above a schematic representation of the layers of the same sensor. FIG. 13C shows a schematic exploded view of sensor components: top polyimide layer, conductive textile, solid electrolyte, membrane spacer, conductive textile, and bottom polyimide layer. FIG. 13D is a chart showing relative capacitance response to pressure for five different PVA-HPO formulations. Polyvinyl alcohol (PVA) was first diluted in deionized water in a 10 wt. % concentration. Then, different volumes (0 mL, 0.5 mL, 1 mL, 1.5 mL, and 2 mL) of $H_3PO_4$ (HPO) were added to 20 mL PVA solution to prepare the control samples. The concentrations of the five different PVA-HPO formulations were: PVA-HPO-0-20 mL of 10 wt. % PVA and 0 mL of HPO; PVA-HPO-0.5-20 mL of 10 wt. % PVA and 0.5 mL of HPO; PVA-HPO-1-20 mL of 10 wt. % PVA and 1 mL of HPO; PVA-HPO-1.5-20 mL of 10 wt. % PVA and 1.5 mL of HPO; and PVA-HPO-2-20 mL of 10 wt. % PVA and 2 mL of HPO. FIG. 13E is a detailed chart showing relative capacitance response over time for wrist arterial pulse (subject #1). FIG. 13F is a detailed chart showing relative capacitance response over time for wrist arterial pulse (subject #2). FIG. 13G is a detailed chart showing relative capacitance response over time for carotid pulse waveforms.

DETAILED DESCRIPTION

Embodiments of the subject invention provide novel and advantageous wearable multi-modal pressure sensors for advanced detection of human physiological signals (e.g., weak human physiological signals) including but not limited to a heartbeat pulse-wave-form. Embodiments of the multi-modal sensor incorporate several pressure sensors which work in collaboration (and can optionally but advantageously share electrical, structural, or other physical or logical elements) to detect one or more physiological signals simultaneously.

Embodiments provide a wearable multi-modal pressure sensor for detection and intelligent monitoring of weak human physiological signals. Embodiments can be applied to but are not limited to detection of heart activity, muscle movement, lung activity, skin conductance level (SCL), and cuffless blood pressure monitoring. In certain embodiments an arrangement in a sensor allows for simultaneous detection of a single stimuli by the sensor using parallel modes of operation. Embodiments allow reliable and accurate monitoring of signals, advantageously including weak physiological signals, in a wearable manner compared to the costly and inconvenient related art clinical equipment that can fail to provide seamless monitoring of patients (e.g., human subjects, other mammals, or other animals) in their daily lives.

Embodiments provide a higher accuracy and reliability of certain pressure data compared to a single sensor. Authenticity of each signal can be verified by a machine learning algorithm that compares the data from each parallel mode of operation (e.g., by comparing sensor number 1, 2, 3, or more) to the reference sensor and reports only genuine signals arising from physiological activity under investigation (e.g., by effectively disregarding certain pressure variations from intentional or involuntary body movement).

Embodiments provide advanced filtering where different modes of operation have varied response times to the same disturbance. Certain embodiments feed one or more signals through a machine learning algorithm that can reduce noise and improve signal-to-noise ratio.

Embodiments provide systems and methods for gleaning out an increased data output from a limited footprint (e.g., limited physical space, power consumption, or data bandwidth.) In one embodiment of the sensor the parallel sensor modes are stacked on top of each other. This arrangement provides data from a fixed footprint area from several sensors (e.g., advantageously employing 2, 3, or more distinct modes of operation to sense one or more signals.)

Figure 11A:
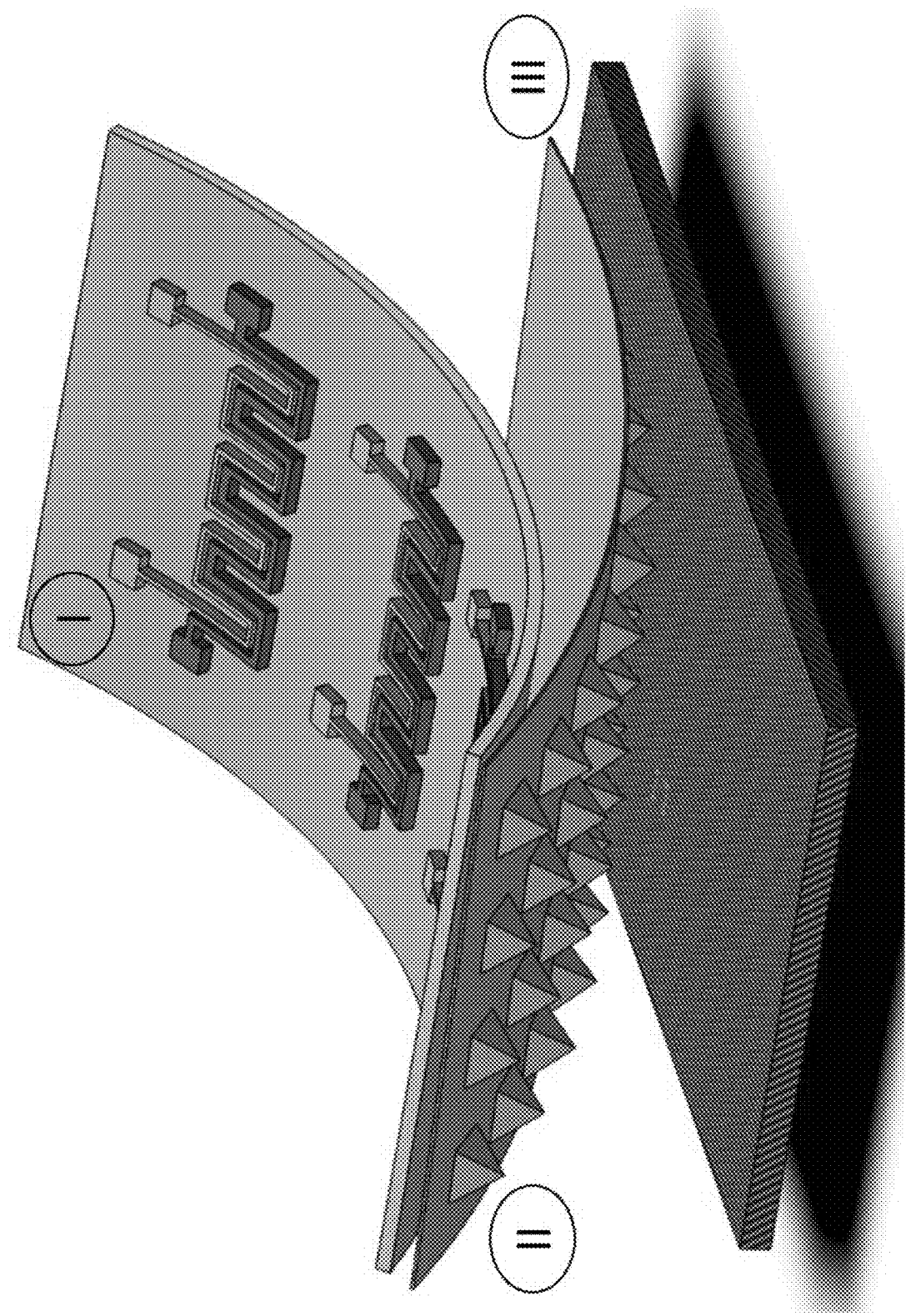
FIGS. 11A-11B show a multi-modal sensor comprising three parallel modes of operation according to an embodiment of the subject invention.
Figure 11B:
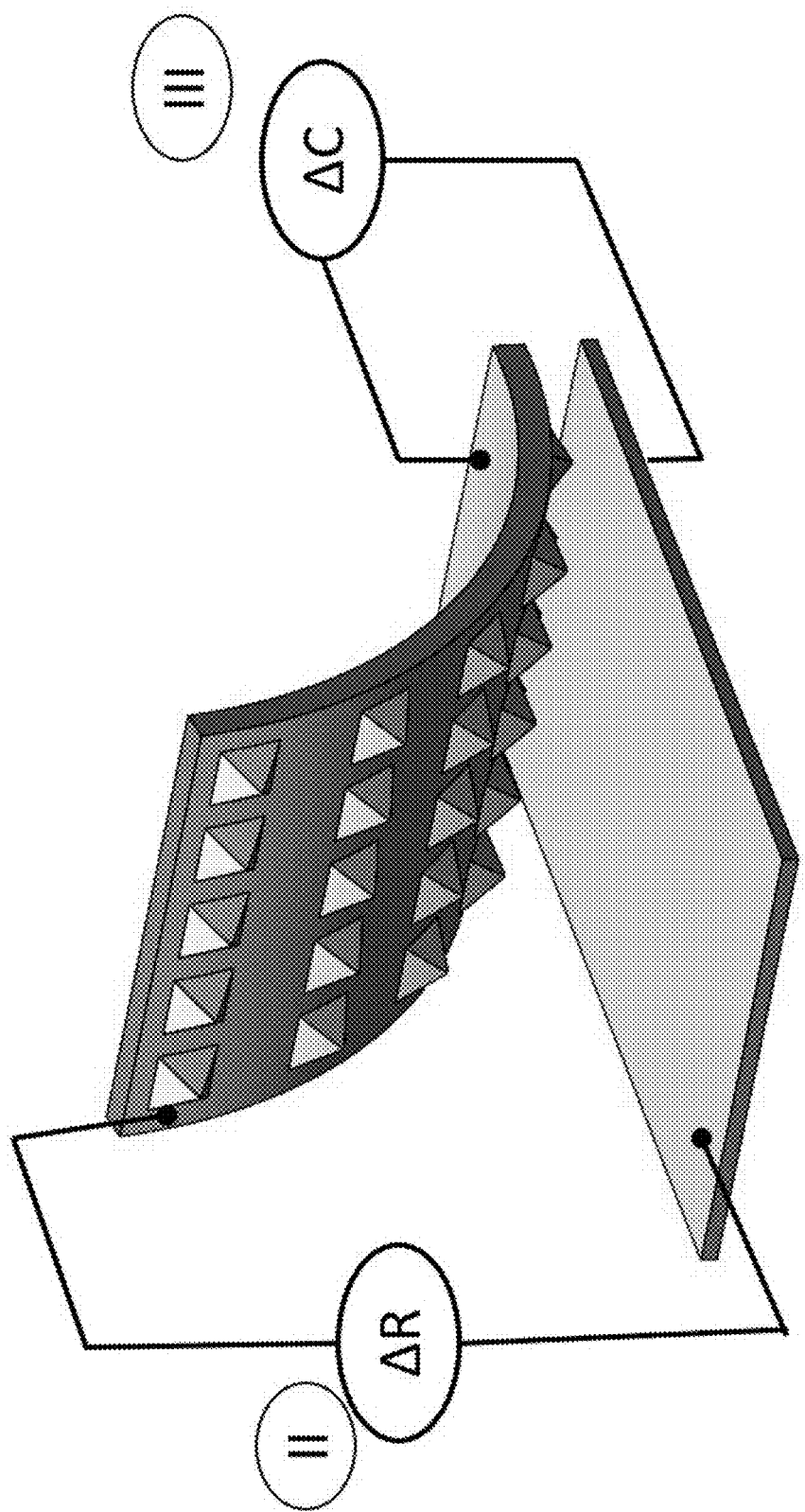

Embodiments provide inclusion of a strain gauge sensor (e.g., as shown in FIGS. 11A-11B) that can map out pressure in a plane parallel (alternatively, in a plane, line, curve, or other shape that is parallel, tangent, oblique, perpendicular, or at an angle) to the skin. Certain embodiments provide enhanced performance for applications including but not limited to vein finding for optimum sensor placement.

Over the past decade, research in the field of ultra-sensitive pressure sensors have seen an upsurge. This is due to their potential applications in wearable and flexible electronic sensors for motion detection, biomedical monitoring, human-machine interaction, and also artificial intelligence-assisted tactile sensing. Depending on the eventual application, the pressure ranges in which the sensor operates are categorized into four regimes: ultra-low pressure (<1 Pa), subtle-pressure (1 Pa-1 kPa), low-pressure (1-10 kPa), and medium-pressure (10-100 kPa). Of all these categories, significant attention has been paid to the subtle-pressure regime because of its importance in development of electronic skin (e-skin), touch screen devices, and the non-invasive detection of weak human physiological signals such as blood pressure and pulse wave detection on the wrist. Different successful schemes such as piezo-resistive, capacitive, piezo-electric, and triboelectric have been reported. Specifically, piezo-resistive sensors have drawn much attention because of their fast response, broad detection range, simple structure, and the simplicity of their signal measuring system.

In recent years, various structures and sensing materials have been proposed to achieve highly sensitive piezo-resistive pressure sensors, including paper based methods, that are promising. One of the popular sensor platforms is based on elastomers, such as conductive polymeric films, or composites with distinct structural schemes such as micro-pyramids, micro-domes, micro-pillars, and micro-cones. However, the lack of design rules for the fabrication of these microstructures inhibits the achievement of the highest sensitivity in a lowest footprint area. Although there have been successful piezo-resistive pressure sensors, achieving high levels of the sensitivity to detect human pulse wave, sound wave, or subtle pressure changes caused by object manipulation are still challenging. In almost all cases, the output of the sensors when measuring weak physiological signals, such as a pulse from the wrist, are in range of nanoamps (nA). Due to limitations in related art technology, researchers often utilize source meters or equivalent signal acquisition devices, which are typically desktop-sized devices, to generate a useful response of the piezo-resistive sensors for these applications. The usage of such devices as an overlooked necessary amendment of these pressure sensors greatly inhibits wearability, which is frequently claimed or cited as desirable.

A plurality of patterned micro-pyramids can be arranged on one side of a porous polymer and MWCNT composite-based dielectric layer and have an average pyramid angle (as depicted by "α" in FIG. 6A) of, for example, between 50 and 60 degrees. The plurality of patterned micro-pyramids can have an average size of micro-pyramids (as depicted by "ℓ" in FIG. 6A) of, for example, 150 μm or less.

Embodiments of the subject invention provide advantageous microstructure geometric parameters and spatial configuration to achieve high sensitivity and signal levels, so that the need for complex and non-portable measuring devices, including but not limited to source meters, is reduced or eliminated. A higher signal level is especially desired since it increases the signal-to-noise ratio, which allows for an improved signal acquisition for the sensor with less complicated or simple electrical circuitry. A high enough signal-to-noise ratio can allow straightforward signal amplification, which is an advantageous step for the detection of weak physiological human signals (e.g., pulse waveform from the wrist) using miniaturized and inexpensive circuits that can be integrated to wearable platforms.

When ranges are used herein, such as for dose ranges, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Example 1—a Low-Cost Approach to Fabricating a Sensitive CPS Based on Porous Polydimethylsiloxane (PDMS) Polymer and Multiwall Carbon Nanotubes (MWCNTs) Composite (PCNT) Using the Sacrificial Template Method The porous dielectric layer provided in certain embodiments of the subject invention shows excellent mechanical compressibility and flexibility suitable for application in wearable pressure sensors. Embodiments also show a long-term cyclability and a very low-pressure detection limit. In this example a flexible pressure sensor is applied to monitor tactile pressure sensing, generating morse code, proximity sensor, and acquiring pulse waveform from the arterial wrist site, demonstrating the practicality, advantageous performance, and utility of this embodiment.

Figure 1:
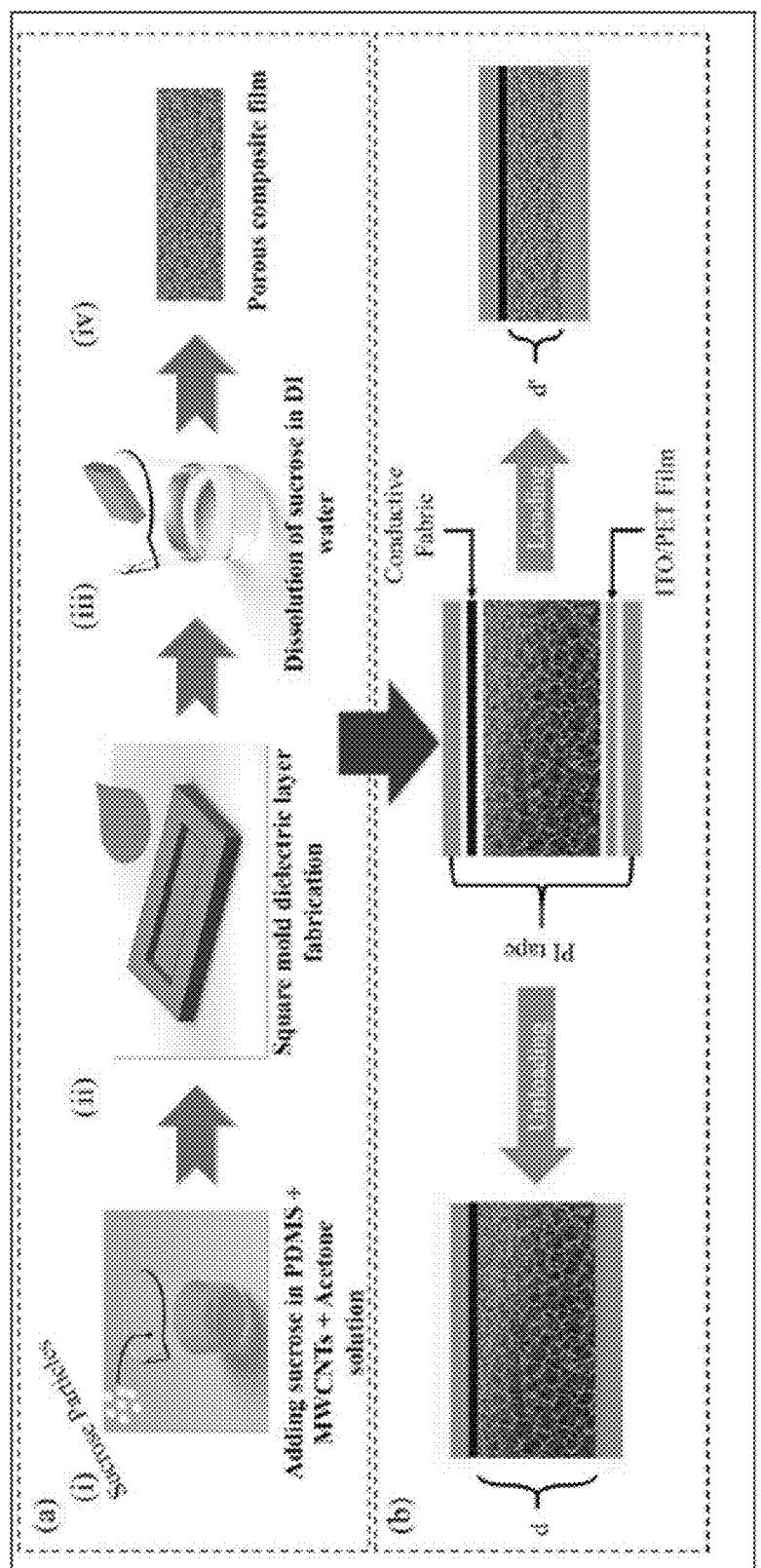
FIG. 1 shows a schematic illustration of the porous PDMS and MWCNTs composite fabrication process according to an embodiment of the subject invention.

Embodiments provide systems and methods for fabrication of a porous dielectric layer. FIG. 1 shows a schematic illustration of the porous PDMS and MWCNTs composite fabrication process according to an embodiment of the subject invention. Sucrose particles were used as the sacrificial template for creating porosity inside the polymer layer. The fabrication process in this embodiment comprised three steps. PDMS solution is prepared and then mixed with MWCNTs dispersed in acetone. After mixing the solution, sucrose particles are added to the mixture solution, as shown in FIG. 1a(i). The entire solution is cast on a glass mold to get the desired shape of the dielectric layer, as shown in FIG. 1a(ii). After curing the solution, the sucrose particles are dissolved in water under magnetic stirring, leaving a porous composite layer behind (FIG. 1a—iii, iv)). FIG. 1b shows the overall schematic of the sensor and the loading-unloading scenario of the sensor. Due to the presence of pores inside the dielectric layer, the air trapped inside leaves the pores leaving a compressed dielectric layer when pressure is applied.

Figure 2A:
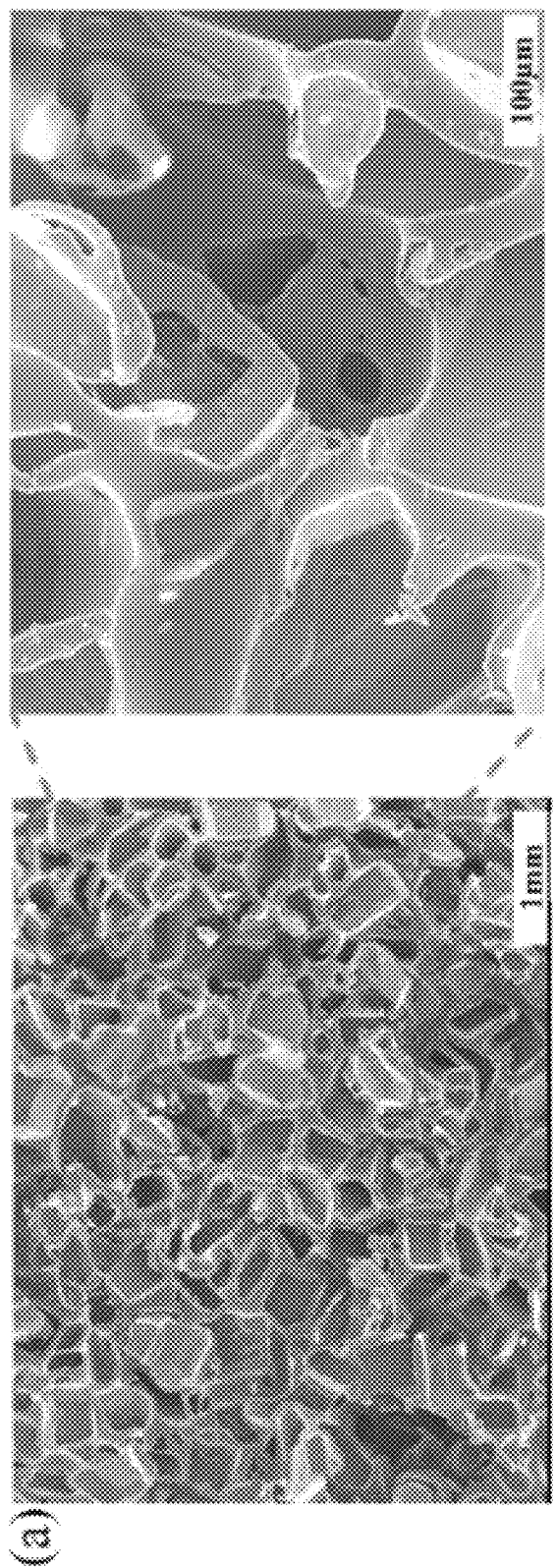
FIG. 2A shows scanning electron microscope (SEM) images at two different magnifications of a porous dielectric layer structure according to an embodiment of the subject invention.
Figure 2B:
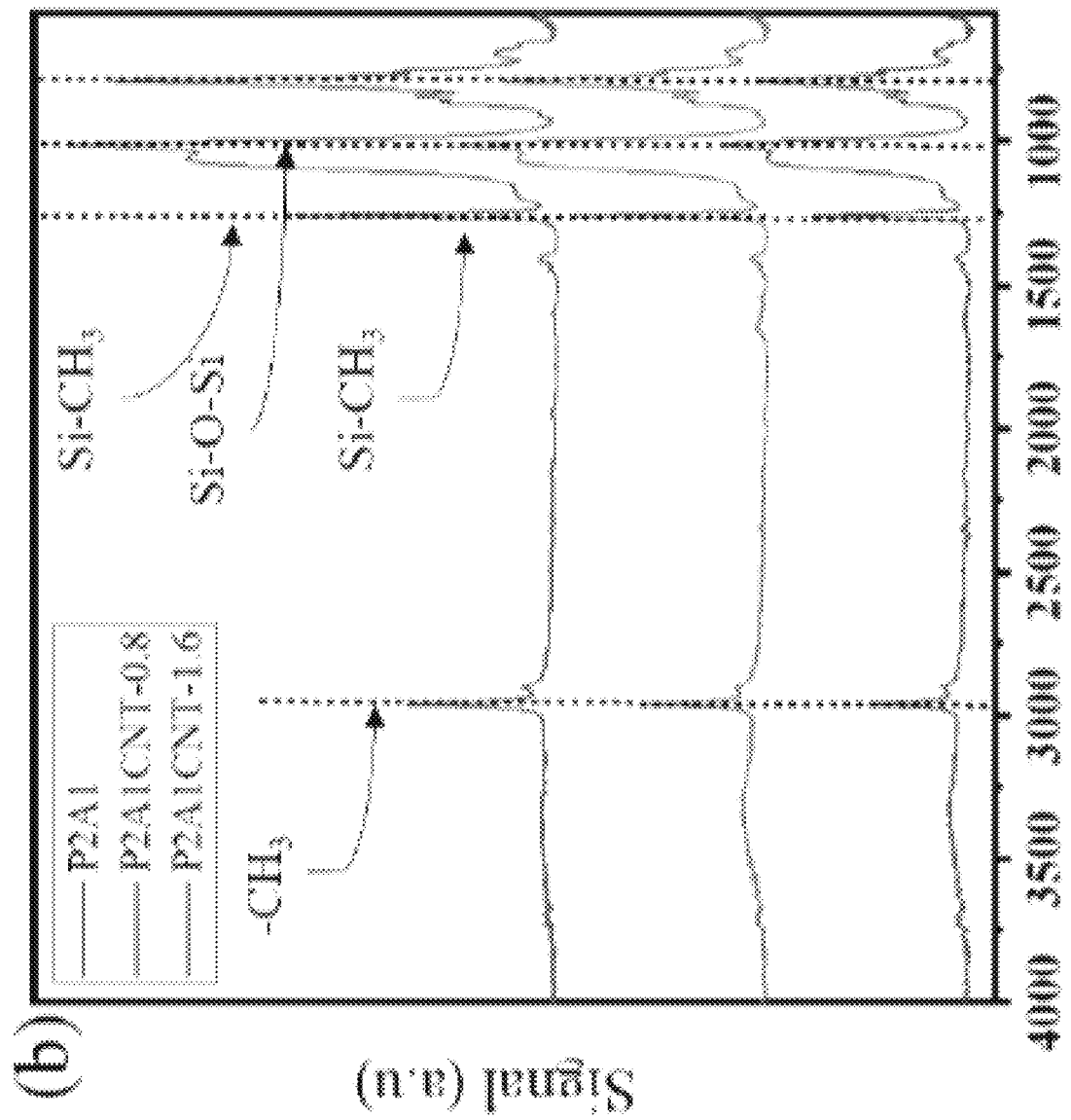
FIG. 2B shows the results of Fourier-transform infrared spectroscopy (FTIR) analyses of the PCNT with different MWCNT concentration according to an embodiment of the subject invention.
Figure 2C:
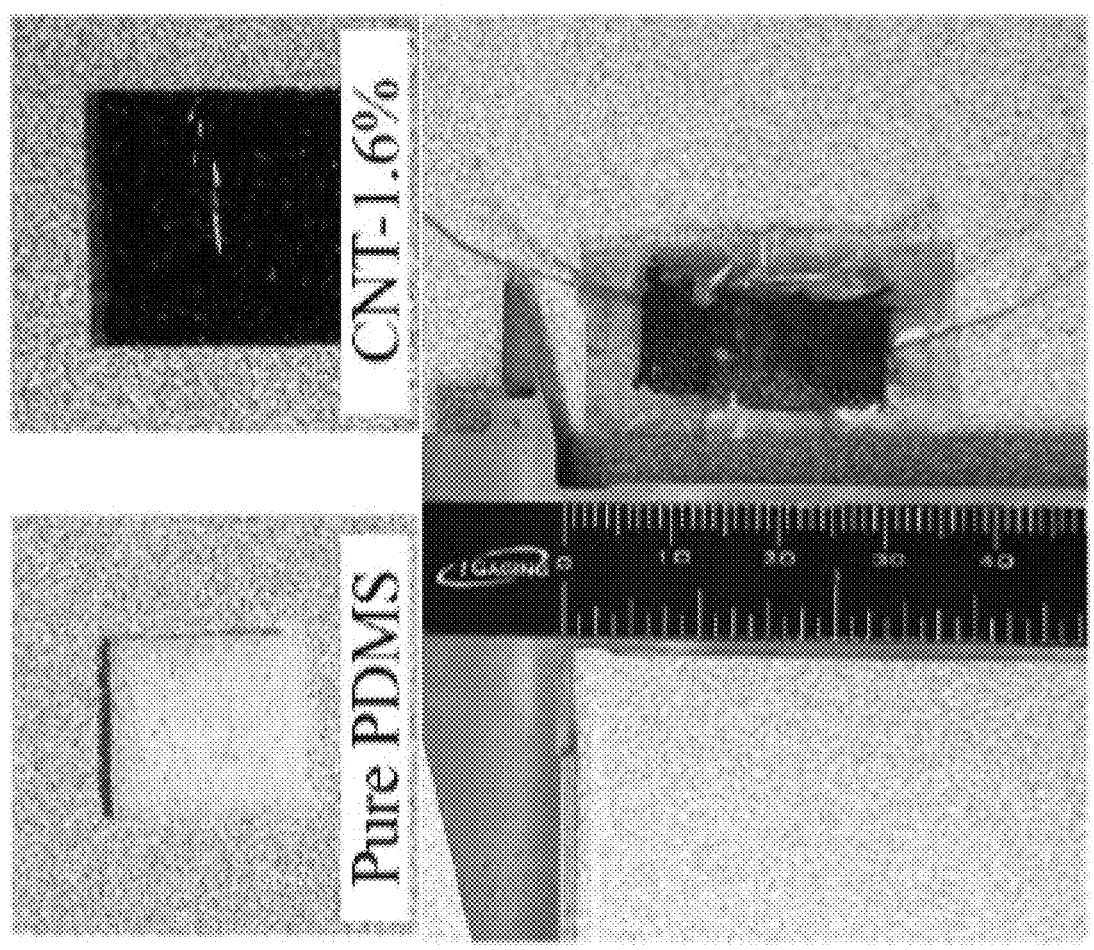
FIG. 2C shows photographs of porous PDMS with different MWCNT concentration and the fabricated sensor according to an embodiment of the subject invention. The composite polymer appears darker than the pure counterpart due to CNT inside the polymer matrix.

Embodiments provide systems and methods for materials characterization. FIG. 2A shows scanning electron microscope (SEM) images of the porous dielectric layer structure. As seen in the SEM images, the pores are randomly distributed throughout the entire volume of the porous dielectric layer. The pore size and volume can be controlled by changing the size of the sucrose particles and the number of sucrose particles during the fabrication. The presence of excessive pores can inhibit the mechanical behavior of the pressure sensor as well as reduce its performance. The sacrificial template's volume significantly affects the pore volume of the porous dielectric layer. Adding acetone to the PDMS increases the pore volume since the acetone evaporates during the curing process. The SEM images do not show residual sucrose particles inside the polymer matrix. Fourier-transform infrared spectroscopy (FTIR) analysis was carried out to characterize the interaction between the PDMS and MWCNTs composite, as shown in FIG. 2B. The peaks around 3000 cm$^{-1}$ correspond to the CH3 symmetric and asymmetric stretching. The peak around 1000 cm$^{-1}$ corresponds to the Si—O—Si bonding for both pure and composite polymers do not show any peak shift. With the addition of CNT (carbon nanotubes), the composite polymers do not form new chemical bonds relative to the pure PDMS components. The presence of the pores inside the polymer matrix results in excellent flexibility and compressibility of the dielectric layer. FIG. 2C shows photographs of pure PDMS and PCNT composites and the fabricated sensor. The composite polymer appears darker than the pure counterpart due to CNT inside the polymer matrix.

Embodiments of the subject invention provide systems and methods for electromechanical characterization of sensors and constituent materials. The pressure-sensing mechanism of the CPS can be explained with the help of the parallel plate capacitor mechanism. According to the parallel plate mechanism model, the capacitance depends on the distance (d) between the parallel plates, the electrode area (A), and the dielectric permittivity ($\varepsilon$). The initial capacitance before applying any pressure on the capacitive sensor is $$C = \frac{\varepsilon A}{d}.$$

Once pressure is applied, the capacitance changes due to the change in the distance between the electrodes as well as the dielectric permittivity changes. Therefore, the new capacitance under pressure becomes C+$\Delta$C=($\varepsilon$+$\Delta\varepsilon$)$^A$/(d−$\Delta$d) As more pressure is applied, the dielectric permittivity increases due to the gradual replacement of air ($\varepsilon$=1) with a higher dielectric constant PDMS/MWCNTs composite.

Figure 3A:
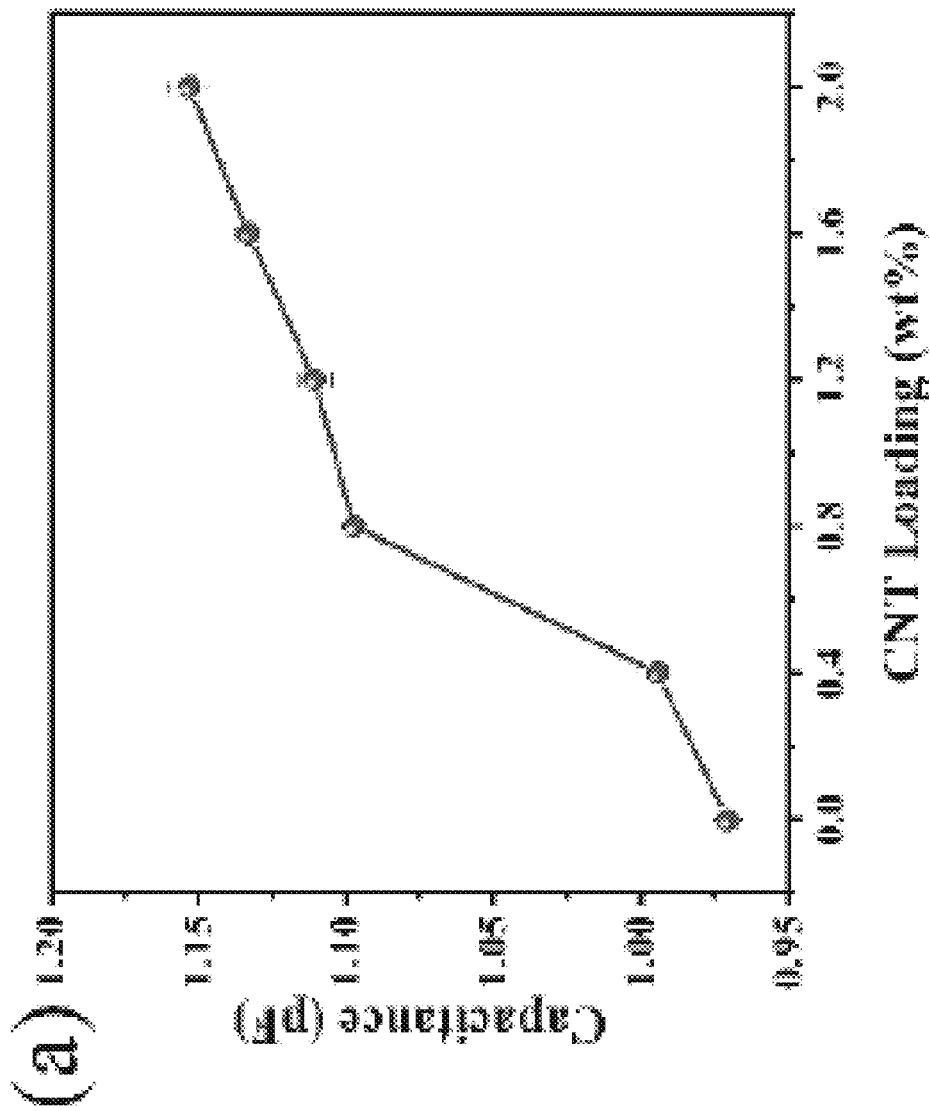
FIGS. 3A-3F, respectively, illustrate aspects of an electromechanical characterization of the PCNT-based pressure sensor according to an embodiment of the subject invention.
Figure 3B:
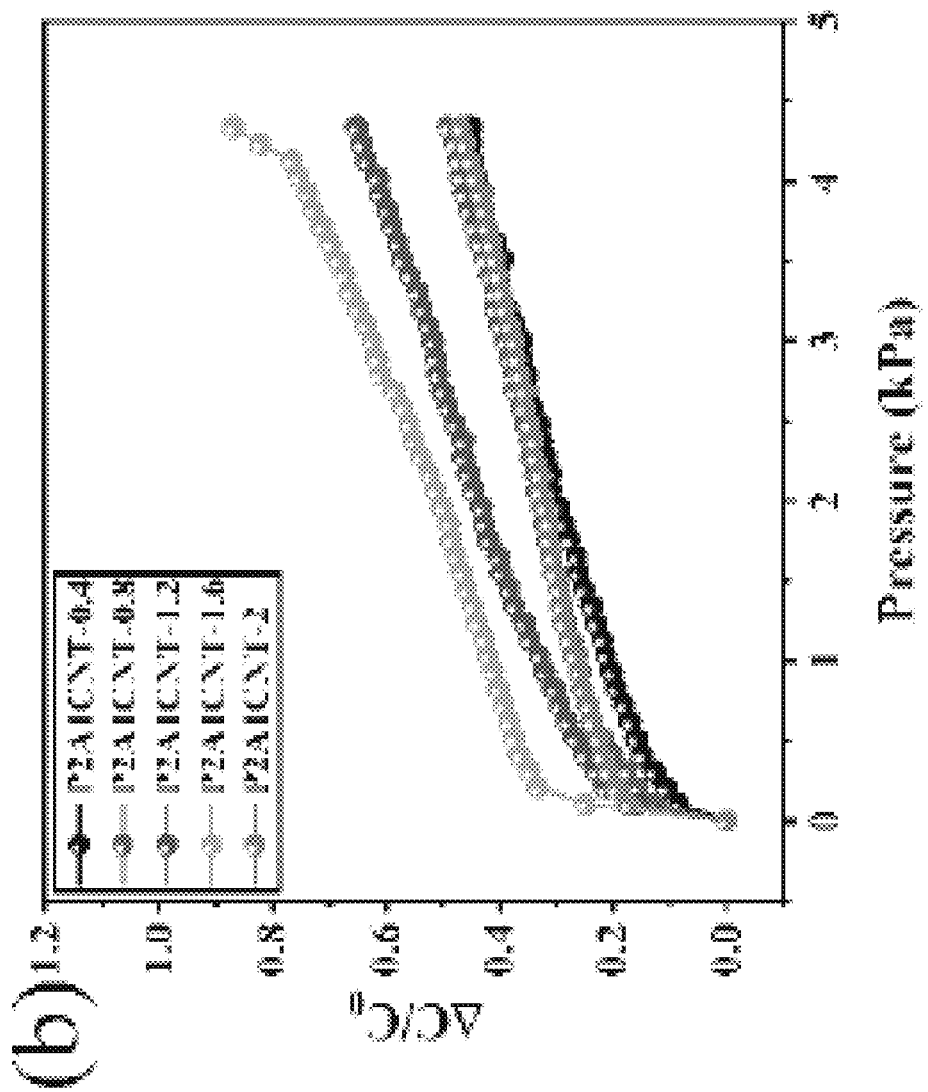
Figure 3C:
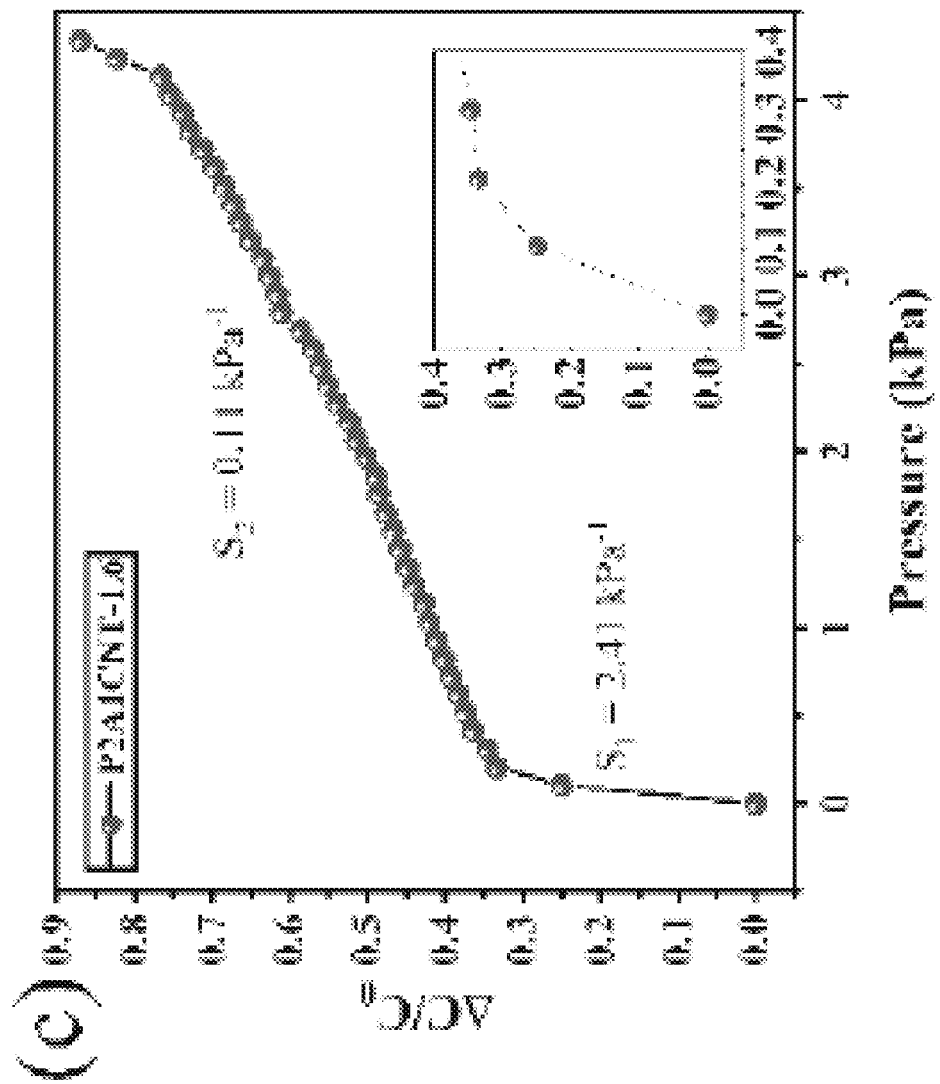
Figure 3D:
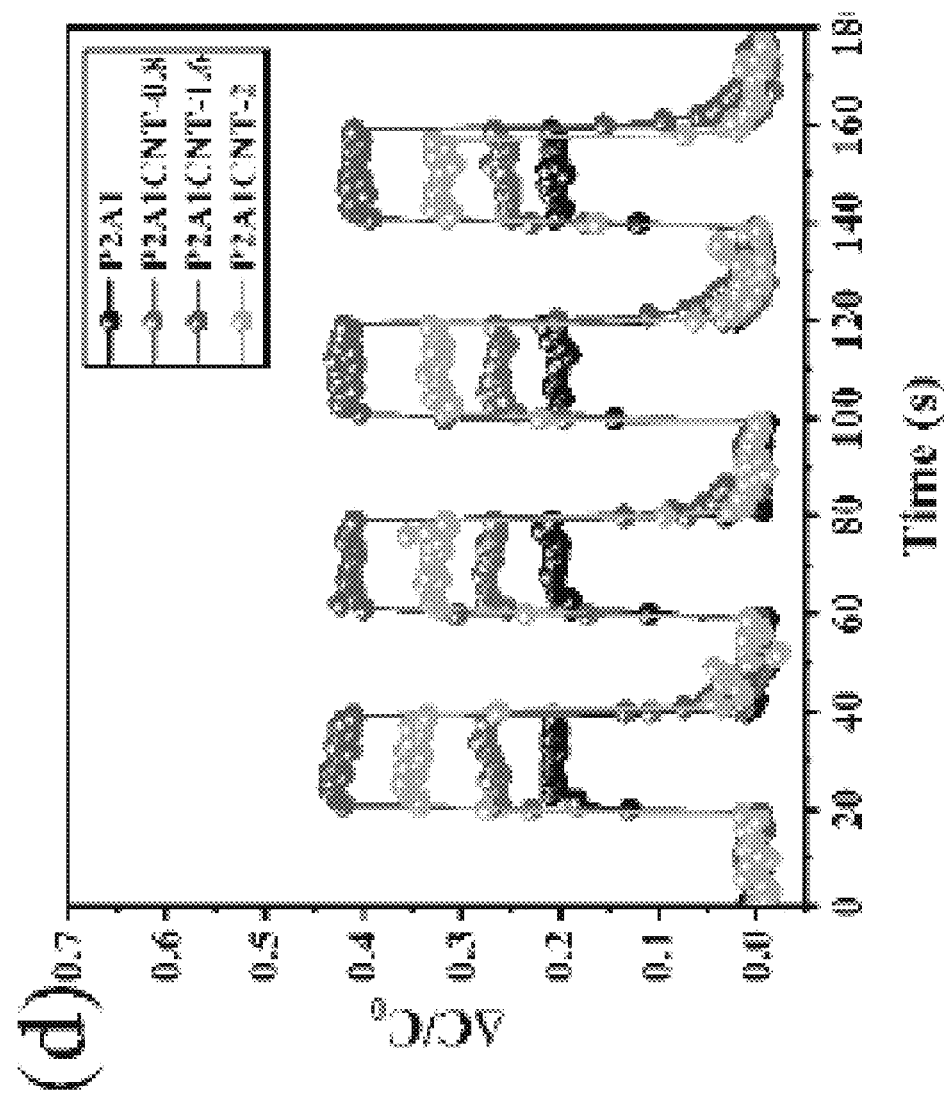

FIGS. 3A-3F show the electromechanical performances of the CPS based on porous PDMS/MWCNTs composite. The pressure sensing performance was characterized by plotting the relative change in capacitance vs. the external pressure. FIG. 3A shows the sensor's base capacitance ($C_0$) as a function of the MWCNTs concentration loading weight percentage. For statistical analysis, multiple sensors were measured for base capacitance calculation with the same MWCNT concentration at a frequency of 1 kHz and voltage of 1V. Then the base capacitance ($C_0$) was plotted as a function of MWCNT concentration as the x-axis. The variations of the base capacitance for different sensors with different MWCNTs concentration is shown in FIG. 3B. As the filler concentration increases, the base capacitance of the sensor increases due to the high dielectric constant of the material. The enhancement in dielectric constant happens due to dipole formation and micro capacitors network formation. Therefore, the dielectric permittivity increases. Since the capacitance is directly proportional to the dielectric permittivity of the sensor, the base capacitance increases. FIGS. 3B-3C show the pressure sensing performance of the sensors with different filler concentrations. The pressure sensitivity for a CPS is defined as $$S = \frac{\Delta C/C_o}{\Delta P},$$

where $\Delta C/C_0$ is the relative capacitance change, and P is the applied pressure. The figures show that the pressure sensitivity increases with the addition of MWCNT with the PDMS. The highest sensitivity was obtained from the sensor having 1.6% MWCNT with a high-pressure sensitivity of 2.41 kPa$^{-1}$ under 0.5 kPa, and 0.11 kPa$^{-1}$ beyond 0.5 kPa. In comparison, the pressure sensor with no MWCNT achieved a sensitivity of 0.31 kPa$^{-1}$. The initial high sensitivity can be explained by considering the initial high volume of the pore size inside the dielectric layer. Therefore, a small force can generate enough deformation in the porous dielectric layer in the low-pressure range. As a result, a high capacitance signal can be achieved. As the pores collapse quickly, leaving high dielectric constant elastomer upon compression, the pressure sensitivity decreases. The pressure sensitivity increases with the addition of MWCNT up to 1.6%, after which the pressure sensitivity decreases (FIG. 3B). The reduction in pressure sensitivity can be discussed with the help of FIG. 3A. With the addition of MWCNT with the PDMS, the base capacitance increases. At the same time, the capacitance signal under compression ($\Delta C$) also increases. However, since the pressure sensitivity is calculated by relative capacitance, the $\Delta C/C_0$ increases first. It then decreases because the $\Delta C$ cannot keep up significantly enough with the base capacitance $C_0$ to enhance the pressure sensitivity further. Therefore, the highest sensitivity was obtained for the sensor with 1.6 (wt. %) MWCNTs to the PDMS polymer solution (FIG. 3C). To further show the capacitance response of the sensors with different MWCNTs concentrations, the samples were cycled at 1 kPa. FIG. 3D shows the capacitance signal of samples having 0%, 0.8%, 1.6%, and 2% concentration of MWCNTs. The results show that the sensor having a 1.6% concentration of MWCNTs could achieve the highest $\Delta C/C_0$. This result is in accordance with FIG. 3B, where the plot shows the highest sensitivity comes from the sensor having 1.6% of MWCNTs.

Figure 3E:
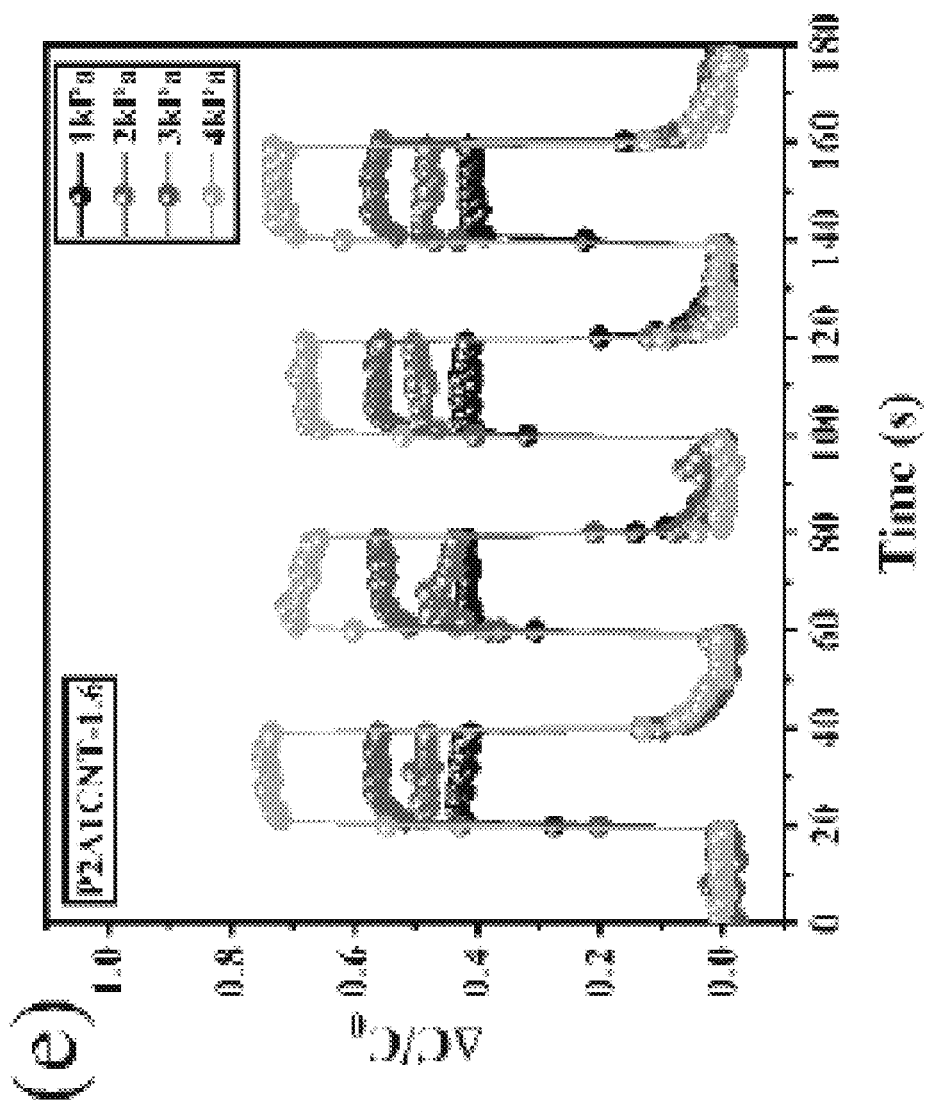
Figure 3F:
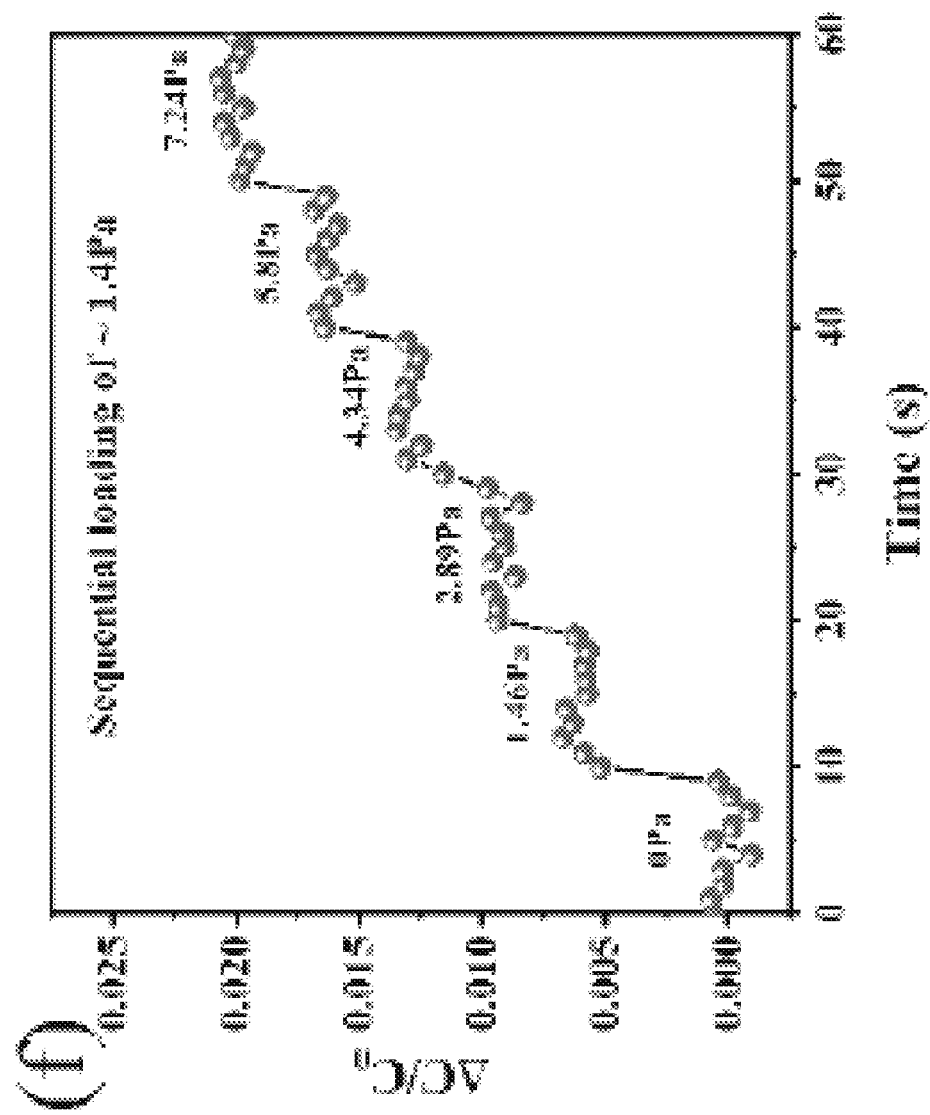

As a result, the sensor with 1.6% MWCNTs composite was chosen for further electromechanical characterization. FIG. 3E shows the loading-unloading profile for the PCNT-1.6 sensor under different pressure. The sensor's response at different pressure shows the sensor can detect different pressure levels with adequate change in $\Delta C/C_0$. The sensor was also evaluated to detect ultralow pressure, as shown in FIG. 3F. The sensor was loaded with sequential loading of different masses to apply an approximate pressure of 1.4 Pa, which is equivalent to a mass of 69 mg (about twice the weight of a grain of rice) on the sensor surface area (2.2×2.2 cm2). As seen from FIG. 3F, the sensor can effectively detect the sequential loading of 1.4 Pa of pressure with a cumulative sum of 7.24 Pa. Therefore, the provided sensor's limit of detection (LoD) was determined to be 1.46 Pa. Table 1 compares recent studies with porous dielectric layer-based sensing mechanisms. The provided PCNT-based pressure sensor achieved higher sensitivity in both low-pressure and high-pressure regimes.

Figure 4A:
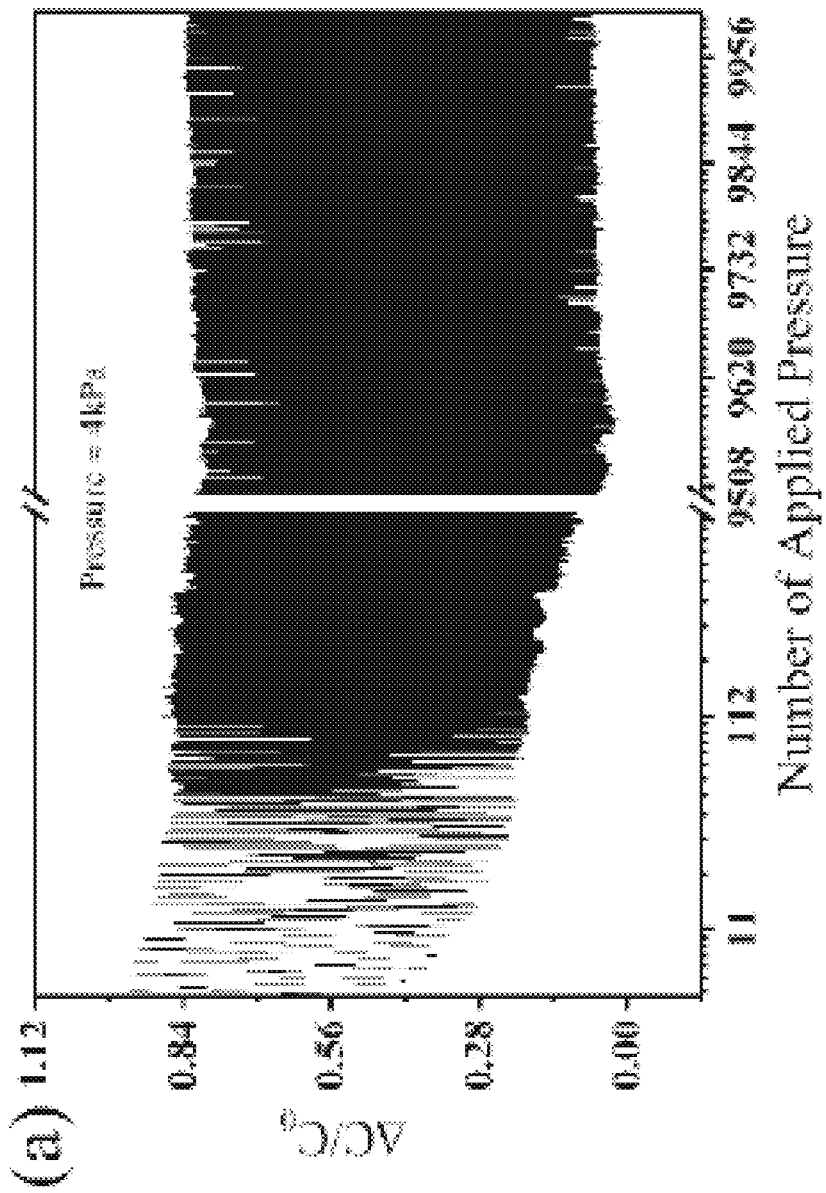
FIGS. 4A-4D, respectively, illustrate aspects of functional characterization of the PCNT-based pressure sensor according to an embodiment of the subject invention.
Figure 4B:
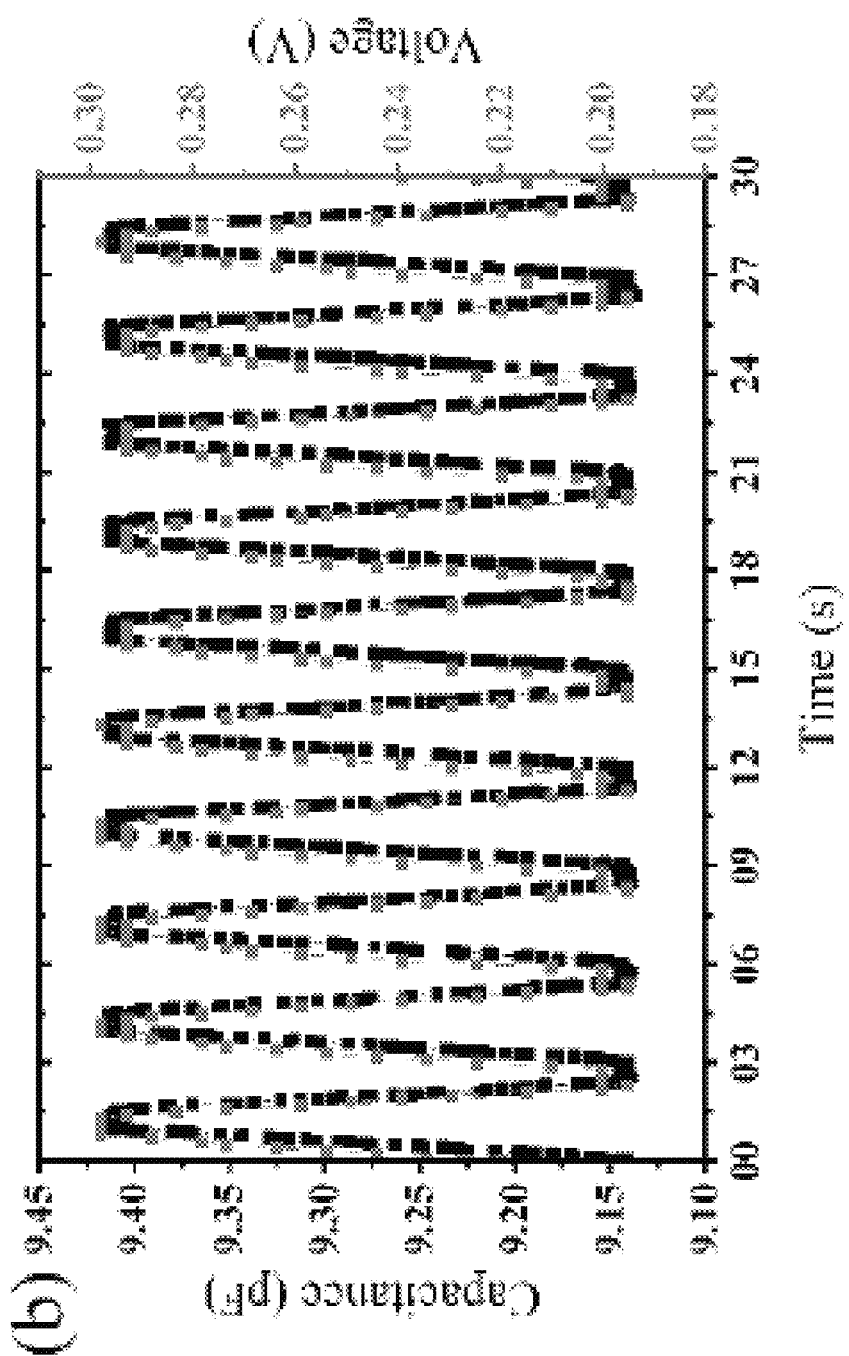
Figure 4C:
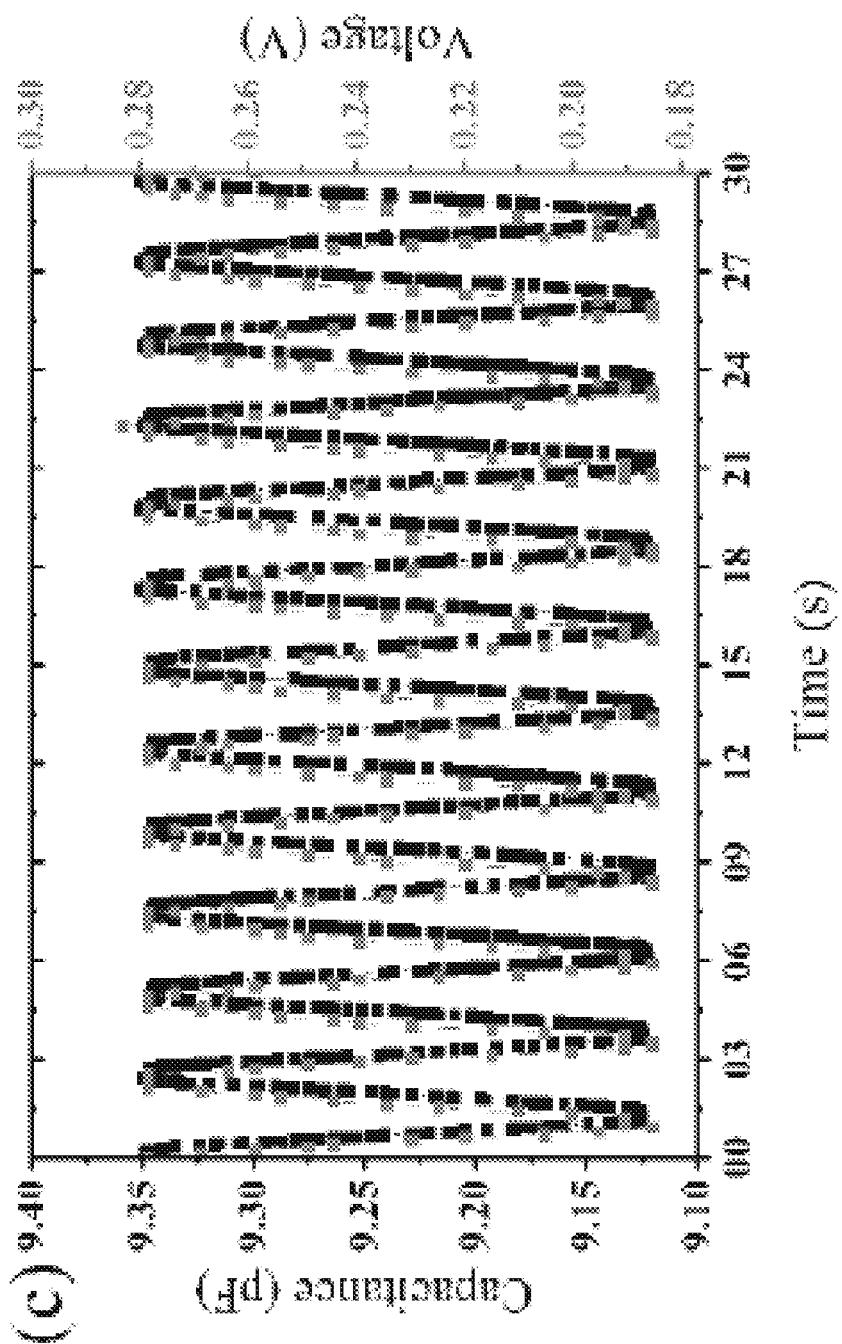
Figure 4D:
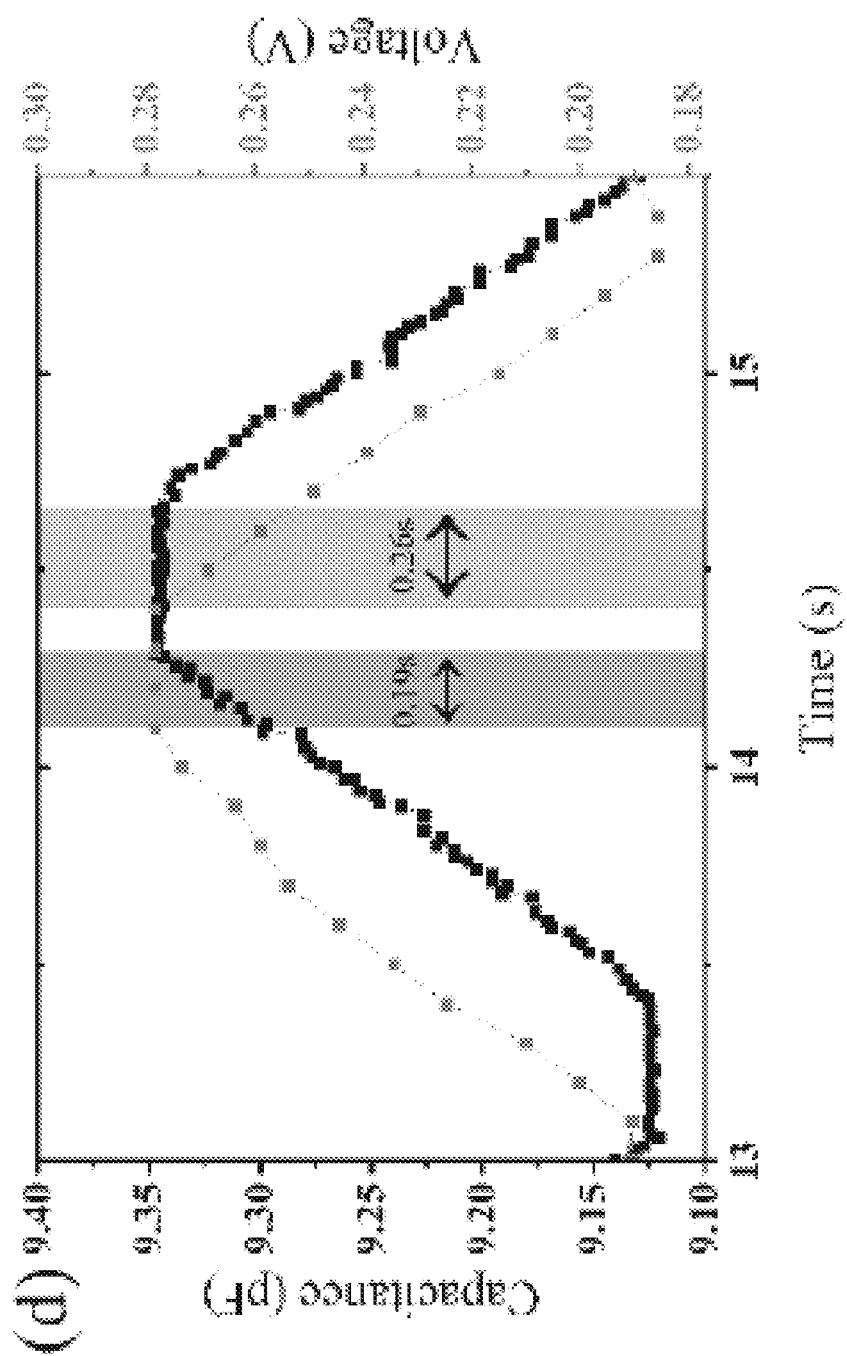

To show the reliability of the fabricated pressure sensor, the sensor was cycled 10000 times, as shown in FIG. 4A. The plot shows that the initial and final cycles are stable without significant performance degradation. The cyclic tests show the pressure sensor's excellent stability, proving its long-term function. Additionally, the pressure sensor was compared with a commercial piezoresistive pressure sensor. FIGS. 4B and 4C show the sensor performance of both sensors. Both sensors were tested on the same test bed that can produce a triangular loading profile with varying frequencies. In both profiles, the CPS can maintain a linear shape during the profile's rise time and fall time. However, the CPC signal is lagging with respect to the piezoresistive pressure sensor. FIG. 4D shows an enlarged profile image to show how much the CPS lags, with respect to the piezoresistive pressure sensor. During the signal's rise time, there is a delay of 0.19 s between the capacitive and piezoresistive signals. The delay time increases during the fall time of the sensor. This can be explained by the sensing mechanism of the CPS. The CPS relies on the parallel plate sensing mechanism.

As the sensor is compressed, the dielectric layer is compressed, leading to the capacitive response. As the pressure is removed, the dielectric material returns to its initial state. However, the polymer material has some viscoelastic effect that is prominent in the solid polymer dielectric layer. The viscoelasticity is reduced with the presence of the pores inside the dielectric layer as the air has negligent viscoelasticity. As a result, the viscoelasticity is reduced significantly for the porous polymer layer. Due to the presence of the viscoelasticity, the dielectric material takes some time to catch up. Therefore, the delay time is increased during fall time.

Figure 5A:
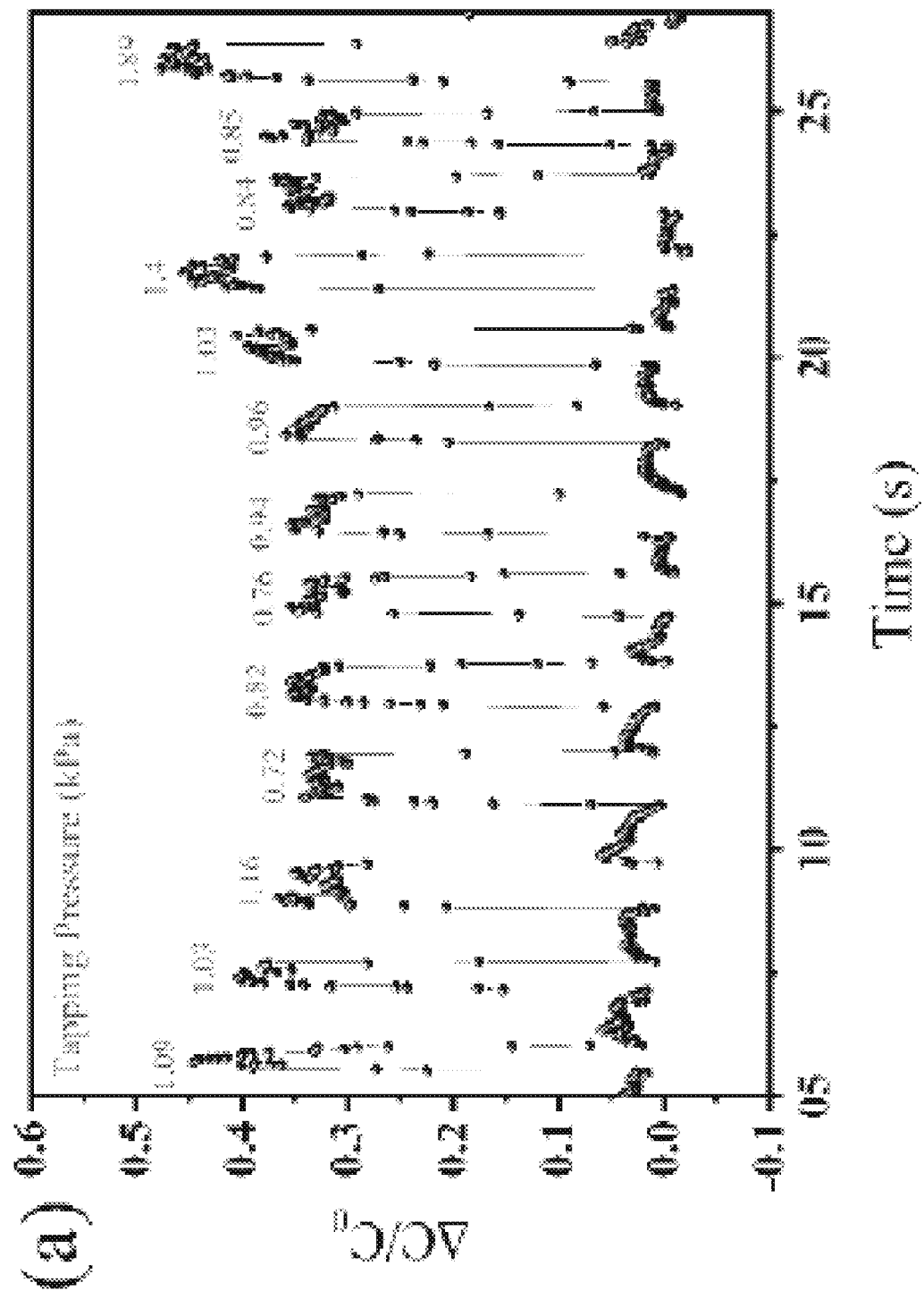
FIGS. 5A-5D show application of a PCNT-based sensor for real time pressure monitoring according to an embodiment of the subject invention.
Figure 5B:
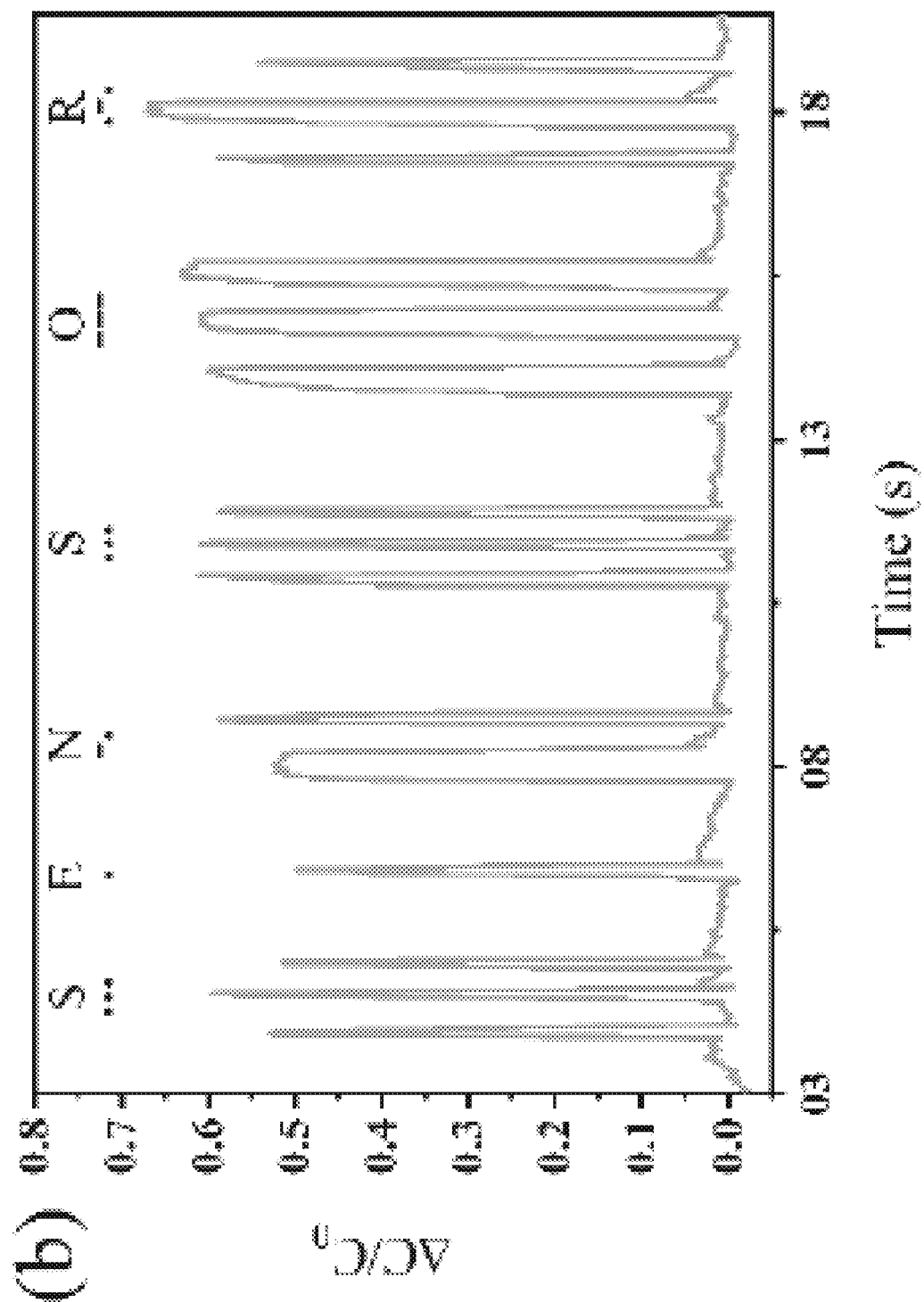
Figure 5C:
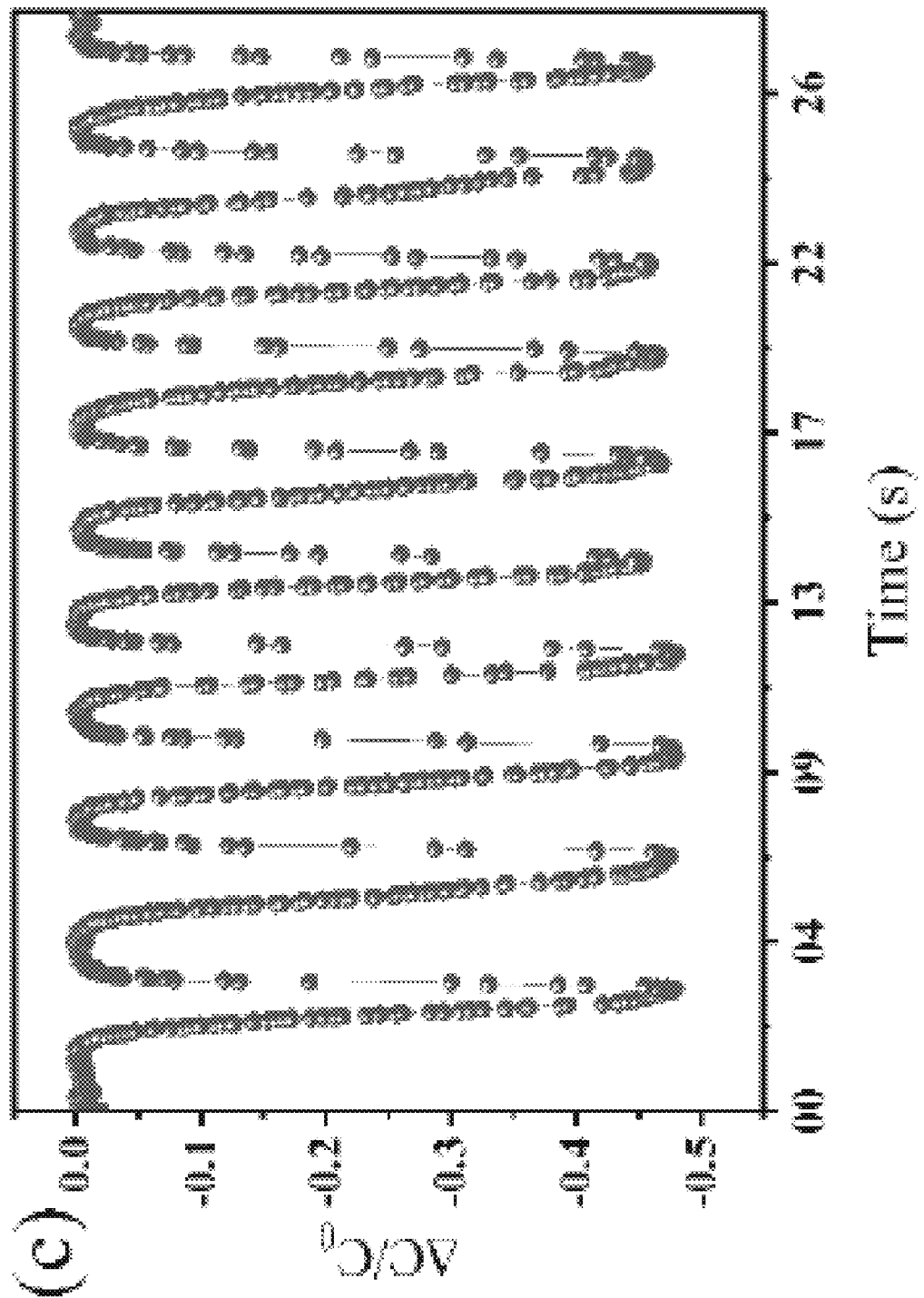
Figure 5D:
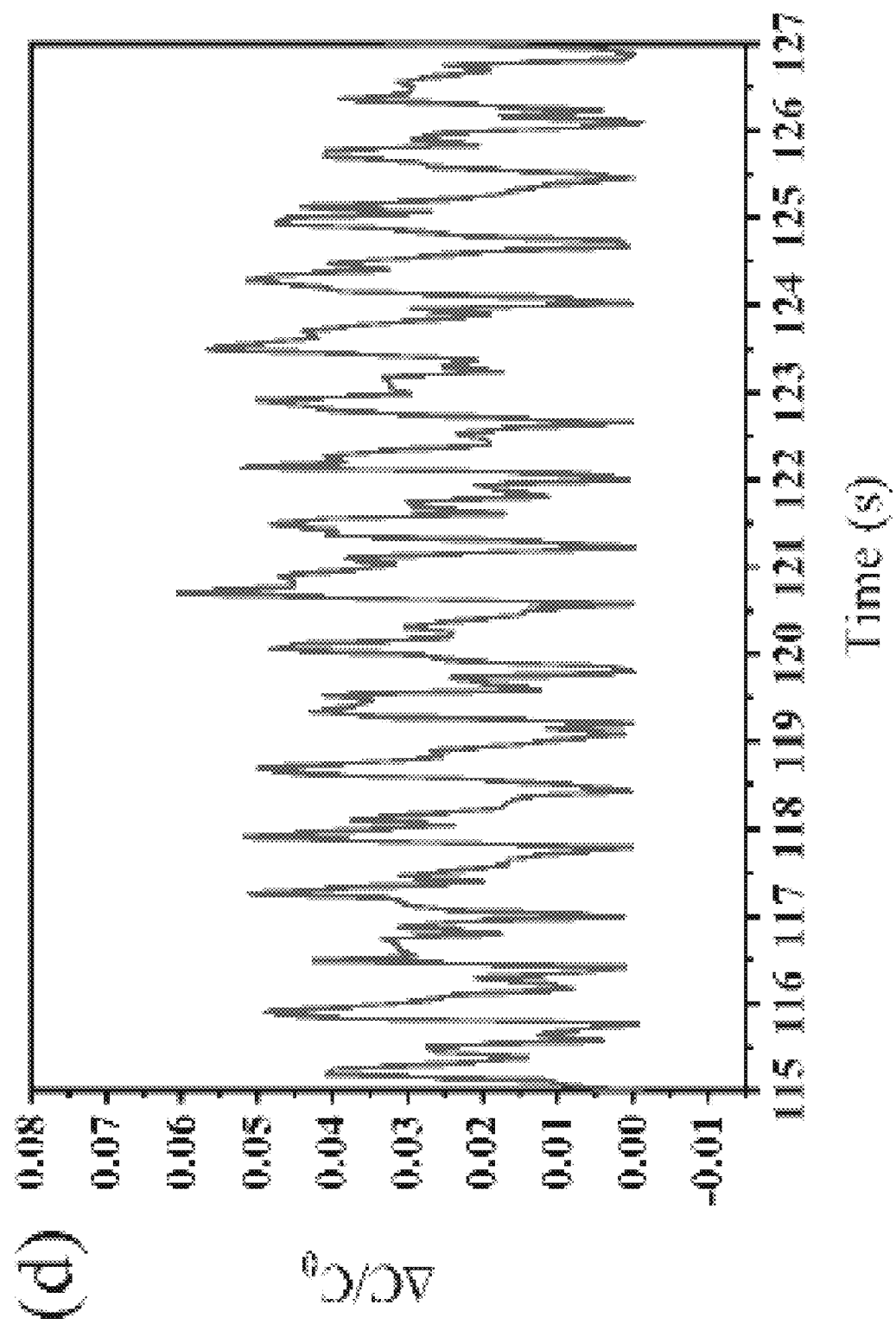

An embodiment comprising a sensor was evaluated for different real-time applications to demonstrate its outstanding performance. Due to high-pressure sensitivity and excellent stability, the pressure sensor has potential utility in tactile, physiological, and proximity sensing applications. Tactile sensing is essential for numerous applications, including prosthetics, diagnosis of Parkinson's disease, robotic hands, electronic skin, and many more. FIG. 5A shows low-frequency tactile pressure monitoring. In order to measure pressure variations during tactile sensing and monitor the corresponding sensor output, the sensor was placed on a digital weight scale (CS 200) to gauge the load caused by the pressing force, while being tapped at irregular intervals. A pressure variation of 0.7 kPa to 1.8 kPa was applied to the sensor. The figure shows that the sensor has a fast response to the tactile pressure and the variance in the signal corresponding to the light and heavy tapping. Due to the fast tactile response of the sensor, the sensor can be employed for generating Morse code from finger knocking, diagnosis of Parkinson's disease, etc. For instance, FIG. 5B shows a Morse code application of the pressure sensor. Using the Morse code technique, the sensor was tapped to represent different English words. Morse code is generated using short marks (dots) and long marks (dashes). The practical application of such a device can be in a hospital setting where paralyzed patients can express their thoughts and feelings using Morse code. A unique feature of CPS is the ability to detect proximity. The proximity effect is due to the disturbance of the electric field lines when a conductive or dielectric material (e.g., a human finger) comes near a capacitive sensor that decreases the capacitance. The provided CPS shows excellent proximity sensing that can be useful for hands-free application (FIG. 5C). As depicted in FIG. 5C, the relative capacitance decreases by 0.5 when a human finger approaches the CPS.

The proximity effect range was determined by using a scale and by moving the handout from the proximity of CPS. The fabricated sensor has a proximity detection range of 12 inches and can effectively detect any conductive object within this range, which is very suitable for such applications. Due to the surge in the COVID-19 situation and to ensure public safety from spreading disease via touch, automatic applications such as automatic disinfection dispensers, automatic soap dispensers, automatic water faucets, automatic door handles, and many more applications can benefit from such proximity sensing technique.

Finally, the high sensitivity of certain embodiments is also advantageous for getting physiological information such as pulse waveforms collection from the wrist arterial artery. To get the pulse waveforms from the wrist artery, the sensor was attached on top of the wrist artery conformably using a bandage. The data was collected from a 30-year-old healthy male volunteer under normal conditions. The pulse rate obtained from the wrist artery shows a pulse rate of 85 beats per minute. Pulse waveforms carry numerous information about cardiovascular information. Continuous monitoring of pulse waveforms can help early diagnosis of cardiovascular anomalies such as hypertension, arterial fibrosis, and arrhythmia and detect pregnancy. The pulse waveforms show three distinct peaks characterized by the systolic peak, diastolic peak, and percussion response from the peripheral arteries.

Embodiments of the subject invention provide straightforward and cost-effective fabrication systems and methods to realize a sensitive, stable, and reliable porous PDMS-based pressure sensor functionalized by MWCNTs. The complete electromechanical characterization of the sensor shows a potential application in different fields, including tactile monitoring, Morse code application, physiological monitoring, and proximity sensing application. The high performance of certain embodiments of the pressure sensor comes from the synergistic effect of porous polymer and MWCNTs composite as the dielectric layer. The porosity improves the compressibility of the dielectric layer, and the addition of MWCNTs with the polymer improves the dielectric permittivity of the polymer. To improve the compressibility of the polymer, acetone was used as a polymer diluter that has an added influence on the compressibility improvement. The pressure sensitivity increases with the addition of the MWCNTs to the solution, and the highest sensitivity in certain embodiments was achieved by adding 1.6% of MWCNTs with the PDMS. Due to the ultrahigh-pressure sensitivity at the low-pressure regime, embodiments of the sensor have been shown to have an ultralow detection limit of 1.46 Pa and excellent stability of 10000 cycles, proving the pressure sensor's reliability for numerous applications. The pressure sensor's outstanding performance in certain embodiments allows tactile sensing detection and subtle pulse waveforms monitoring. Additionally, proximity sensing allows embodiments of the sensor to monitor object detection at a proximity range of 12 inches. Embodiments of the sensor can be employed for not only physiological monitoring applications but also hands-free applications that can improve the fight diseases.

Embodiments of the subject invention provide systems and methods for fabrication of porous PDMS. Polydimethylsiloxane (PDMS) has two components: a base and a curing agent. In this example the base and curing agents were mixed according to the 10:1 mixing ratio. MWCNTs were weighted as a percentage of weight to PDMS, added to acetone, and dispersed mechanically. The PDMS mixture and the MWCNTs solution in acetone were mixed until a homogeneous mixture solution was obtained. Finally, sucrose particles were added to the mixture solution. The volume ratio between PDMS, acetone, and sucrose particles was kept at 2:1:4 for all samples. The mixture solution was poured into a glass mold, and the solution was cured for 5 h at 70° C. After curing the polymer, the sucrose particles were dissolved in water, leaving a highly porous polymer behind.

Embodiments of the subject invention provide systems and methods for sensor fabrication. In this example the PCNT-based pressure sensor was fabricated with a layer-by-layer stacking process. The cured dielectric layer was cut into 1 cm×1 cm and placed on the conductive textile electrodes. Another conductive textile electrode was used to complete the sensor realization. Finally, the sensor was packaged inside polyimide tape.

The structure and morphology of the porous polymer were characterized by SEM (JSM-FS100). FTIR was conducted to characterize different concentration composite samples. The electromechanical characterization was conducted using a MARK-10 testbed connected to a MARK-10 M5-50 force gauge for precise loading. For applying uniform pressure on the sensor, a thin glass slide of 2.2 cm×2.2 cm was used between the force gauge and the sensor. The capacitance measurement was carried out in an LCR meter (Agilent 4263B) with an ac voltage of 1V at 1 KHz.

An evaluation board with capacitance to digital converter (AD7150) was used instead of an LCR meter for both wearable and proximity applications due to its more compact form and lightweight application allowance. The evaluation board can communicate with the computer using an I2C standard interface.

Example 2—Design Rules for a Wearable Micro-Fabricated Piezo-Resistive Pressure Sensor So far, several attempts of designing and optimization via the modelling of piezo-resistive pressure sensors have been made; however, they are all limited to the detection of gas pressure by incorporating a sensitive diaphragm. Currently, there has been no successful effort in the design optimization of contact piezo-resistive pressure sensors suitable for mounting on the skin to detect weak human physiological signals via a completely wearable setup. Therefore, in this example, the inventors used a finite element method (FEM) analysis to study the advantageous parameter values for microstructure shape, spatial configuration, and sensing material characteristics. Three dimensional (3D) simulations are advantageously applied for a realistic analysis of the effects that various micro-feature shapes have on piezo-resistive sensor sensitivity. Furthermore, the inventors investigated assigning different conductivity values to micropatterned elastomer to study the effects on the sensor's current output level and sensitivity. Finally, the design parameters of a micro-patterned sensor (e.g., a micro-pyramid) including spatial number density, size, and angle were analyzed in order to achieve the maximum sensitivity in the same footprint area.

A computational model of a piezo-resistive pressure sensor to simulate electrical output signal while the sensor undergoes compression was developed using COMSOL Multiphysics in order to solve the controlling partial differential equations by a finite element technique. The partial differential equations of physics are usually formulated either in a spatial coordinate system, with coordinate axes fixed in space, or in a material coordinate system following the material as it deforms. The former is often referred to as an Eulerian formulation, while the latter is a Lagrangian formulation.

In this study, a method called the Arbitrary Lagrangian-Eulerian (ALE) has been used for the following reason: because of the deformation associated with the micro-features during the sensor's operation, the map from mesh coordinates to spatial coordinates might get progressively ill-conditioned (a drawback of Lagrangian method). To avoid this, a remeshing operation (stopping the simulation and deleting the previous mesh and generating a new one) is needed to map all the quantities to a regular-shaped new mesh.

The method that allows rewriting the physics equations on a freely moving mesh leads to the ALE method. ALE represents an intermediate between Eulerian and Lagrangian depending on the characteristics of the study, combining the best features of both methods.

Figure 6A:
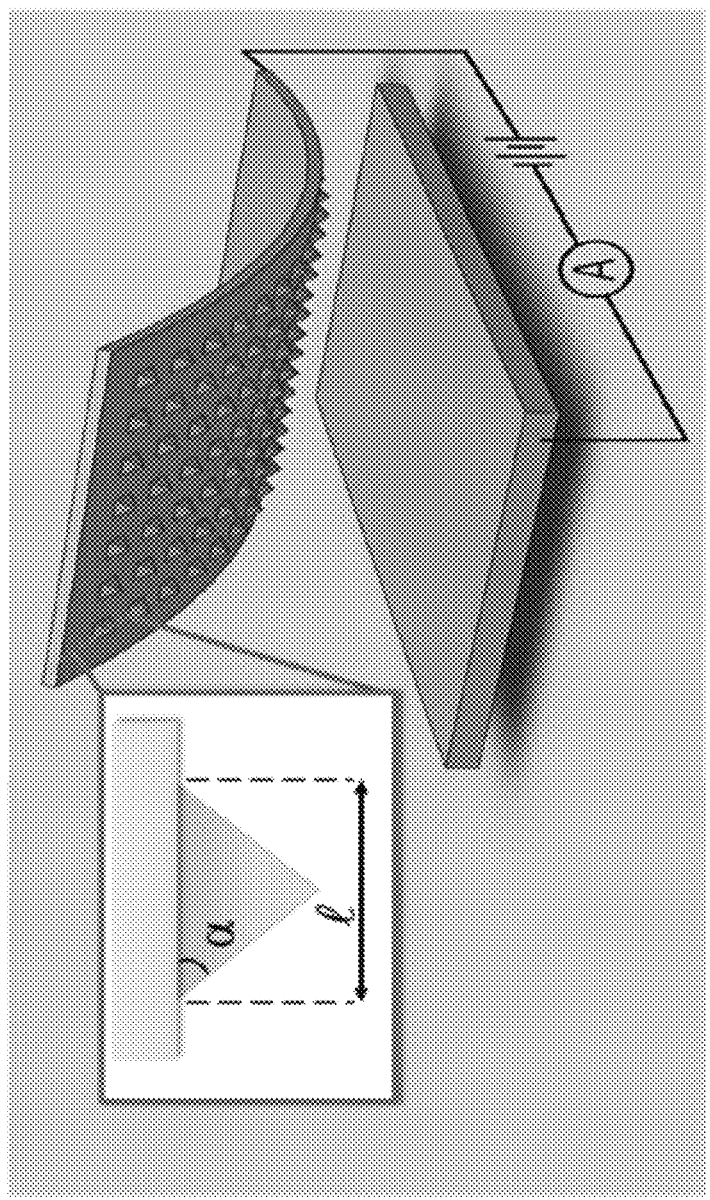
FIGS. 6A-6B show a piezo-resistive sensor design according to an embodiment of the subject invention.

This example considered steady state modeling to analyze the maximum signal level that the sensor is capable of outputting. A 3D-computational model of a square shaped pressure sensor is provided to simulate and study the micro-feature deformations due to pressure ranges experienced similarly to the pulse wave from the human wrist. This pressure was reported to range from 1 to 10 kPa depending on the test-subject's characteristics. The schematic design of a pressure sensor is shown in FIG. 6A. The sensor consists of a flexible hyperelastic micro-patterned layer and a conductive current collector layer both facing each other. Various micro-feature shapes, namely the micro-pyramid, micro-cone, micro-dome, and micro-pillar, were selected for the simulation based on the frequently reported microfabricated pressure sensors (FIG. 6B). 3D simulations were run to study the influence of various micro-feature shapes on the sensor's sensitivity (which is defined as relative current change vs. applied pressure). In addition, the dependence of the sensor response on the conductivity of the flexible polymeric layer and micro-feature geometric dimensions were evaluated using 3D and 2D modeling.

Structural contact in this study, which by default dictates geometric nonlinearity, was simulated using the Augmented Lagrangian method. This setting leads to more accurate results compared to the default penalty method. Also here, $E_{char}$ (generally equal to the young's modulus of the destination) was increased (×100) to account for strain nonlinearity of the polymer. Finally, a preset penalty factor tuned for stability was employed. Problems incorporating large overclosure or gap (e.g., such as the present study, where the boundaries at initial steps move toward each other until they establish contact) require tuning for stability.

For 3D simulations, free tetrahedral mesh type was chosen with calibration for general physics in "extremely fine" size. The type of the mesh was chosen based on a mesh quality test (measuring skewness to be near 1 which corresponds to regular shape) in order to avoid inverted mesh elements. The optimum size of the mesh was chosen based on the outcome of the convergence test. The general method for such a test was increasing the number of degrees of freedom (DOFs) associated with "extremely fine" mesh size setting to 1000% of its original value. If the results of the new study (current in amperes) varied more than 5% compared to the previous study, the convergence test would fail, and a new study with smaller mesh size would be proposed until it passed this convergence test.

Geometric parameters such as angle, base size, and spatial configuration for one of the frequently reported shapes in the literature (i.e., micro-pyramid), was chosen to optimize the micro-feature parameters. It should be noted that results obtained from such simulations were not exclusive to the micro-pyramid and could also be expanded to other micro-feature shapes. Specifically, 2D modeling was used to find the optimum angle ($\alpha$), base size ($\ell$) (FIG. 6A), and micro-feature number density (the number of micro-features per unit length) of the pressure sensor in order to achieve the most sensitivity.

The present study used COMSOL Multiphysics to deduct the design rules for a sensitive and wearable micro-fabricated piezo-resistive pressure sensor. COMSOL Electric Currents (ec) interface from the branch AC/DC>Electric Currents (ec), coupled with Solid Mechanics module, were used to solve the differential form of Maxwell's equations considering simulation parameters reported in Table 2.

TABLE 2

Simulation parameters.

| Parameter | Micro-Patterned Layer | Current Collector Layer | References |
|---|---|---|---|
| Feature Angle (a) | 57.4 degrees | N/A | [40] |
| Feature Base Size (l) | 100 µm | N/A | N/A |
| Feature Spacing | 300 µm | N/A | N/A |
| Array | 5 × 5 (low number density setup) | N/A | N/A |
| Footprint | 1.8 × 1.8 mm$^2$ | 1.8 × 1.8 mm$^2$ | N/A |
| Conductivity | 1 ×10$^5$ S/m | 46 ×10$^6$ S/m | |
| Young's modulus | 750 kPa | 70 GPa | [41, 42] |
| Poisson's ratio | 0.49 | 0.44 | [41, 42] |
| Density | 970 kg/m$^3$ | 19,300 kg/m$^3$ | [41, 42] |
| Relative Permittivity | 2.75 | 1 | |

In the FEM tool used in this study, models are described in terms of the partial differential equations for the underlying physical laws. Conservation of charge in the volume of the sensor dictates the rate at which the charge flows in/out of the sensor must be equal to the rate it increase/decreases inside the volume. This notion is mathematically expressed by equation of continuity as:

$$\nabla \cdot J = Q_{j,v} \quad (1)$$

where J is the current density, and $Q_{j,v}$ is electric charge density's 2nd order matrix. Also, the current density is calculated by equation below, $$J = \sigma E + J_e \quad (2)$$

where $\sigma$ is electric conductivity of the material (e.g., of sensing layer and the current collector layer), and E is the electric field strength, and $J_e$ is the current density of an externally generated current. As seen below, electric field strength (E) is a function of the electrical potential (V):

$$E = -\nabla V \quad (3)$$

These equations are solved by finite element method with numerically stable edge element discretization combined with solution of sparse equation system.

The provided sensor setup is made up of two layers. One layer is a flat conductive substrate as the current collector and the other layer is an elastomeric PDMS substrate studded with micro-features. The sensor comprised an array consisting of 5×5 of equally spaced micro-features, each having a footprint area equivalent to 100×100 µm². The total size of the sensor was designed to be 1.8×1.8 mm² in order to realistically model a pressure sensor that overlies on top of the radial artery, which was reported to have diameter of about 2.3 mm in human wrist area. The micro-featured layer is placed facing the current collector layer so that application of an external force causes the micro-features to deform and lead to an increase of the contact area between the layers (FIG. 6A). In this simulation, the formerly mentioned external forces are applied in such a way that each layer gets closer to the other at a rate of 0.5 micrometer per step. In a series of 24 steps, the layers are increasingly pushed against each other causing measurable deformations on the tip of the micro-features (i.e., contact point between the two layers). This deformation leads to decreases in electrical resistance between the layers. Now, when an electrical potential difference is applied between these two layers, the passing current bridging the layers varies depending on the amount of contact area change which is caused by externally applied pressure.

Figure 6B:
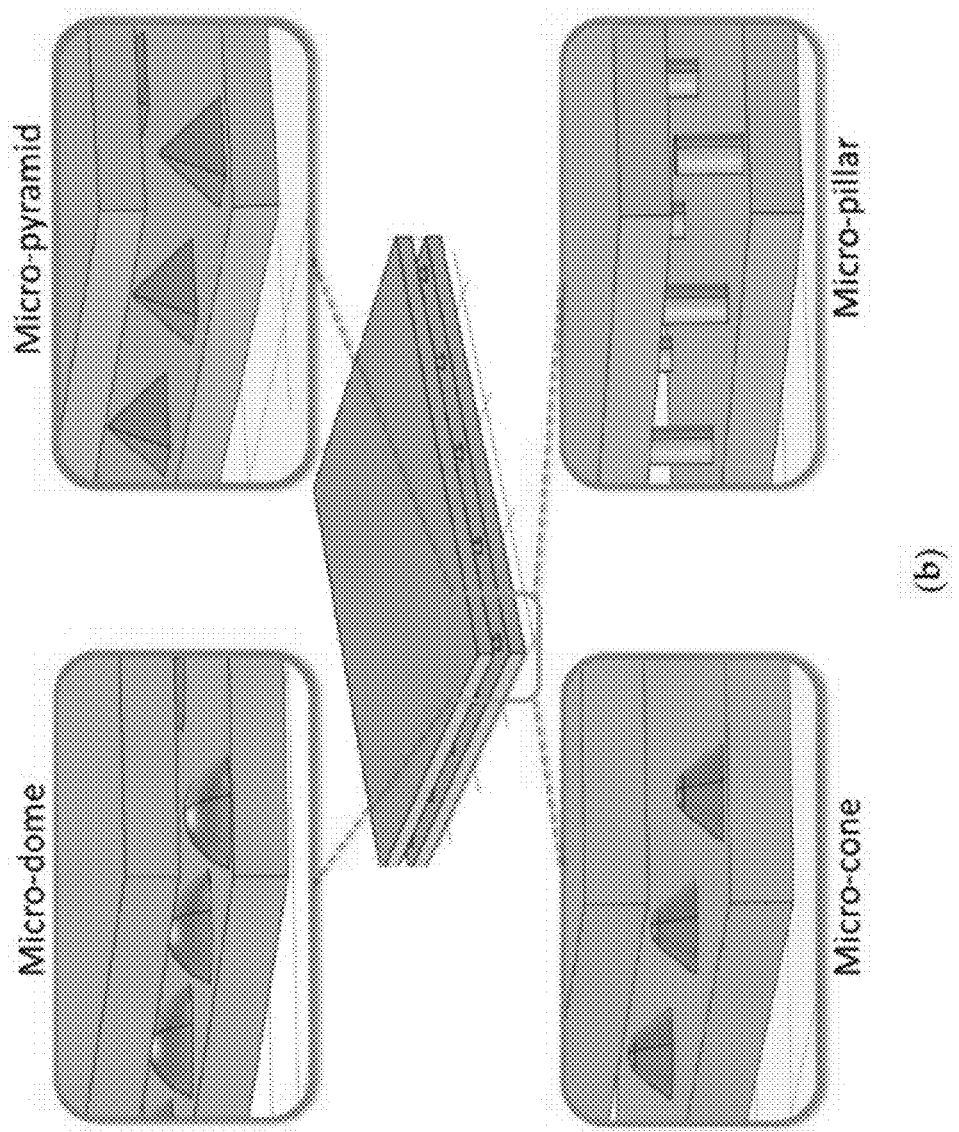

In the first series of simulation modeling, the effect of different micro-feature shapes on current change versus applied pressure (sensor response) has been studied. Specifically, the elastomeric layer is studded with micro-feature shapes of dome, pillar, pyramid, and cone, respectively, as illustrated in FIG. 6B. Secondly, the influence of the sensing material's conductivity on the sensitivity and the level of the current have been studied. To study the electrical conductivity of various available sensing materials, such as CNT incorporated PDMS to Gold coating, different conductivity values has been assigned to the elastomeric layer (1 S/m to $10^5$ S/m). And finally, in the third series of simulations which was done in 2D, a micro-feature shape, namely the micro-pyramid, was chosen and its geometric dimensions and spatial arrangements were optimized. The relevant materials data of the simulation setup is summarized in the Table 2.

Several assumptions and boundary conditions that have been made in this simulation are as follows. 3D simulations have been utilized for realistic analysis of the effects that various micro-feature shapes have on sensor response. However, due to the high volume of calculations, parameters consisting of angle, base size, and number density of micro-pyramid design were optimized by 2D simulations. The effect of the temperature and humidity variation of the conductivity is assumed to be insignificant. Moreover, the materials properties assigned to each layer are uniform throughout that layer, and there are no localized variations. Rather than assuming that a coat of conductive material is deposited on micro-features in the flexible sensing layer, the whole layer is considered to be conductive (with different values of conductivity to represent different values associated with the available sensing materials). The micro-patterned flexible layer modelled to have the conductivity of a sputtered 200 nm thick gold coating (experimentally verified to be 0.1 times of the pure gold's conductivity). The compressive force is applied normally and uniformly to the elastomeric layer to compress it against current collector layer, which is rigid and fixed in space. This flexible layer is modeled to exhibit hyperelastic behavior, while nearly incompressible according to Mooney-Rivlin material model. Finally, an electrical potential difference of 1 volt is applied between the two layers by assigning ground to the flexible layer and +1 V to the current collector layer for generation of passing current between the layers (FIG. 1a).

FIGS. 7A-7D show the results of the simulations studying the effect of different microfeature shapes on the sensitivity of the sensor when the footprint area of each micro-feature and the distance to the neighboring micro-feature remains constant (100×100 µm² and 3 mm$^{-1}$ respectively). Initially, slight pressure between the micropatterned layer and the current collector layer establishes a minimal contact area that allows electrical contact between the layers causing an initial current response ($I_0$). As the pressure gradually increases on the sensor the localized deformations lead to increased contact area between the two layers. Depending on the shape of the micro-features in the elastomeric layer, the rate at which the contact area increases with applied pressure varies. In principle, due to geometrical differences associated with different shapes the linearity, sensitivity, and the current level response of the sensor can vary.

Figure 7A:
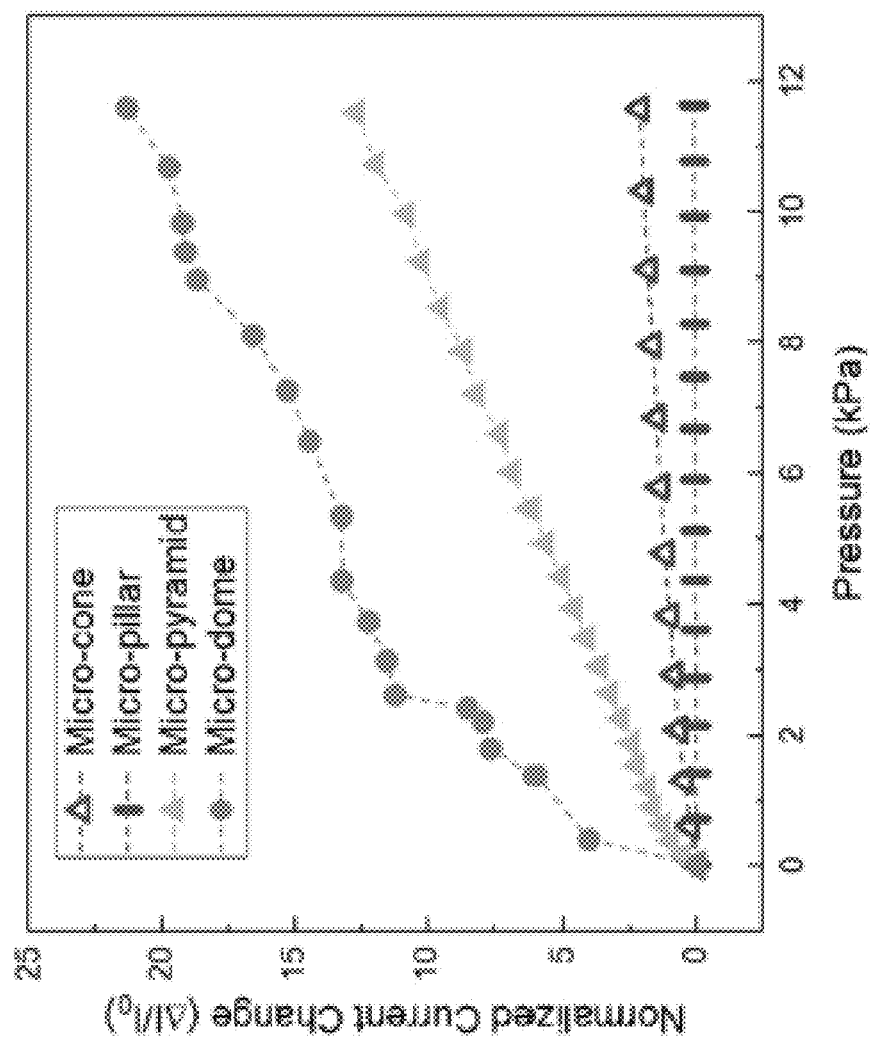
FIGS. 7A-7D show simulation results for a three dimensional pressure sensor according to an embodiment of the subject invention.
Figure 7B:
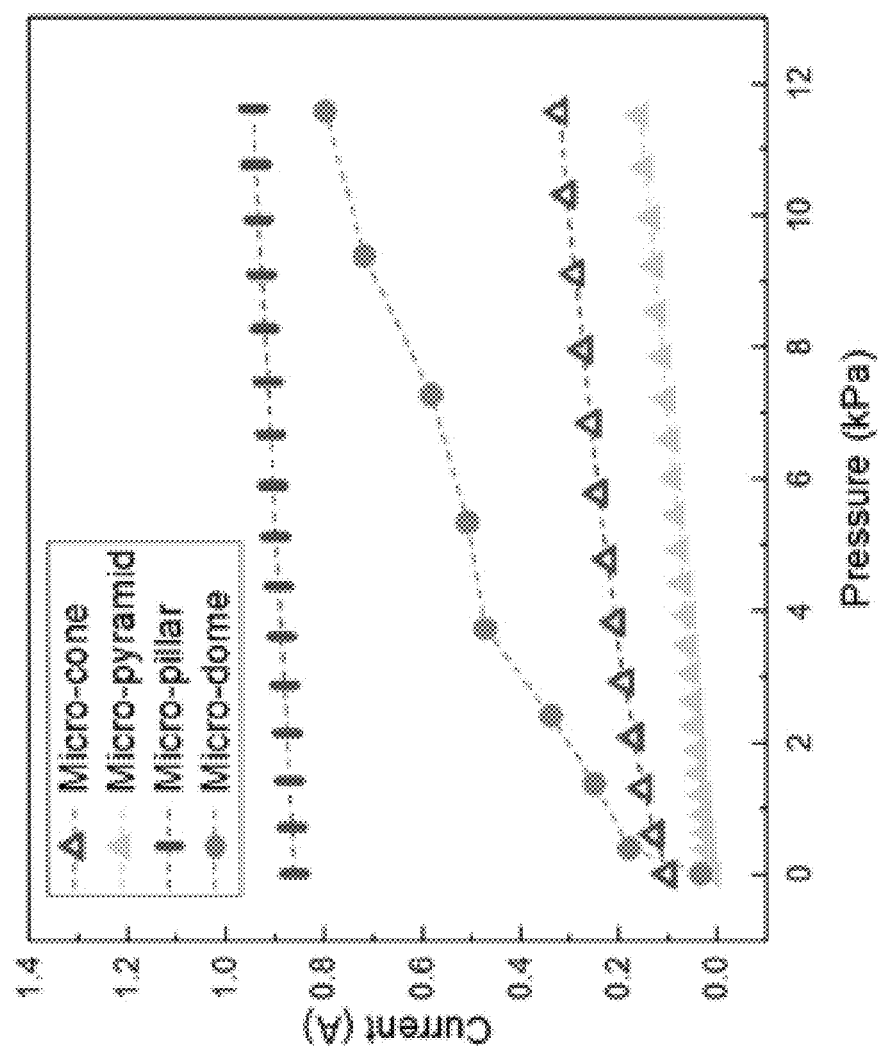

FIGS. 7A and 7B show the results of 3D modelling of four different sensors with the same size but distinct microfeature shapes. As the pressure pushing the layers against each other increases from 0 to 12 kPa, the response from micro-dome shows the highest slope which translates to highest sensitivity among all the proposed shapes. Furthermore, the frequently reported micro-pyramid design also displays a good sensitivity in the range mentioned. Other designs namely micro-cone and micro-pillar show lower relative sensitivities; however, the latter shows a higher initial current response which can be useful in applications such as switch type pressure sensors with digital mode of operation. Linearity in a sensor is desired because of both the mathematic simplicity that allows for sensor's response prediction, and also enabling the detection of an irregular sensor response. Although micro-domes offer excellent sensitivity, they do not offer linear response. On the other hand, micro-pyramid arrays exhibit clear linearity with acceptable sensitivity. Other micro-feature shapes also show linearity however they lack the high sensitivity of micro-pyramid design (FIG. 7B).

Figure 7D:
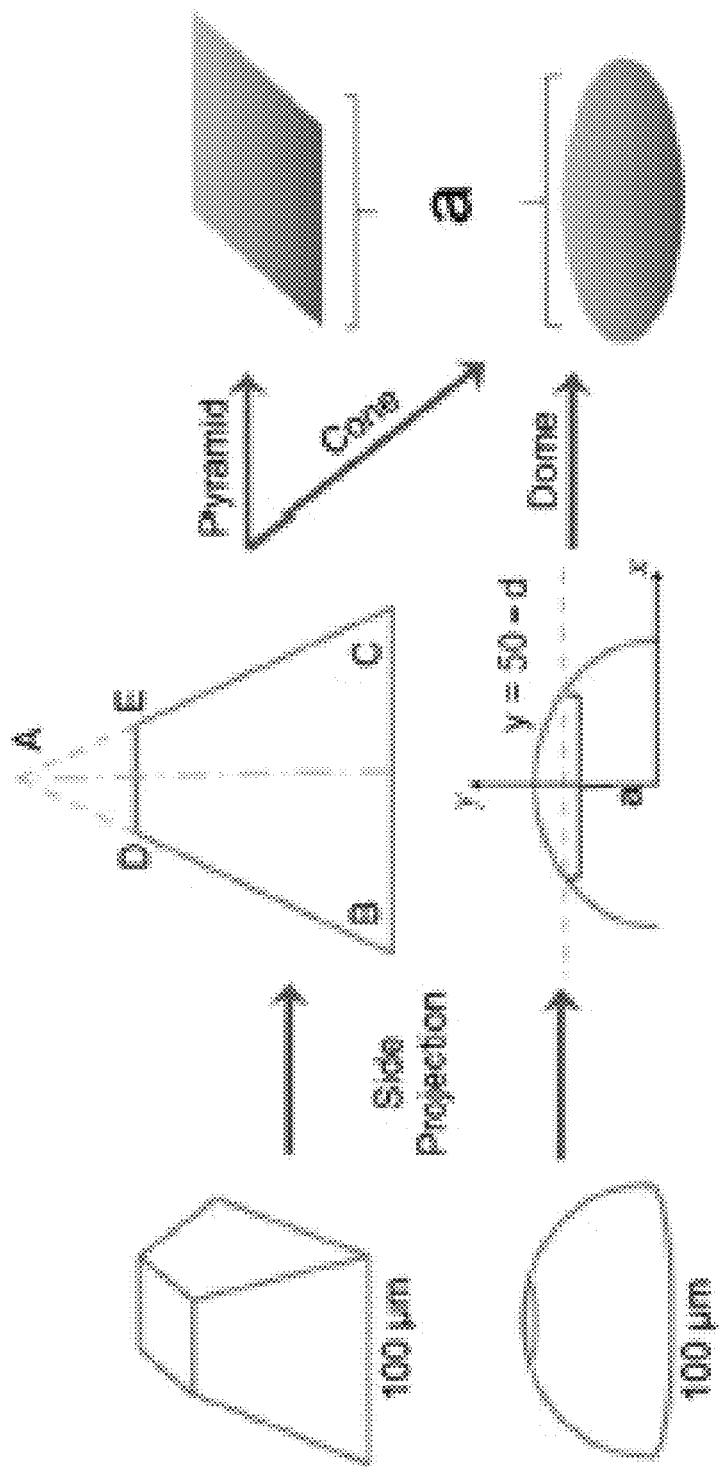
Figure 8A:
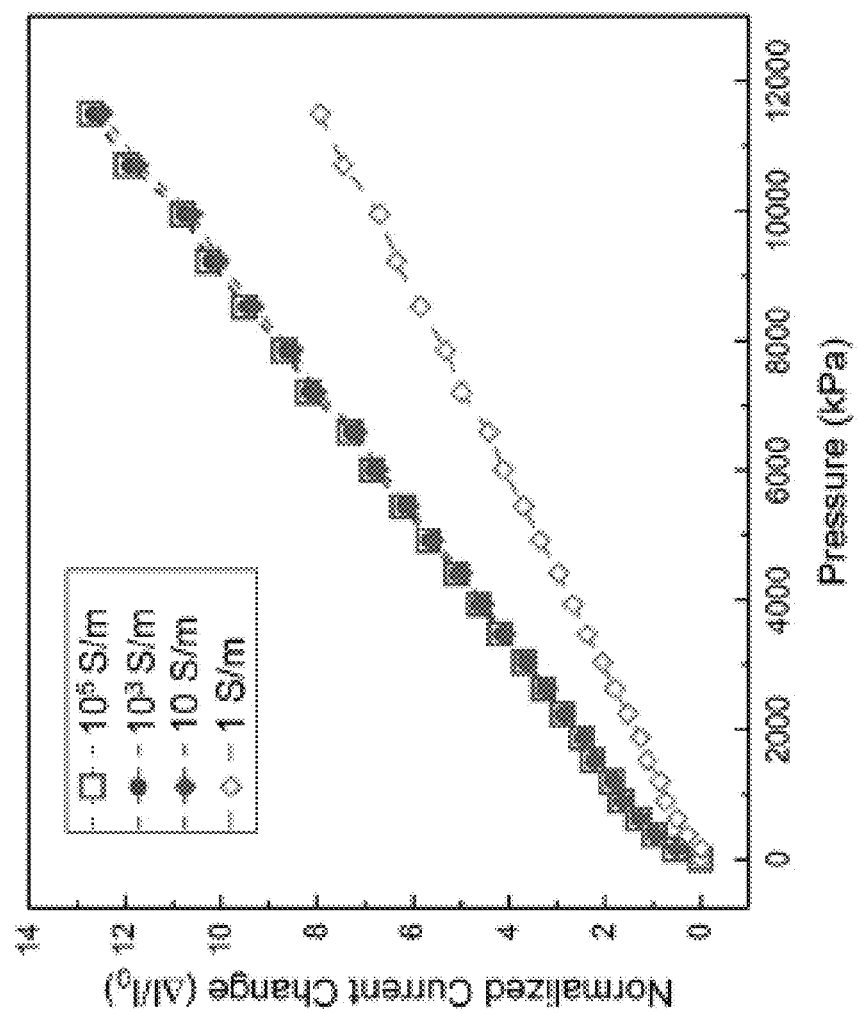
FIGS. 8A-8B show simulation results for a three dimensional pressure sensor according to an embodiment of the subject invention.
Figure 8B:
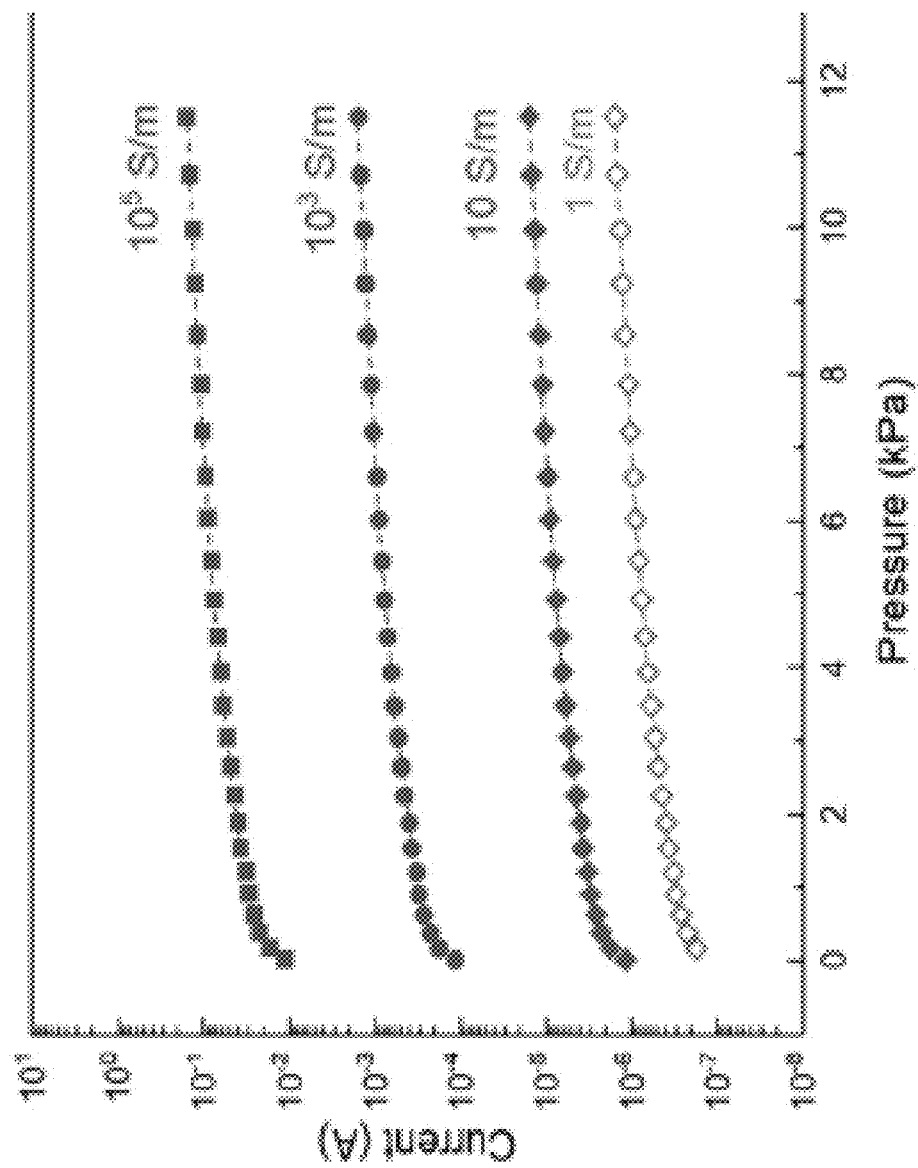

To further explain why micro-feature shapes have the abovementioned effects on the sensor's response, an analytical reasoning is provided as follows. If one considers micro-pyramid as an example of a micro-feature in micro-patterned piezo-resistive sensors, the Thales theorem describes the relationship between the shape and the contact area change when the sensor undergoes compression as the result of its operation (FIGS. 8A-8B). Since at low pressure ranges (e.g., 0-12 kPa) compression force only causes rather minimal deformations at the tip of the micro-feature it can be deduced that the side projection of a pyramid is deformed simply from a triangle into a trapezoid (FIG. 8A). As a result, Thales theorem Equation (4) can be applied to the initial and the final shapes after the compression to find a mathematical relation governing how length "a" (represents the length of the contact area) changes when the sensor is deformed under compression (FIG. 7D). Thus, considering the Thales theorem, Equation (4) and FIG. 7D, the relationship between "a" (the width of the flattened tip area) and "d" (displacement of top layer against elastomeric layer) can be mathematically expressed as Equation (5).

$$\frac{DE}{BC} = \frac{AD}{AB} = \frac{AE}{AC} \tag{4}$$

$$\frac{\frac{1}{2} \times a}{\frac{1}{2} \times \ell} = \frac{d}{\frac{1}{2} \times \ell \times \tan\alpha} \tag{5}$$

It can be seen that for a pyramid with a chosen angle of 60 degrees (α), the relationship between "a" and "d" is established by trigonometry. And from the FIG. 2d, it can be perceived that the contact area between the layers is in form of a square whose sides have length of "a". Therefore, simply the contact area of a pyramid micro-feature ($S_p$) is given by Equation (6). Similarly, for the case of a micro-cone studded sensor (also with an angle of 60 degrees), since the side projection of the micro-cone is the same as the micro-pyramid, the relationship between "a" and "d" does not change. However, the micro-cone forms a circular contact area whose diameter equals to "a". This surface area is given by Equation (7).

$$S_p = 1.3333d^2 \quad (6)$$

$$S_c = \frac{\pi}{4}a^2 = 1.0472d^2 \quad (7)$$

On the other hand, in the case of micro-dome structures, considering the side projection of a dome (FIG. 7D) and forming a system of equations as follows Equation (8). The length "a" is basically the distance between the two points of intersection of the aforementioned lines which is expressed by Equation (9). Finally, using the value obtained for "a" then the contact area of the dome which is in form of a circle is calculated by Equation (10).

$$\begin{cases} x^2 + y^2 = 50^2 \\ y = 50 - d \end{cases} \quad (8)$$

$$a = 2\sqrt{100d - d^2} \quad (9)$$

$$S_d = \pi(100d - d^2) \quad (10)$$

It should be also noted that since the analysis has assumed no lateral flow of material during compression, deformation of micro-pillar causes no contact area increase. The Equation (9) predicts modest change in current response of the sensor in the simulation results due to the lateral material flow and increase of contact pressure that leads to higher inter-layer conductivity because of microscopic surface roughness flattening. Therefore, the developed analytical relationship is in accordance with simulation results.

Figure 7C:
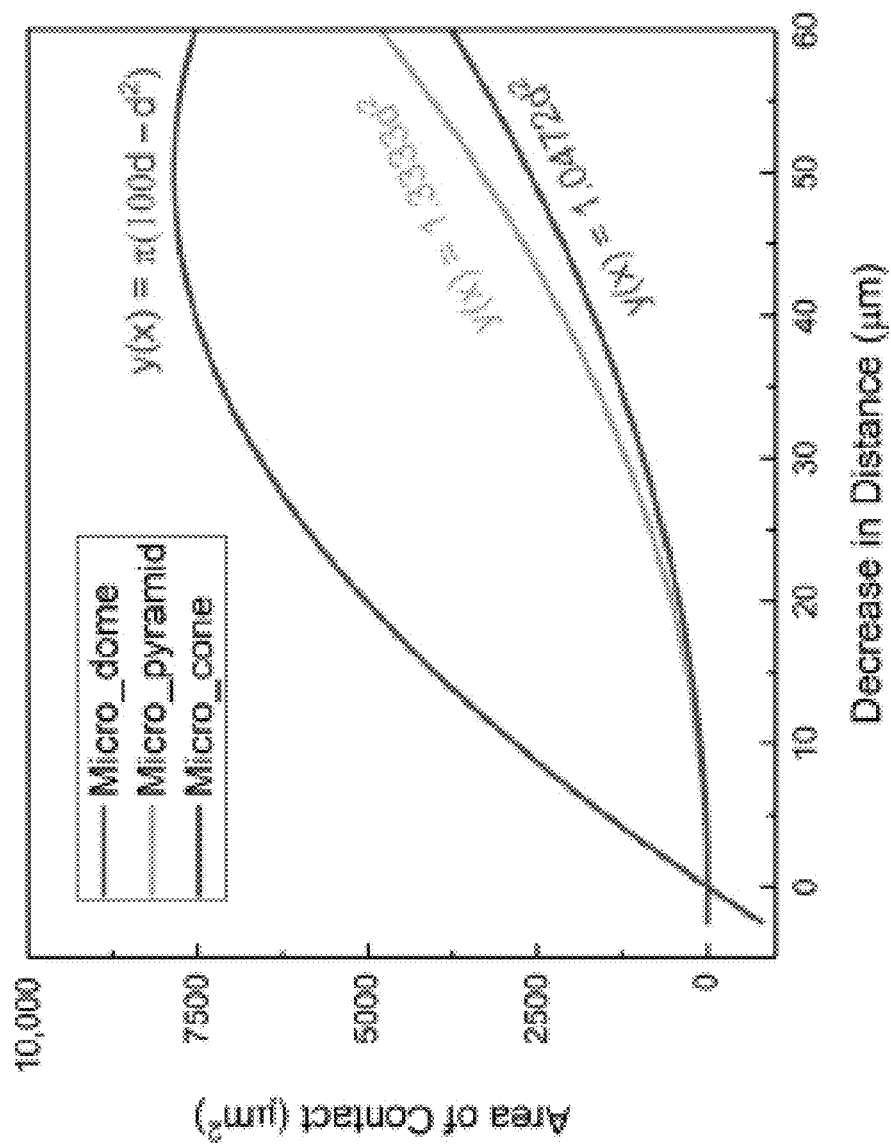

Utilizing the above developed analytical equations, the change of contact area vs. decrease of layer spacing for each micro-feature shape is plotted in FIG. 7C. The observed trends in this plot are in accordance with the current responses seen in the COMSOL simulation results. Here, for pressure ranges of 0-12 kPa, which corresponds to 0-20 μm of layer spacing decrease, the micro-dome's results show the steepest slope (i.e., the highest rate at which the surface area changes when the layers get closer together). Moreover, the micro-pyramid design results show a higher slope than micro-cone design results which is due to the geometry of the shape as discussed before.

The Effect of Conductivity on the Sensor's Response is investigated in terms of sensitivity and the passing current level with various elastomeric layer conductivities when the shape, geometrical parameters and spatial configuration of the micro-feature remains constant (pyramid, 100×100 μm² and 3 mm⁻¹ respectively). The simulation results show that the sensitivity of the sensor saturates at the elastomeric layer conductivity of 10 S/m and becomes independent of it. However, if the conductivity value falls below 1 S/m which is in range of conductive polymers such as carbon nano tube (CNT) infused PDMS, the sensitivity deteriorates. At these conductivity values the high resistance of the elastomeric layer serves as a limit to the passing current between the layers and thus reducing the overall sensitivity of the sensor. For this reason, in order to achieve high sensitivity in piezo-resistive sensors, it is recommended that elastomeric layer be coated with a highly conductive layer like gold or as an example other novel conductive materials such as Zirconium nitride (~2×10⁶ S/m) with conductivity values higher than 10 S/m. In most cases, compositing the elastomeric layer with conductive materials leads to polymers that are not conductive enough which would adversely affect the sensitivity of the pressure sensor. Embodiments provide an elastomeric layer conductivity of 10 S/m, alternatively, 11 or higher S/m, alternatively, 9 S/m, 8 S/m, 7 S/m, 6 S/m, 5 S/m, 4 S/m, 3 S/m, 2 S/m, or 1 S/m, including increments, combinations, and ranges of any of the foregoing. The desired elastomeric layer conductivity can be achieved by materials selection, modification, coating, and other methods known in the art or later developed. For example, a sputtered 200 nm thick gold coating can provide sufficient conductivity.

One important characteristic of the piezo-resistive pressure sensor is the magnitude of output signal. In this example the dependence of the sensor's output signal level on the conductivity of the elastomeric layer (e.g., sensing layer) is investigated. Through 3D simulations of piezo-resistive sensor operation (FIG. 8B), it can be found that the higher the conductivity values of the sensing material leads to higher level of passing current with the same applied voltage (e.g., 3 Volts) between the layers of the sensor. In fact, a piezo-resistive sensor that is gold coated (e.g., sputtered to a thickness of 150 nm) exhibits a conductivity value of $10^5$ S/m (experimentally verified) which according to the results leads current output in range of milliamps. This is practically advantageous for two reasons. First, it allows the signal acquisition with relatively simple electrical circuitry (e.g., simple and broadly accessible development boards), and second, it provides higher signal-to-noise ratio which in turn allows use of amplifiers to further facilitate the signal acquisition. While several reports of composited polymer piezo-resistive sensors exists in the literature, their current output signal ranges typically in nanoamperes and low microamperes in case of measuring pulse from a human wrist. This necessitates the use of relatively big, bulky, desktop-sized source meters for signal acquisition. Since most of these sensors are targeted for detection of weak physiological sensors as a wearable device, dependence of signal acquisition on bulky source meters is detrimental. Therefore, use of highly conductive coating material of a flexible elastomeric layer is advantageous in order to achieve high level of passing current to be detectable by truly wearable signal acquisition development boards.

In order to investigate the how the geometric parameters of a given design can influence the sensitivity, a micro-pyramid patterned sensor with conductivity value of similar to gold ($10^6$ S/m), was chosen for investigation. Various external pressures in the range of 0-1500 Pa were applied to the sensor in this simulation. Parameters including micro-feature dimensions and spatial arrangements have been studied as shown in FIGS. 9A-9D. Because of the similarities between micro-patterned pressure sensors designs, parameters optimized for one design can be easily generalized to the other micro-patterned pressure sensor shapes. Here, micro-pyramid studded sensor behavior was studied due to its similarities to other micro-patterned pressure sensors such as micro-cone, micro-dome, and micro-pillar. Therefore, sensors length of 2.1 mm with three different pyramid spatial densities consisting of low, medium, and high number density (corresponding to six, nine, and fifteen pyramids, respectively) were simulated to study the impact of micro-feature number density on sensitivity. According to the FIG. 9B, low number density setup data yields to the highest slope of the fitted curve which means that this setup shows the most sensitive response among all three setups. This is due to concentration of the exerted pressure at fewer pyramids. More severe deformations at these contact points essentially mean larger contact area between the layers which in turn translates to lower resistance and higher passing current.

Figure 9A:
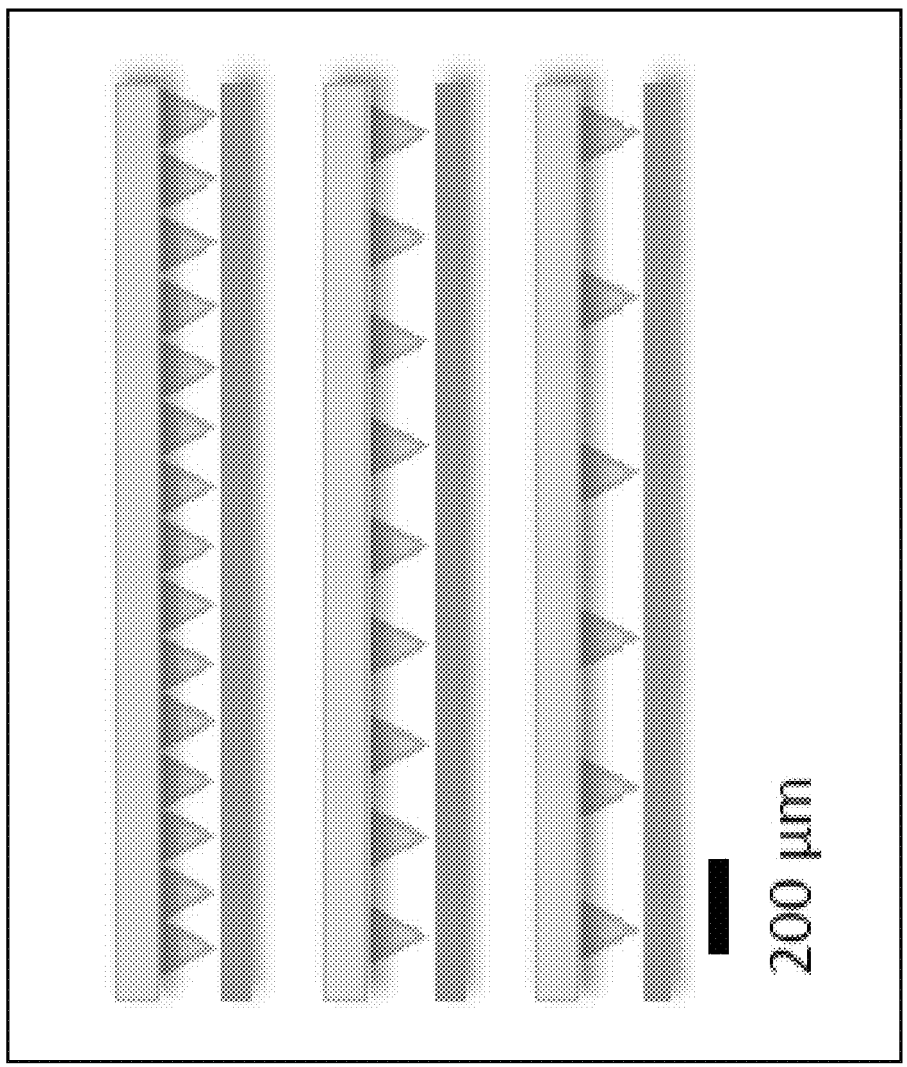
FIGS. 9A-9D show a schematic design and simulated relative current as a function of applied pressure for different parameters under investigation according to embodiments of the subject invention.
Figure 9B:
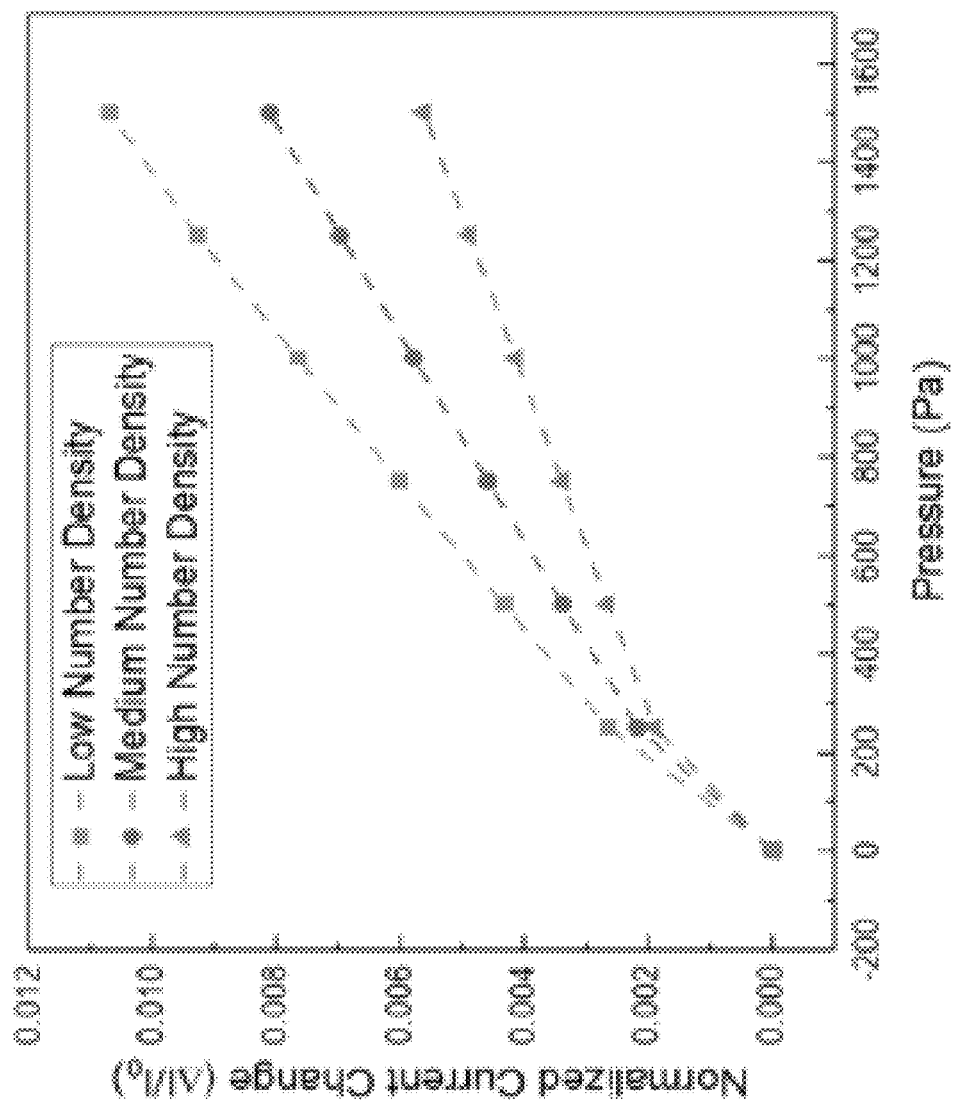
Figure 9C:
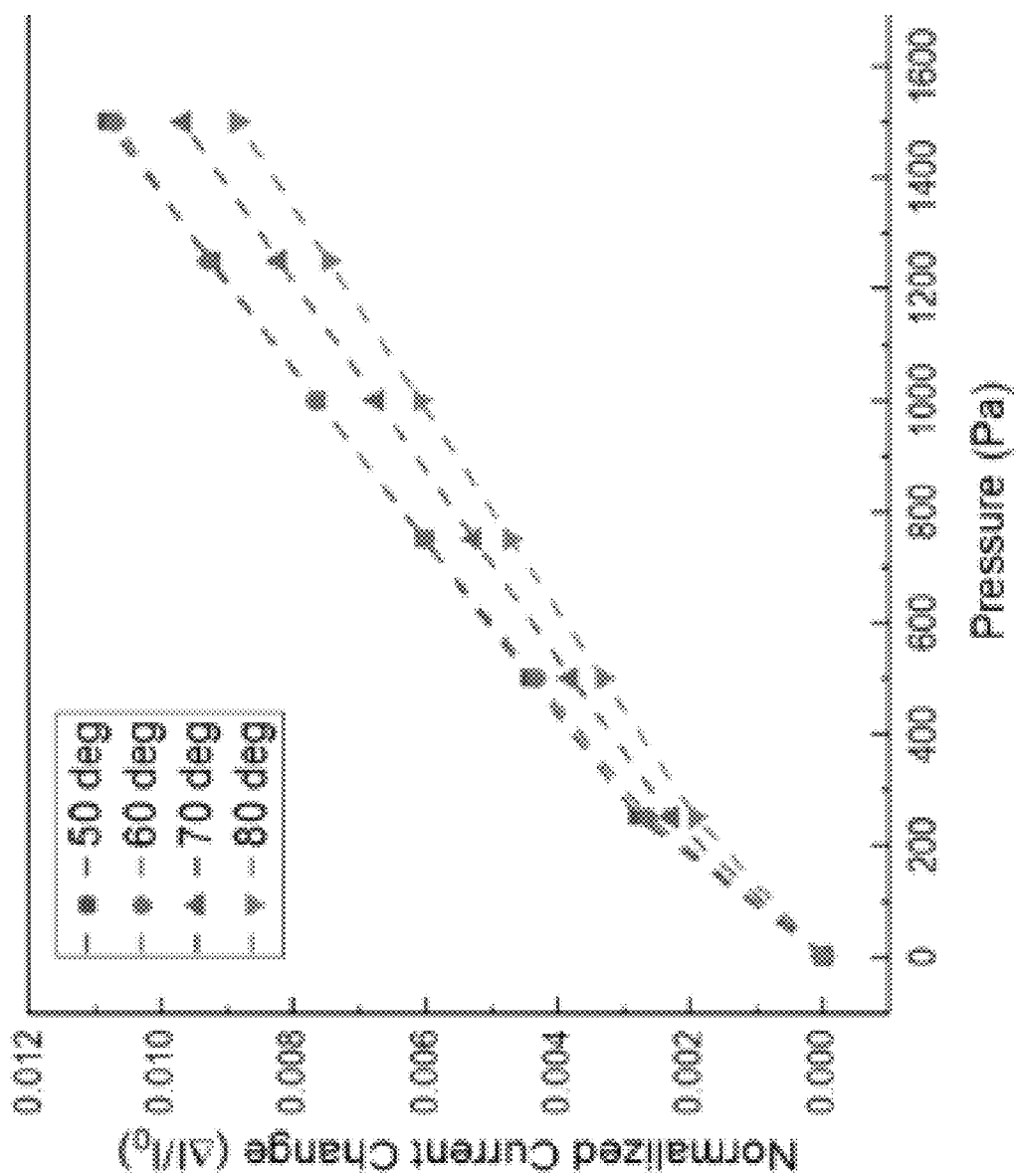
Figure 9D:
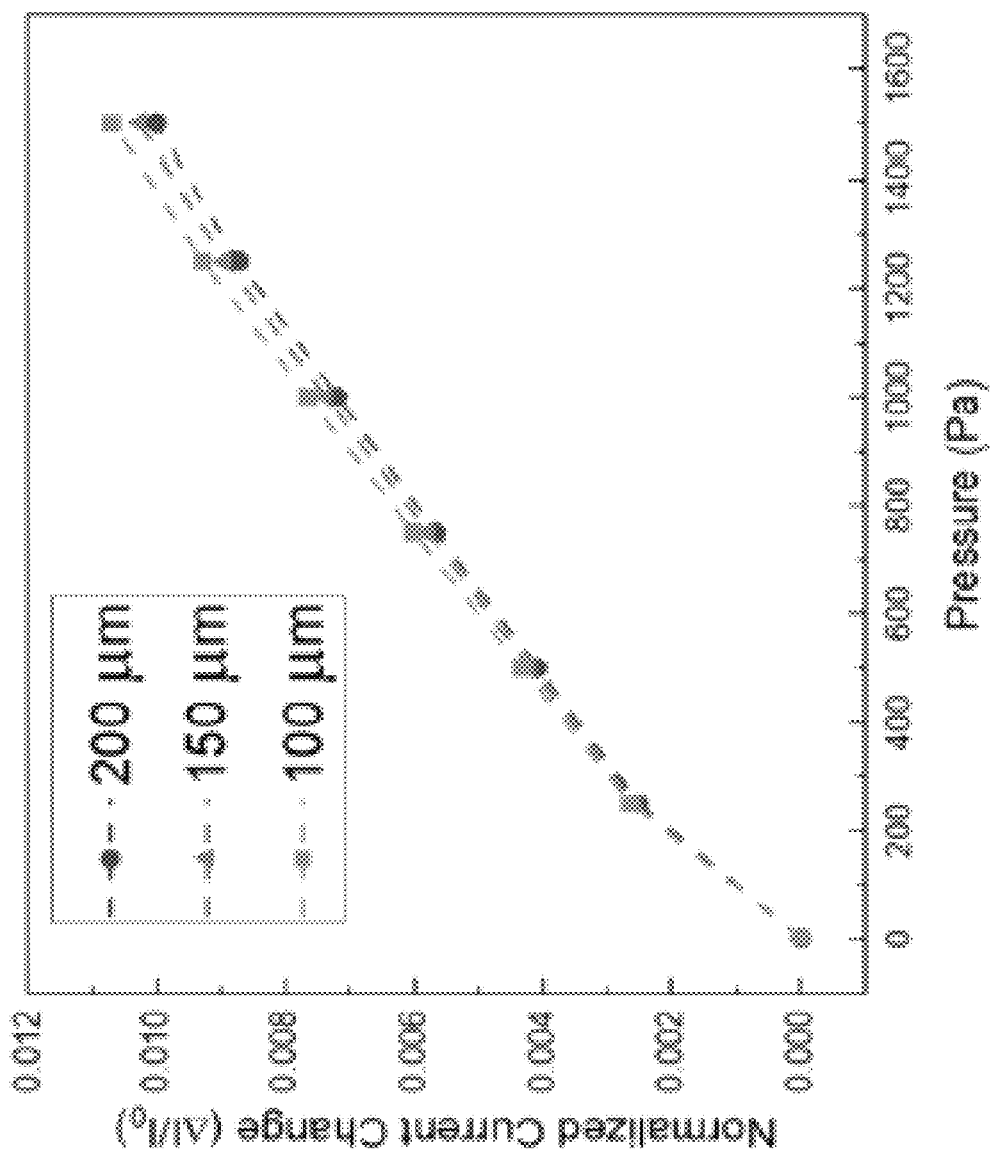

To quantitatively compare the sensitivity arisen form setups with different pyramid angles at the same sensor length of 2.1 mm, micro-pyramid designs with angles (e.g., as depicted by "$\alpha$" in FIG. 6A) between 80 to 50 degrees have been studied in FIG. 9C. The results depict that pyramids with angles of 50 to 60 degrees show relatively a more sensitive response. The reason for this lies in a balance between the contact area growth rate (highest growth rate corresponds to 50 degrees according to the Equation (6) and the amount of localized pressure at contact areas between the layers. It should be noted that in order to achieve high contact area growth rate, the localized pressure has to be high enough to enable the deformation. The highest localized pressure is typically experienced in structures with low contact area growth rate (i.e., 80 degrees). Therefore, it is logical to achieve the highest sensitivity with a sensor that is studded with 50 to 60-degree angle pyramids in which case both factors have medium and balanced influence. This is in turn in accordance with the aforementioned simulation results. Furthermore, an easier way to manipulate the design of a micro-feature studded sensor, rather than changing the angle, is to change the size of the micro-features themselves. Practically this is done by changing the microfabrication mask. To study this, simulations were conducted by changing the size of micro-features (e.g., as depicted by "$\ell$" in FIG. 6A) with three base sizes 100, 150, 200 μm all with previously determined sensitive configurations which are 60-degree pyramid angle and low number spatial density. As shown in FIG. 9D, the normalized current change (i.e., sensitivity) increases as the sensor is compressed under external pressure. All three configurations show linear growth behavior; however, as the feature size gets smaller, namely 100 μm, the slope of the line increases. The higher slope of the fitted lines means higher sensitivity. This is attributed to increasing of the localized pressure because of the smaller contact areas associated with smaller feature sizes.

Overall out of the three above-mentioned geometric parameters, spatial number density of micro-features represents the most influential factor on sensitivity of the sensor since localized pressure experienced at the contact areas, strongly depends on the total number of points of contact between the layers. The fewer the number of contact areas (i.e., lower spatial number density), the higher localized pressure and therefore more deformation and lower electrical resistance between layers. While dimensional parameters such as base size and angle of pyramid show weaker influence on the sensitivity of the sensor, they also have to be taken into consideration in designing of highly sensitive micro-patterned piezo-resistive pressure sensors. Thus based on the findings of this example, in one exemplary and non-limiting embodiment a micro-patterned piezo-resistive pressure sensor for arterial pulse monitoring in contact with skin can achieve potentially higher sensitivity and signal strength if the micro-features are in the shape of domes or pyramids and they are patterned with number density of 3 $mm^{-1}$, feature size of 100 μm, and angle of $50°<\alpha<60°$ (in case of pyramid shape). Also, an elastomer layer having a conductivity of at least 10 S/m to ensure that the sensitivity does not deteriorate due to lack of conductivity. Nonetheless, as the conductivity of the elastomeric layer is enhanced to approach the conductivity of gold, the sensor signal output becomes stronger (i.e., higher current) which is favorable for detection of the signal with simple and inexpensive electrical circuits tailored for wearable applications.

In this example, a series 2D and 3D simulations were conducted to compare the effect of different shaped microfeatures on the sensitivity and signal level of a piezoresistive sensor. The inventors have shown that sensors with arrays of micro-domes and micro-pyramids show higher sensitivity in comparison to micro-cone and micro-pillar studded ones. Moreover, simulations on assigning different values of conductivity provided insights that, in conductivity values of the sensing layer similar to that of a gold coating, the sensor achieves a high signal level response. However, if the conductivity of the sensing layer is similar to that of typical conductive polymers, the sensitivity suffers and the current response is so low that inhibits the practical use of the sensor due to low signal-to-noise ratio. Finally, in a series of 2D simulations it is shown that lower spatial number density in arrays of micro-features, and smaller base size leads to higher overall sensitivity of the micro-patterned piezo-resistive sensor.

Example 3—Multi-Modal Sensor, Exemplary and Non-Limiting Embodiment 1

Figure 10A:
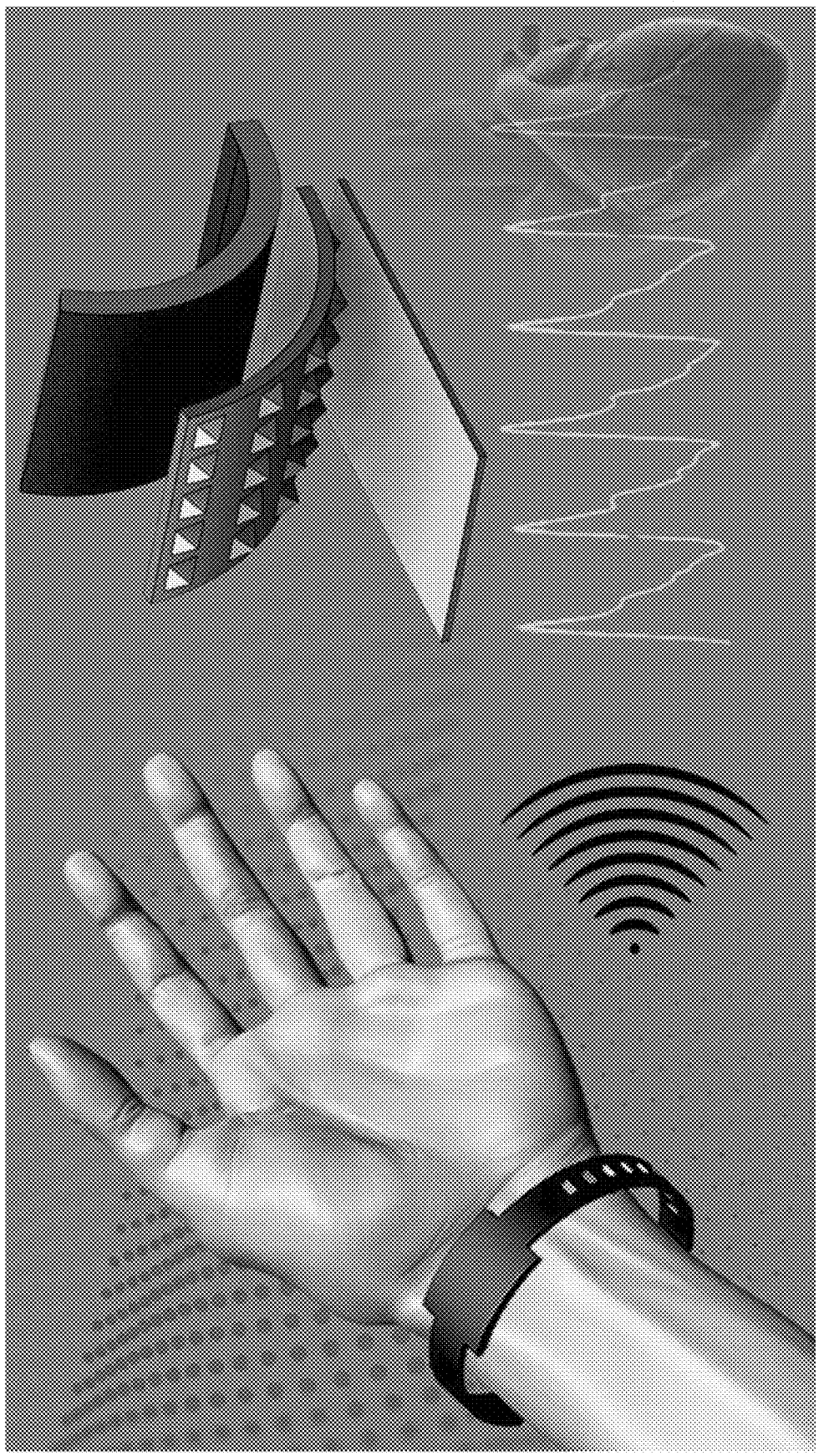
FIGS. 10A-10B show a multi-modal sensor according to an embodiment of the subject invention reading pressure waves caused by heartbeat.
Figure 10B:
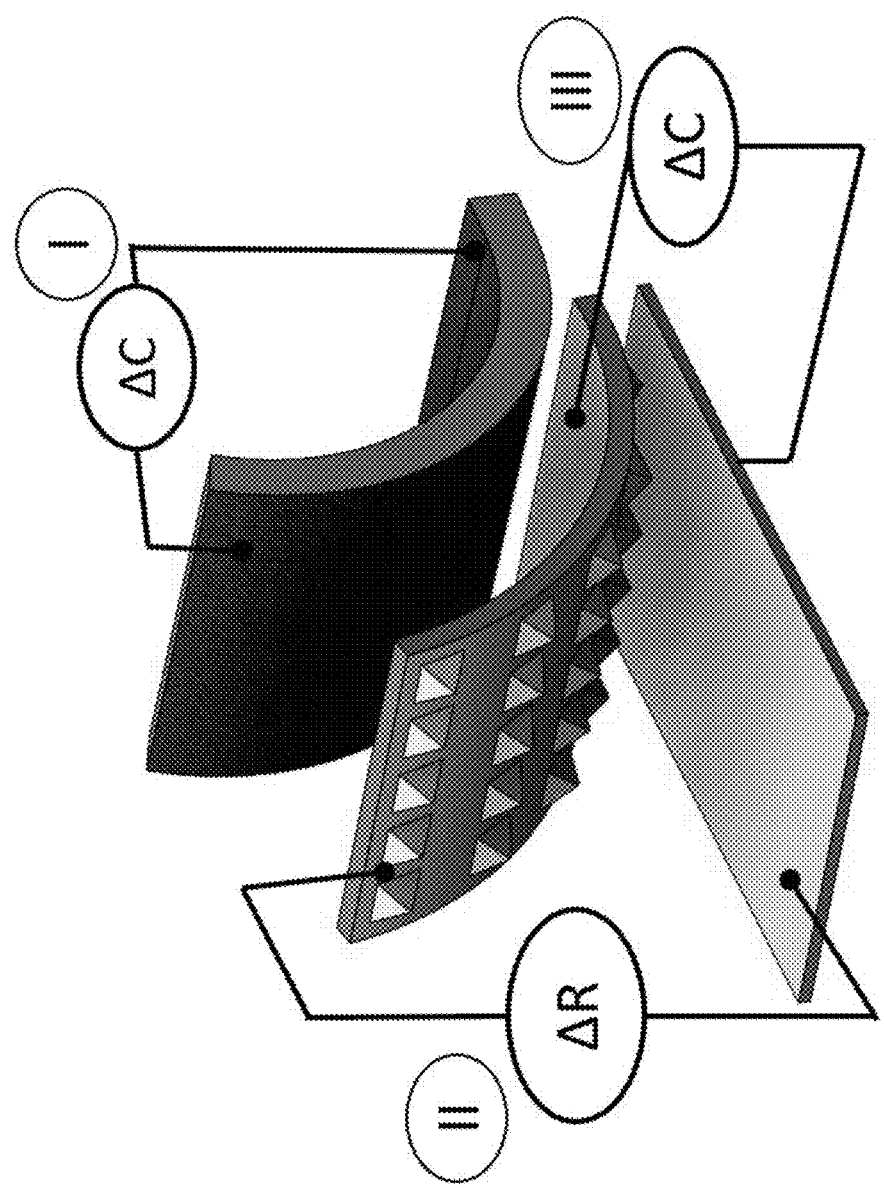

A multi-modal sensor for reading pressure waves caused by heartbeat can be constructed according to an embodiment of the subject invention as illustrated schematically in FIGS. 10A-10B. This prospectively illustrated embodiment comprises (alternately, consists of, or consists essentially of) three parallel modes of operation: a supercapacitive sensor (marked I), a micro-fabricated piezoresistive sensor (marked II), and a capacitive sensor (marked III).

Example 4—Multi-Modal Sensor, Exemplary and Non-Limiting Embodiment 2

A multi-modal sensor can be constructed according to an embodiment of the subject invention as illustrated schematically in FIGS. 11A-11B. As seen in FIG. 11A, this prospectively illustrated embodiment comprises (alternately, consists of, or consists essentially of) three parallel modes of operation through three integrated sensors: a strain gauge sensor (marked I), a micro-fabricated piezoresistive sensor (marked II), and a capacitive sensor (marked III). FIG. 11B shows the components that the piezoresistive and capacitive sensor share and where they are connected to the outside circuit.

Example 5—Experimental Data for Mode II: Piezoresistive Sensor (Fabrication and Test)

Figure 12A:
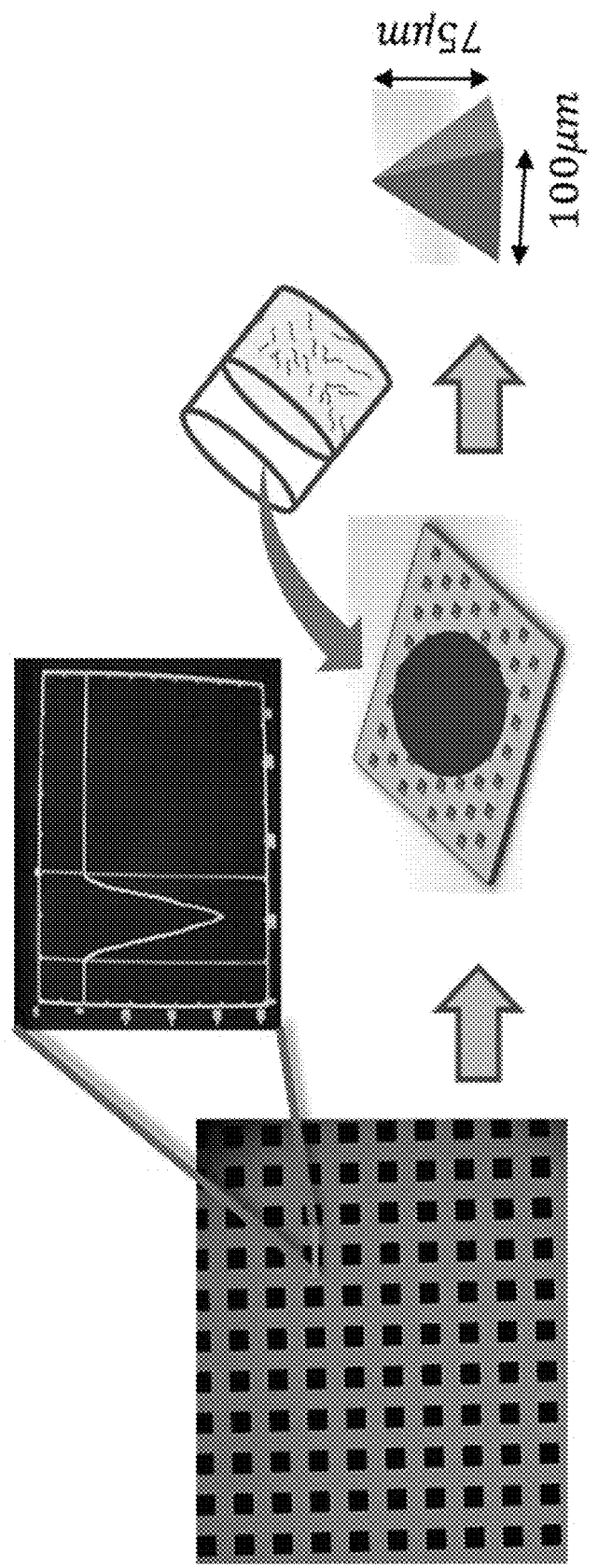
FIGS. 12A-12G illustrate the fabrication, characterization, and testing of a mode II and III (micro-pyramid piezoresistive) sensor according to an embodiment of the subject invention.
Figure 12B:
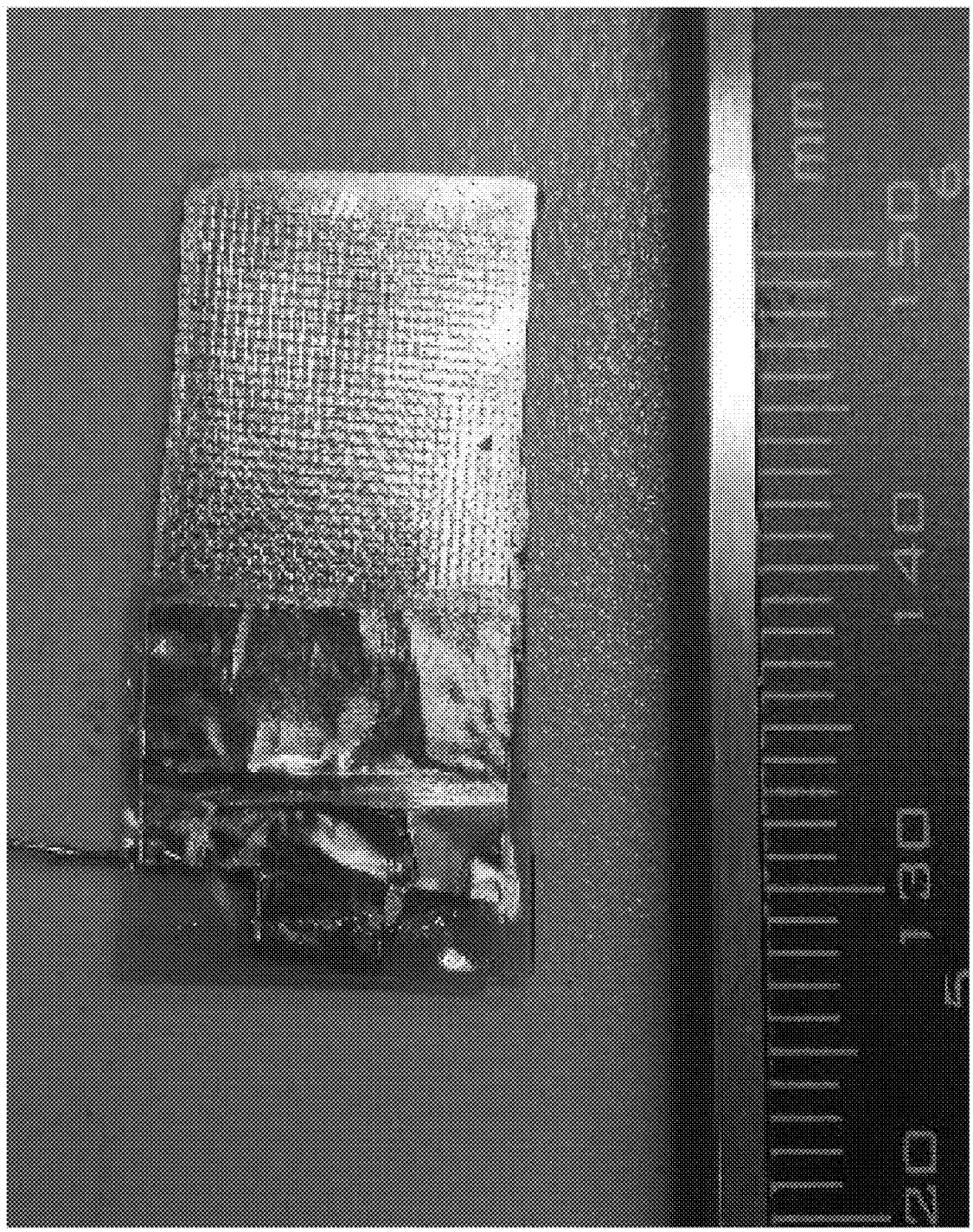
Figure 12C:
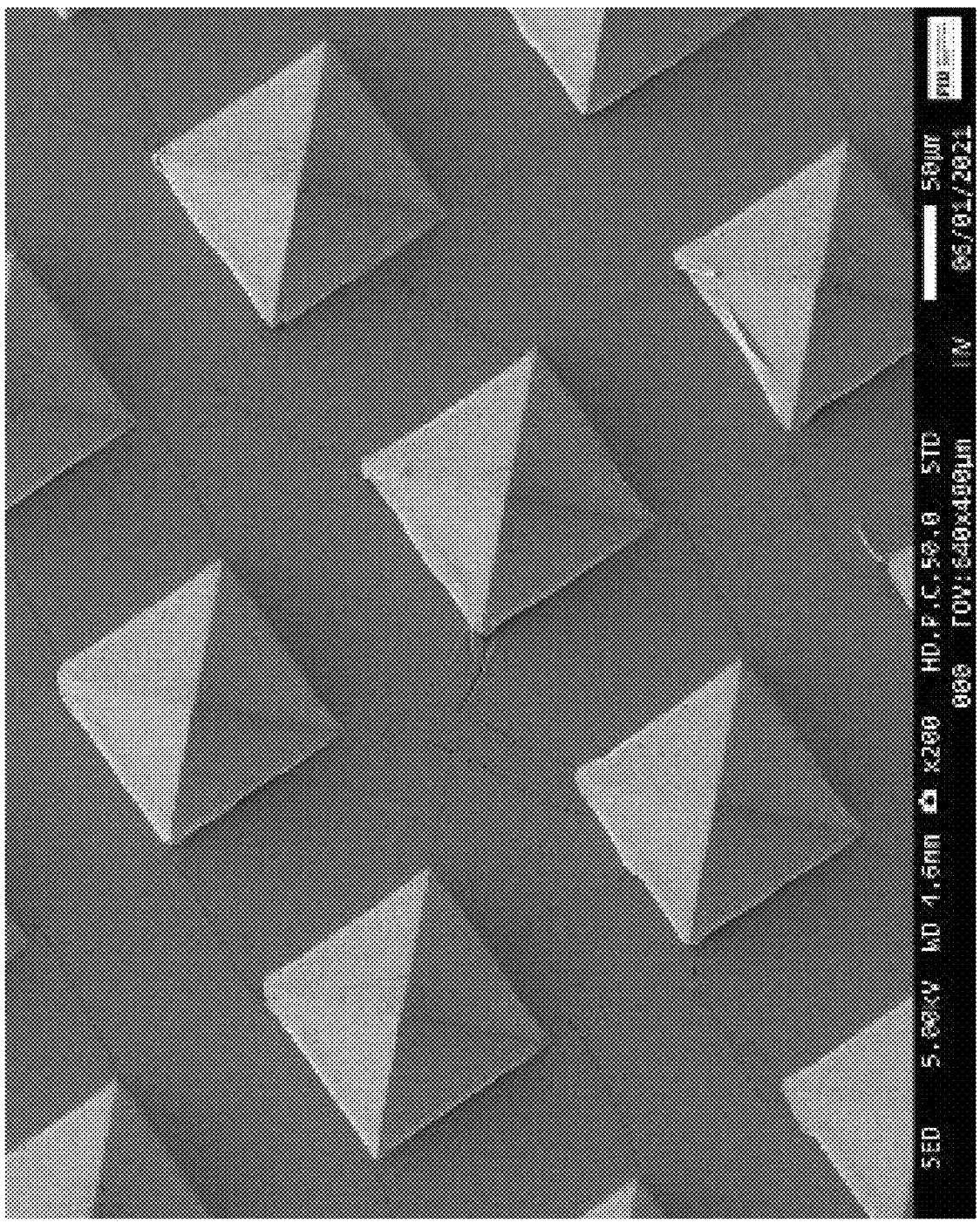
Figure 12D:
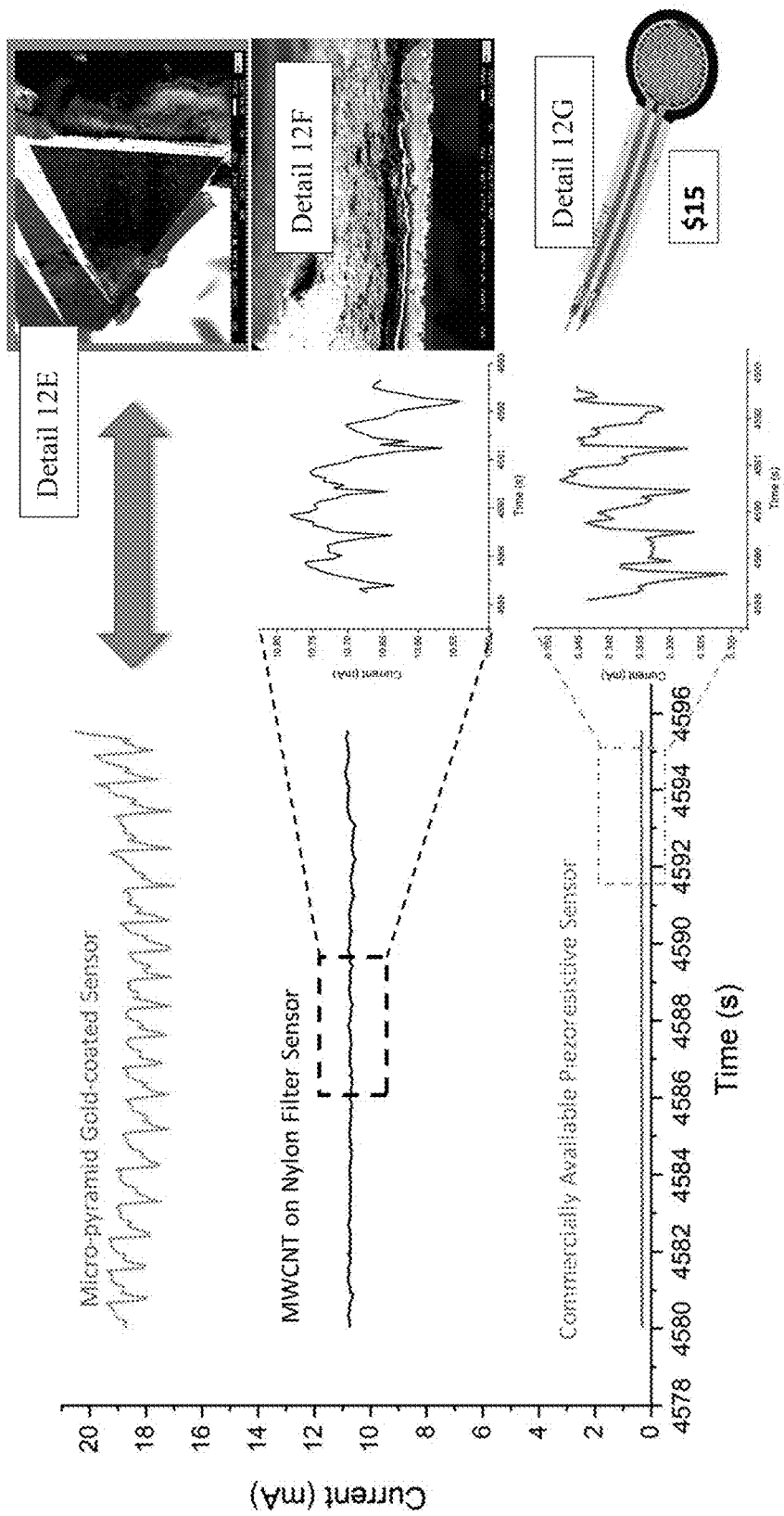
Figure 12E:
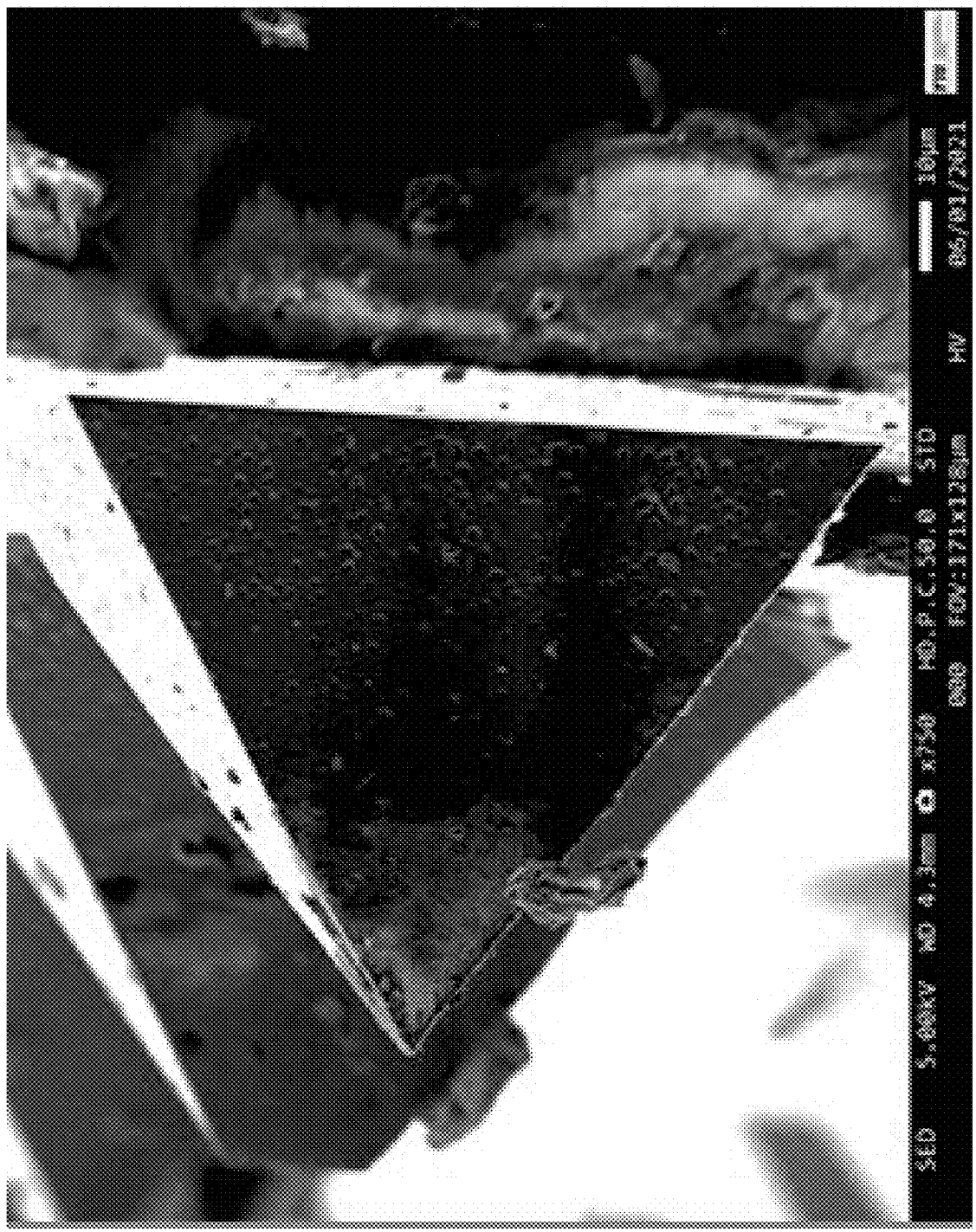
Figure 12F:
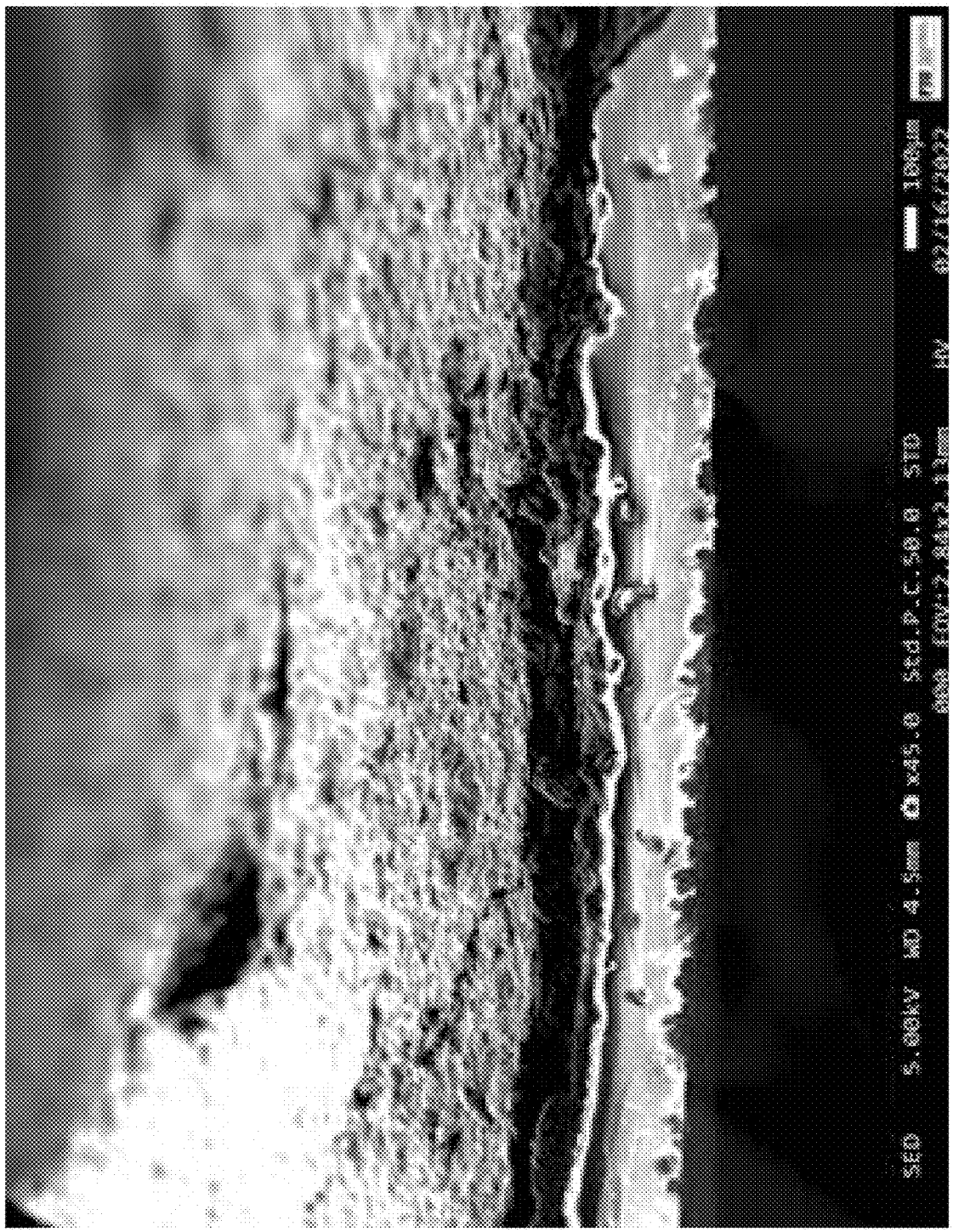
Figure 12G:
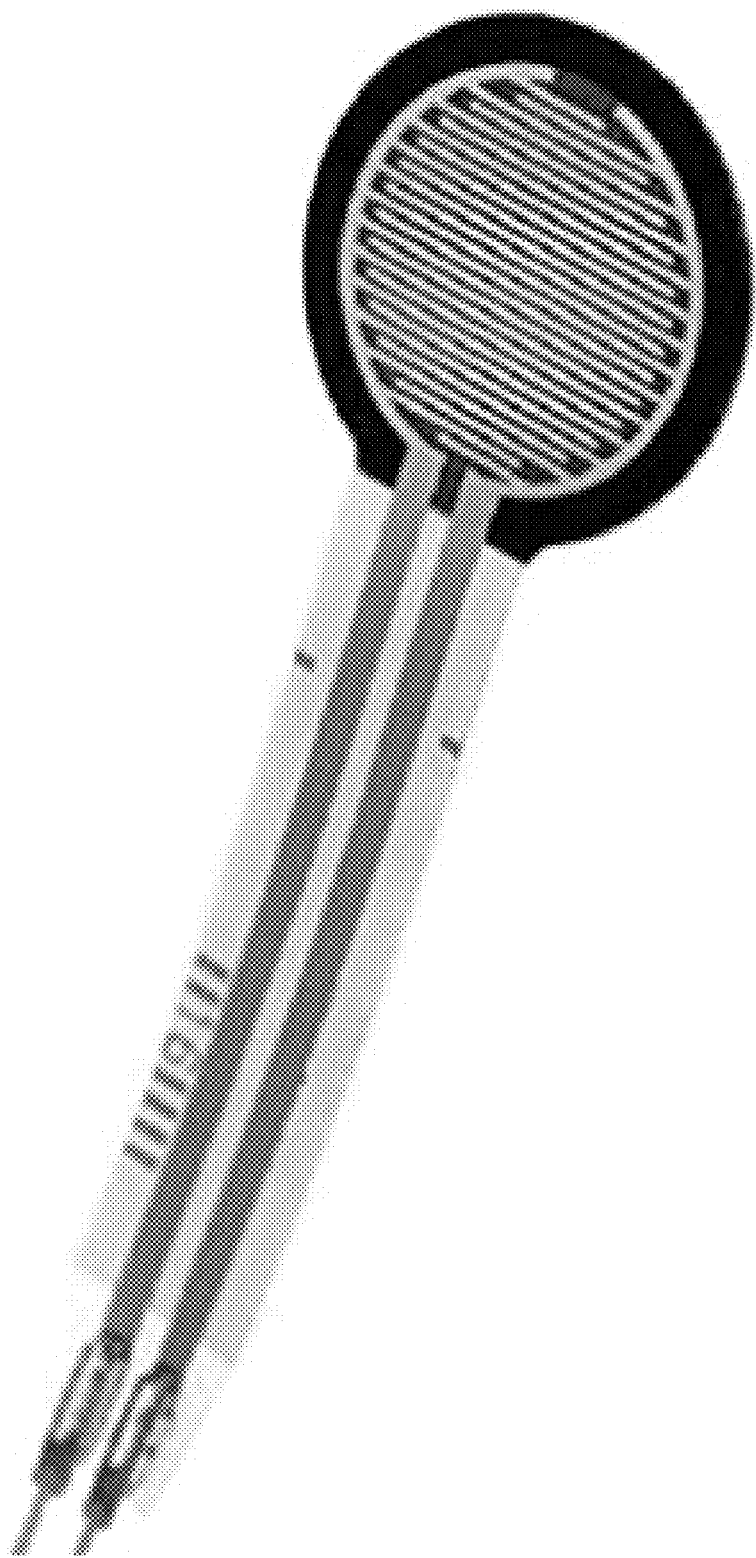

Fabrication of the mode II and III micro-pyramid piezoresistive sensor according to an embodiment of the subject invention is schematically illustrated in FIG. 12A. The process can be summarized in three major steps: (1) A mold having pits in the shape of micro-pyramids using photolithography is fabricated. (2) Uncured PDMS (Polydimethylsiloxane) is poured on the mold. (3) Cured PDMS is detached from the mold having the desired micro-shapes.

As shown in FIGS. 12B-12G, test and characterization included SEM images used to verify if the shapes of the micro-features conform to the designs in the sensor footprint area, and heartbeat measurements using the fabricated sensor and comparison to commercially available sensors. Compared to the commercially available sensor (FIG. 12G), the micropatterned piezoresistive sensor (FIG. 12E) of an embodiment of the subject invention shows 100× signal amplification.

Example 6—Experimental Data for Mode III: Capacitive Sensor (Fabrication and Test)

Figure 13A:
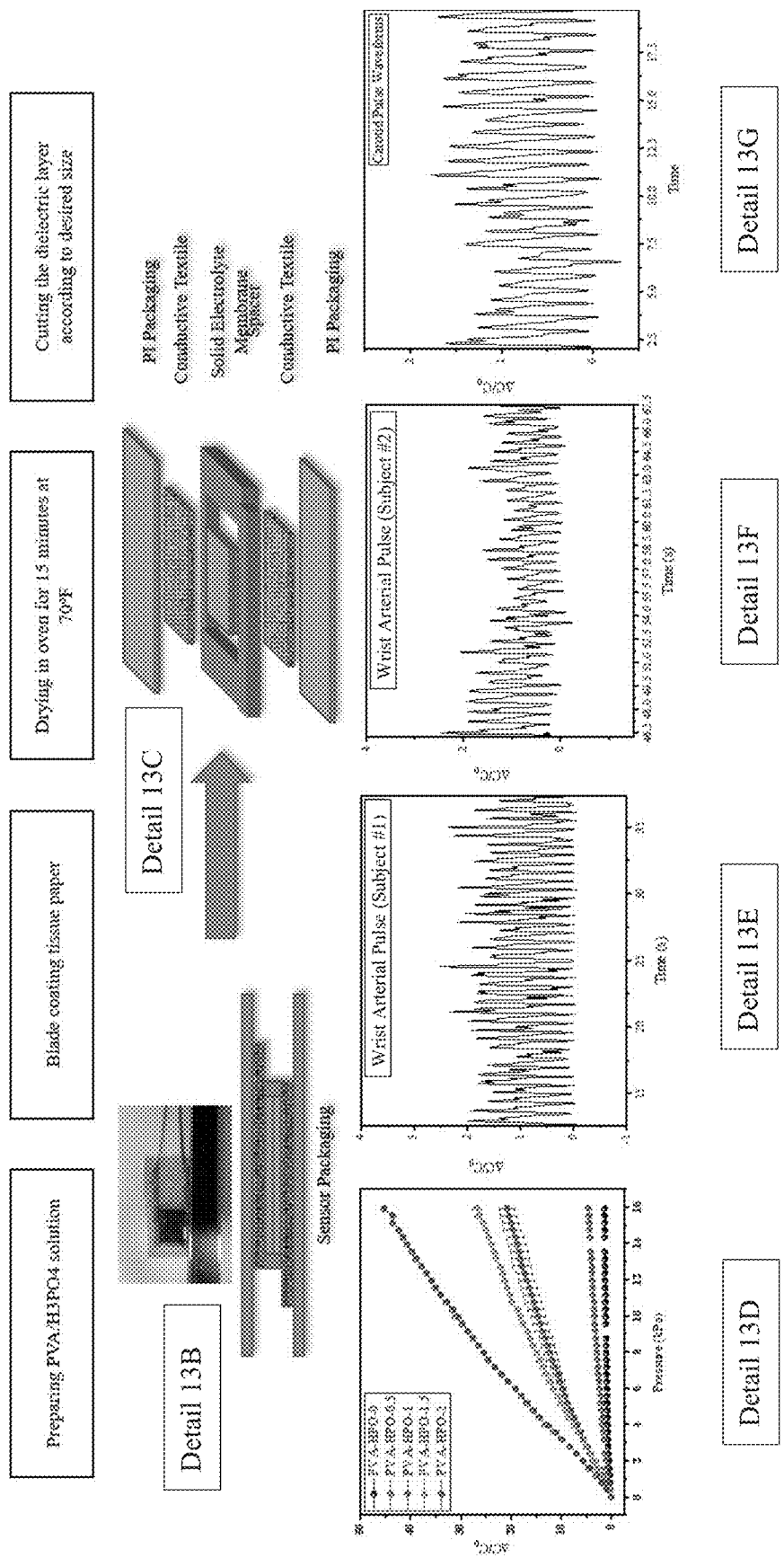
FIGS. 13A-13G illustrate the fabrication, characterization, and testing of a mode III (capacitive) sensor according to an embodiment of the subject invention.
Figure 13B:
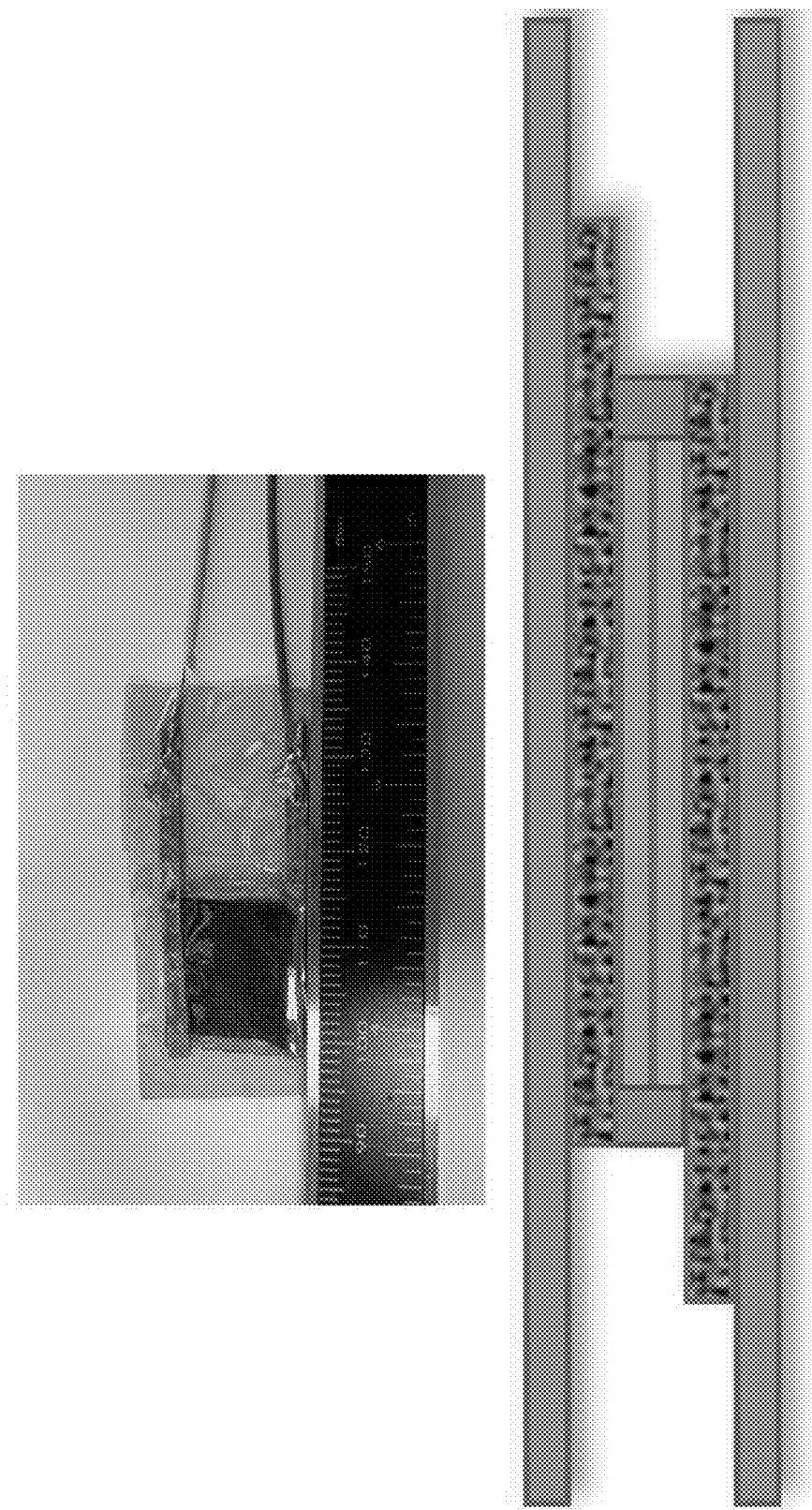
Figure 13C:
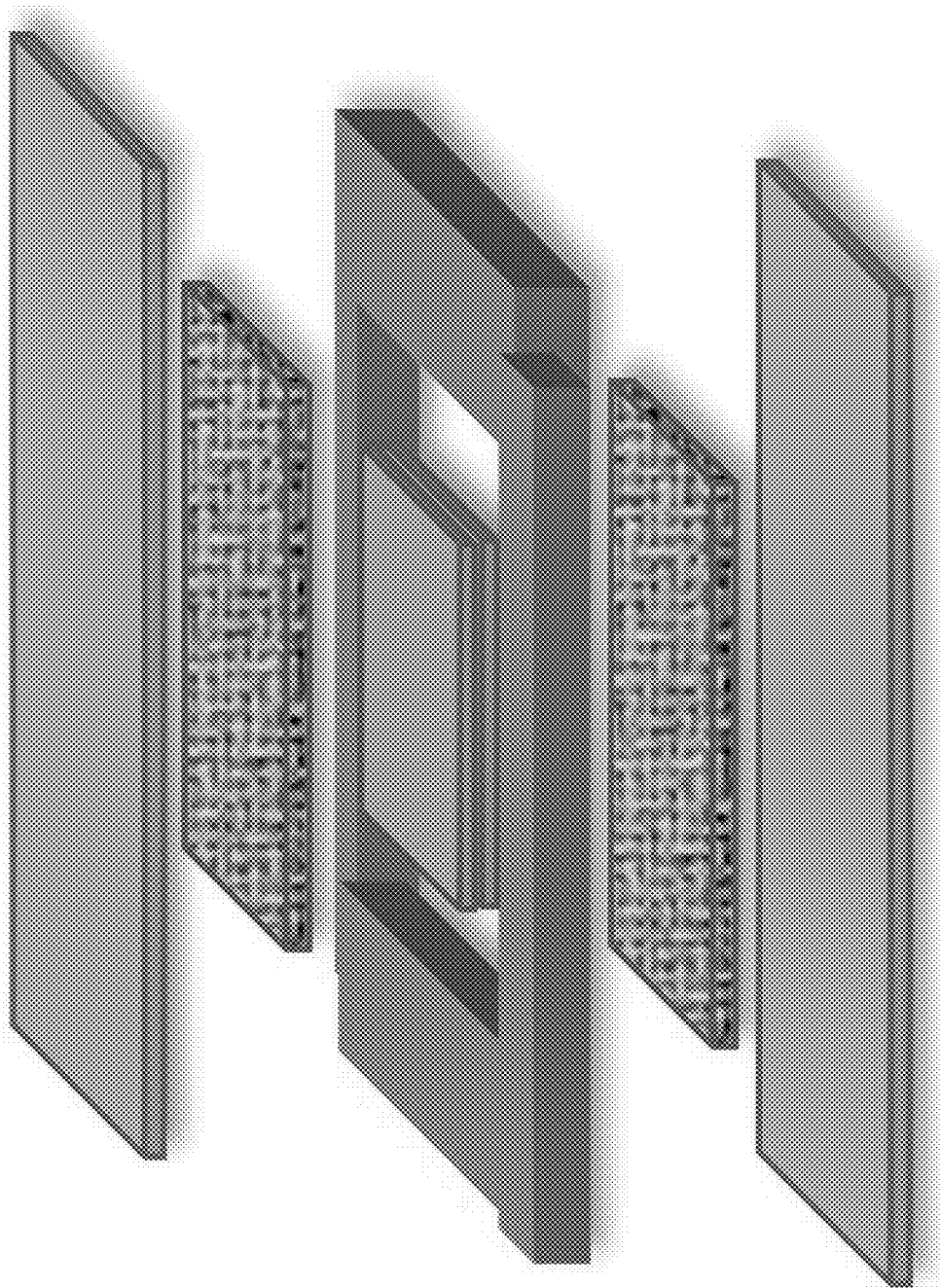
Figure 13D:
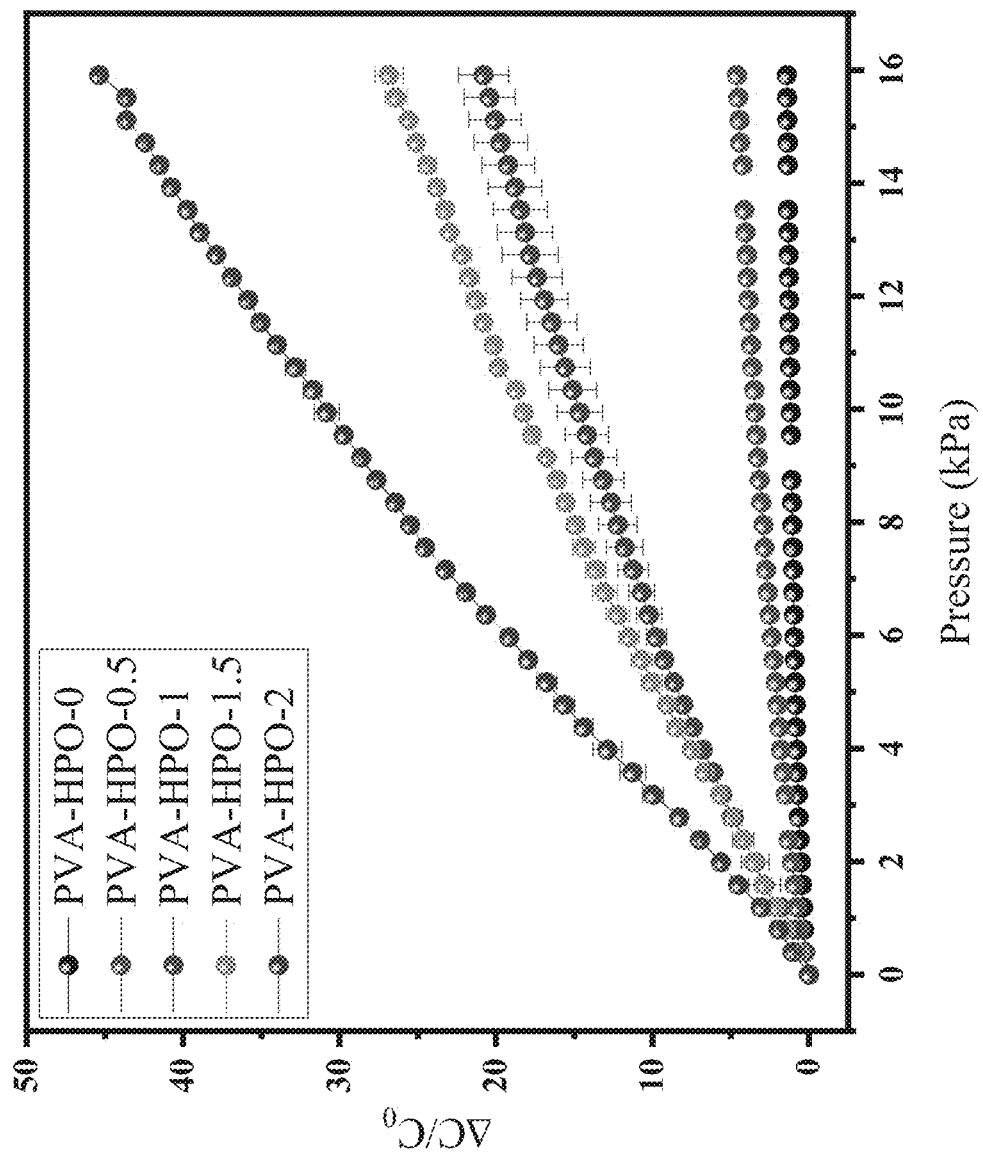
Figure 13E:
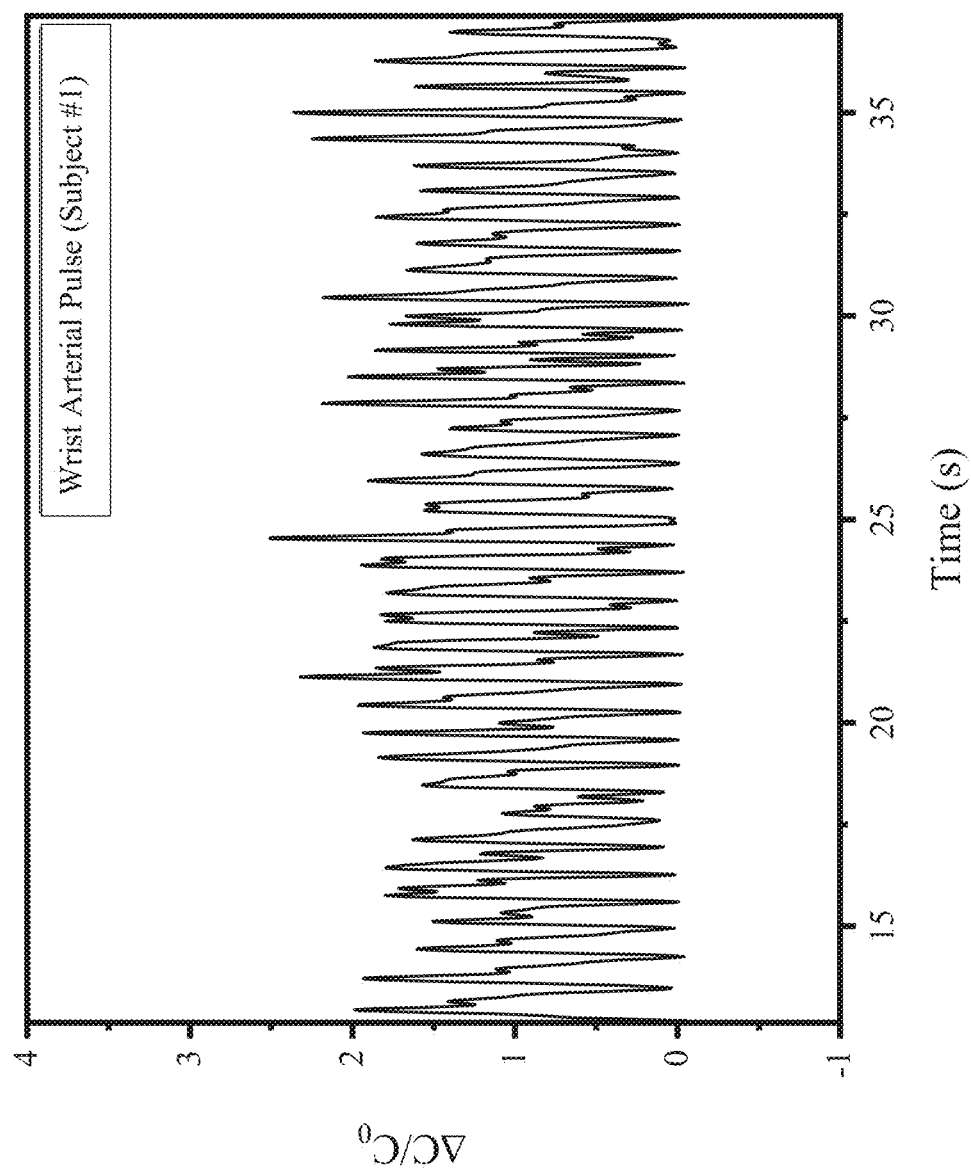
Figure 13F:
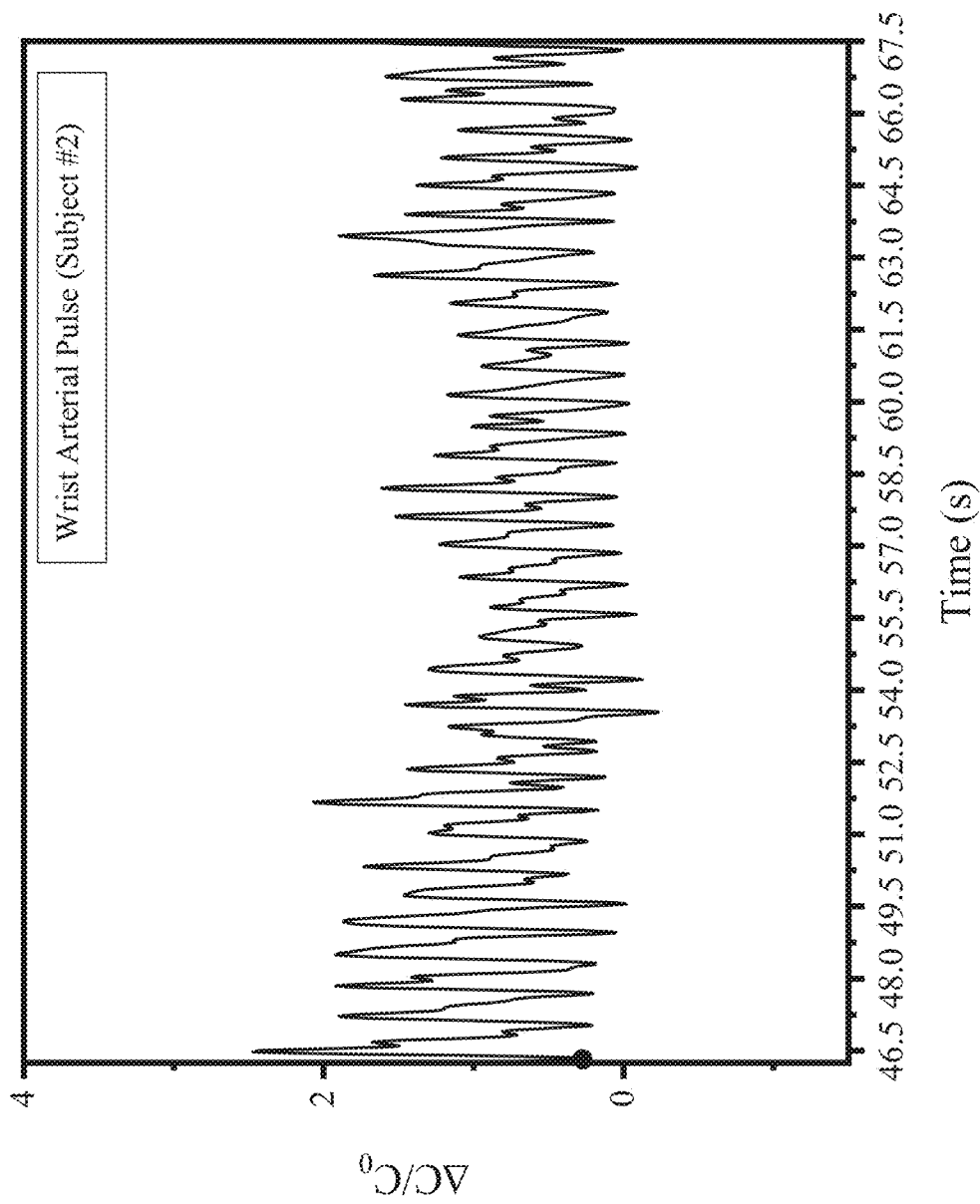
Figure 13G:
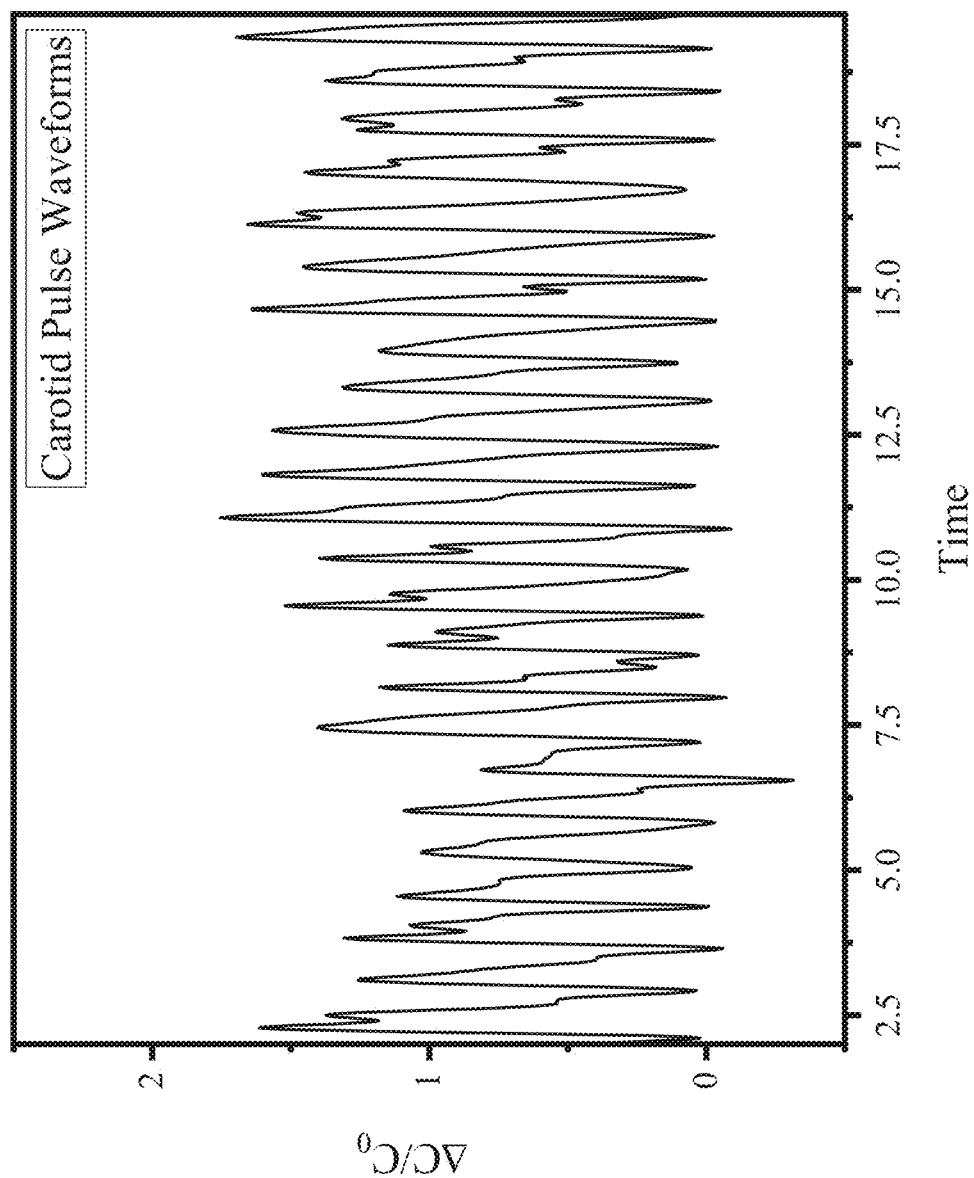

As shown in FIGS. 13A-13G fabrication, characterization, and testing of a mode III (capacitive) sensor according to an embodiment of the subject invention was completed. FIG. 13A schematically illustrates a process comprising: preparing a PVA/H3PO4 solution, blade coating tissue paper, drying in an oven for 15 minutes at 70° F., and cutting the dielectric layer to the desired size; the sensor produced; and selected test and characterization results. FIG. 13B shows a photograph of an actual prototype sensor fabricated according to the process shown in FIG. 13A above a schematic representation of the layers of the same sensor. FIG. 13C shows a schematic exploded view of sensor components: top polyimide layer, conductive textile, solid electrolyte, membrane spacer, conductive textile, and bottom polyimide layer. FIG. 13D is a chart showing relative capacitance response to pressure for five different PVA-HPO formulations. FIG. 13E is a detailed chart showing relative capacitance response over time for wrist arterial pulse (subject #1). FIG. 13F is a detailed chart showing relative capacitance response over time for wrist arterial pulse (subject #2). FIG. 13G is a detailed chart showing relative capacitance response over time for carotid pulse waveforms.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A wearable multi-modal pressure sensor (WMMPS) for detection and intelligent monitoring of weak human physiological signals, the WMMPS comprising three pressure sensors vertically stacked within a common sensor footprint, the three pressure sensors comprising:
a supercapacitive or strain gauge sensor;
a piezoresistive sensor; and
a capacitive sensor,
the piezoresistive sensor comprising an upper surface in direct physical contact with a lower surface of the supercapacitive or strain gauge sensor,
the piezoresistive sensor comprising a plurality of patterned micro-pyramids disposed on a lower surface of the piezoresistive sensor opposite from the upper surface thereof,
the plurality of patterned micro-pyramids being in direct physical contact with an upper surface of the capacitive sensor,
the piezoresistive sensor further comprising a porous polydimethylsiloxane (PDMS) and multiwalled carbon nanotube (MWCNT) composite-based dielectric layer,
the plurality of patterned micro-pyramids being arranged on one side of the porous PDMS and MWCNT composite-based dielectric layer, and
the PDMS and MWCNT composite-based dielectric layer comprising about 1.6 wt % of MWCNT.

2. The WMMPS according to claim 1, the plurality of patterned micro-pyramids being coated on one side of the porous PDMS and MWCNT composite-based dielectric layer such that a conductivity value of the PDMS and MWCNT composite-based dielectric layer coated with the plurality of micro-pyramids is greater than a conductivity value of the porous PDMS and MWCNT composite-based dielectric layer having no patterned micro-pyramids arranged thereon.

3. The WMMPS according to claim 1, a conductivity value of the porous PDMS and MWCNT composite-based dielectric layer having the plurality of patterned micro-pyramids arranged thereon being greater than 2 Siemens per meter (S/m).

4. The WMMPS according to claim 3, the conductivity of the porous PDMS and MWCNT composite-based dielectric layer having the plurality of patterned micro-pyramids arranged thereon being equal to or greater than 10 S/m.

5. The WMMPS according to claim 1, the plurality of patterned micro-pyramids arranged on one side of the porous PDMS and MWCNT composite-based dielectric layer having an average pyramid angle of between 50 and 60 degrees.

6. The WMMPS according to claim 1, the plurality of patterned micro-pyramids arranged on one side of the porous PDMS and MWCNT composite-based dielectric layer having an average size of micro-pyramids of 150 micrometers (μm) or less.

7. The WMMPS according to claim 1, the plurality of patterned micro-pyramids arranged on one side of the porous PDMS and MWCNT composite-based dielectric layer having an average number density of 3 millimeters$^{-1}$ (mm$^{-1}$) or less.

8. The WMMPS according to claim 1, the plurality of patterned micro-pyramids arranged on one side of the porous PDMS and MWCNT composite-based dielectric layer forming a functional part of each of the piezoresistive sensor and the capacitive sensor, respectively.

9. The WMMPS according to claim 1, the supercapacitive or strain gauge sensor comprising a supercapacitive sensor.

10. The WMMPS according to claim 1, the supercapacitive or strain gauge sensor comprising a strain gauge sensor.

* * * * *